United States Patent [19]

Austel et al.

[11] Patent Number: 5,455,348
[45] Date of Patent: Oct. 3, 1995

[54] 2-PYRROLIDINONES, PHARMACEUTICAL COMPOSITIONS CONTAINING THESE COMPOUNDS AND PROCESSES FOR PREPARING THEM

[75] Inventors: Volkhard Austel; Wolfgang Eisert, both of Biberach; Frank Himmelsbach; Guenter Linz, both of Mittelbiberach; Thomas Mueller, Biberach; Helmut Pieper, Biberach; Johannes Weisenberger, Biberach, all of Germany

[73] Assignee: Thomae; Karl, Biberach an der Riss, Germany

[21] Appl. No.: 173,603

[22] Filed: Dec. 23, 1993

Related U.S. Application Data

[63] Continuation of Ser. No. 929,870, Aug. 14, 1992, abandoned.

[30] Foreign Application Priority Data

Aug. 19, 1991 [DE] Germany ................ 41 27 404.0

[51] Int. Cl.$^6$ ................................ C07D 403/12
[52] U.S. Cl. .............................. 544/238; 514/85; 514/86; 514/252; 540/594; 544/58.6; 544/122; 544/224; 544/239; 544/311; 544/332; 544/372; 546/22; 546/23; 546/139; 546/143; 546/144; 546/145; 546/147; 546/186; 546/208; 546/238; 546/245; 546/281; 546/286; 546/298; 546/307; 546/316; 546/330; 548/162; 548/190; 548/195; 548/205; 548/266.2; 548/364.1; 548/491; 548/517; 548/551; 558/415
[58] Field of Search .................... 514/252, 85; 544/238, 544/357, 405, 408, 336, 337, 232; 548/551

[56] References Cited

U.S. PATENT DOCUMENTS

| | | | |
|---|---|---|---|
| 3,149,954 | 9/1964 | Harrod | 548/551 |
| 3,192,209 | 6/1965 | Lunsford | 548/551 |
| 3,364,221 | 1/1968 | Cislak. | |
| 4,216,221 | 8/1980 | deLannoy | 548/551 |
| 4,247,466 | 1/1981 | Chiccareli. | |
| 4,870,076 | 9/1989 | Heckel et al. | 544/238 |
| 4,992,462 | 2/1991 | Hübsch et al. | 544/238 |
| 5,034,402 | 7/1991 | Aschwanden et al. | 514/252 |
| 5,066,663 | 11/1991 | Hobbs | 544/238 |
| 5,084,466 | 1/1992 | Alig et al. | 514/353 |
| 5,270,327 | 12/1993 | Terada | 544/238 |
| 5,314,886 | 5/1994 | Becker et al. | 514/252 |

FOREIGN PATENT DOCUMENTS

| | | |
|---|---|---|
| 0381033 | 8/1990 | European Pat. Off.. |
| 0483667 | 5/1992 | European Pat. Off.. |

OTHER PUBLICATIONS

Burger, Ed, "Medicinal Chemistry 2d Ed." Inter–Science, N.Y. 1960 p. 42.

Primary Examiner—Donald G. Daus
Attorney, Agent, or Firm—Alan Stempel; Mary-Ellen Devlin; Robert Raymond

[57] ABSTRACT

The invention relates to cyclic imino derivatives of general formula $$B-X_5-X_4-X_3-X_2-X_1-A-Y-E \qquad (I)$$

wherein

A, B, E, $X_2$ to $X_5$ and Y are defined as in claim 1, the stereoisomers, tautomers, mixtures and salts thereof, particularly the physiologically acceptable salts thereof with inorganic or organic acids or bases, which have valuable pharmacological properties, preferably aggregation-inhibiting effects, pharmaceutical compositions which contain these compounds and processes for preparing them.

9 Claims, No Drawings

2-PYRROLIDINONES, PHARMACEUTICAL COMPOSITIONS CONTAINING THESE COMPOUNDS AND PROCESSES FOR PREPARING THEM

This is a Continuation of application Ser. No. 929,870, filed Aug. 14, 1992 now abandoned.

The invention relates to cyclic imino derivatives of general formula

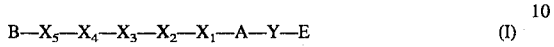

$$B-X_5-X_4-X_3-X_2-X_1-A-Y-E \quad (I)$$

with the exception of the compounds 1-(2-carboxyethyl)-4-[3-(4-piperidinyl)propyl]-piperidine, 1-(carboxymethyl)-4-[5-(4-piperidinyl)pentyl]piperidine, 1-(2-carboxyethyl)-4-[3-(2-piperidinyl)propyl]piperidine, 1-(2-carboxyethyl)-3-[3-(3-piperidinyl)propyl]piperidine and 1-(4-carboxybutyl)-4-[3-(4-piperidinyl)propyl]piperidine, known from U.S. Pat. No. 3,364,221 for the preparation of polyamide plastics and corrosion inhibitors, and processes for preparing them.

The compounds of general formula I, including 1-(2-carboxyethyl)-4-[3-(4-piperidinyl)propyl]piperidine, 1-(carboxymethyl)-4-[5-(4-piperidinyl)pentyl]piperidine, 1-(2-carboxyethyl)-4-[3-(2-piperidinyl)propyl]piperidine, 1-(2-carboxyethyl)-3-[3-(3-piperidinyl)propyl]piperidine and 1-(4-carboxybutyl)-4-[3-(4-piperidinyl)propyl]piperidine, the stereoisomers, tautomers and mixtures thereof and the addition salts thereof, particularly the physiologically acceptable addition salts thereof with inorganic or organic acids or bases, have inter alia valuable pharmacological properties, preferably aggregation-inhibiting effects.

Thus, the present invention also relates to pharmaceutical compositions which contain a compound of general formula I, including the above-mentioned compounds known from U.S. Pat. No. 3,364,221, the stereoisomers, tautomers and mixtures thereof or the addition salts thereof.

In general formula I above, with the proviso that at least one of the groups $R_1$, $R_2$, $X_3$, $X_5$, $X_5-X_4-X_3$ together or $X_5-X_4$ together contains a heterocyclic group, whilst if $R_1$ contains a saturated heterocyclic group with one or two imino groups, one of the groups $R_2$, $X_3$, $X_5$, $X_5-X_4-X_3$ together or $X_5-X_4$ together contains another heterocyclic group, A denotes a 4-, 5-, 6- or 7-membered cyclic alkyleneimino group substituted by the groups $R_1$, $R_2$ and $R_3$, and wherein a methylene group may be replaced by a carbonyl group, and in a 5- to 7-membered ring thus obtained an ethylene group may additionally be replaced by an ethenylene group, whilst $R_1$ denotes a hydrogen atom, an alkyl group which may be substituted by a cycloalkyl-, aryl-, heteroaryl-, biphenylyl-, alkylsulphenyl-, alkylsulphinyl-, alkylsulphonyl-, aryloxy-, arylsulphenyl-, arylsulphinyl-, arylsulphonyl-, amino-, alkylcarbonylamino-, N-alkyl-alkylcarbonylamino-, arylcarbonylamino-, N-alkyl-arylcarbonylamino-, alkylsulphonylamino-, N-alkyl-alkylsulphonylamino-, arylsulphonylamino-, N-alkyl-arylsulphonylamino-, carboxy-, alkoxycarbonyl-, aminocarbonyl-, aralkylaminocarbonyl-, alkylaminocarbonyl-, dialkylaminocarbonyl- or di-(alkoxyalkyl)aminocarbonyl group, by a cycloalkyleneiminocarbonyl group having 4 to 7 carbon atoms in the cycloalkylene moiety, whilst additionally in a piperidinocarbonyl group the methylene group in the 4-position may be replaced by an oxygen or sulphur atom or by a sulphinyl, sulphonyl, imino, alkylimino, alkylcarbonylimino, alkylsulphonylimino, phenylcarbonylimino- or phenylsulphonylimino group, or $R_1$ may also represent an alkyl group which may be substituted by a hydroxy or alkoxy group, an aryl or heteroaryl group, a carbonyl group which is substituted by an alkyl, alkoxyalkyl, amino, alkylamino, dialkylamino, tetrahydrofuranyl, aryl, heteroaryl, aralkyl or heteroaralkyl group, or a sulphonyl group substituted by an alkyl, amino, alkylamino, dialkylamino or aryl group, $R_2$ denotes a hydrogen atom or an alkyl, aryl, aralkyl or heteroaryl group and $R_3$ denotes a hydrogen atom or an alkyl group, with the provisos that a heteroatom of group $R_1$ or $R_2$ is not bound in the α-position to the nitrogen atom of group A, a heteroatom of group $R_1$ is not bound to the ring nitrogen atom of group A via a methylene group optionally substituted by one or two alkyl groups, and a carbonyl or sulphonyl group of group $R_1$ is not bound to the ring nitrogen atom of group A, if A denotes a lactam ring, $X_1$ denotes a bond or a straight-chained or branched $C_{1-3}$-alkylene group, $X_2$ denotes a bond, an oxygen atom, an —$SO_2NH$—, —$NH$—, —$NH$—$CO$—$NH$—, alkylimino, alkylsulphonylimino, alkylcarbonylimino, sulphenyl, sulphinyl, sulphonyl or carbonyl group or a —CONH— or —NHCO— group optionally substituted at the nitrogen atom by an alkyl group, $X_3$ and $X_5$, which may be identical or different, denote a $C_{3-7}$-cycloalkylene group (whilst in a $C_{4-7}$-cycloalkylene group a methylene group may be replaced by an oxygen or sulphur atom or by a sulphonyl, imino or methylimino group or in a $C_{6-7}$-cycloalkylene group a further methylene group in the 4-position may be replaced by an imino or methylimino group), an arylene group or a heteroarylene group wherein one or two methine groups adjacent to an N-atom may be replaced by a hydroxymethine group, and one of the two groups $X_3$ or $X_5$ additionally may represent a straight-chained or branched $C_{1-4}$-alkylene group or an alkenylene or alkynylene group having 2 to 4 carbon atoms, $X_4$ denotes a bond, an oxygen atom, a methylene, ethylene, carbonyl, imino, sulphenyl, sulphinyl, sulphonyl, —NHCO—, —CONH—, —$NHSO_2$—or —$SO_2NH$— group or $X_5-X_4-X_3$ may together also represent a phenyl ring onto two adjacent carbon atoms of which is fused a 6-membered heteroaromatic ring which may contain one or two N-atoms or an n-propylene, n-butylene or n-pentylene bridge in which a carbon atom in each alkylene bridge is replaced by an imino group, one of the groups B and $X_2$ being bound to the phenyl ring and the other group being bound to the fused-on ring, or $X_5-X_4$ together may also denote a phenyl ring onto two adjacent carbon atoms of which is fused a 6-membered heteroaromatic ring which may contain one or two N-atoms or an n-propylene, n-butylene or n-pentylene bridge in which a carbon atom in each alkylene bridge is replaced by an imino group, one of the groups B and $X_3$ being bound to the phenyl ring and the other group being bound to the fused-on ring, with the provisos that
a carbonyl or sulphonyl group of $X_2$ or $X_4$ is not linked to a ring nitrogen atom of a heteroarylene group of $X_3$ or $X_5$,
a carbonyl or sulphonyl group of $X_2$ is not bound to the ring nitrogen atom of group A, if A denotes a lactam ring,
a heteroatom of group $X_2$ or $X_3$ is not bound to the ring nitrogen atom of group A via a methylene group optionally substituted by one or two alkyl groups,
a heteroatom of group $X_2$ or $X_3$ is not bound at the $\alpha$-position to the ring nitrogen atom of group A,
no further heteroatom is bound in the $\alpha$-position to the nitrogen atom of a partially or wholly saturated cyclic imine of the group $X_3$, $X_5$, $X_5$—$X_4$—$X_3$ or $X_5$—$X_4$,
no further heteroatom is bound in the $\alpha$-position to an oxygen or sulphur atom of a saturated heterocyclic group of group $X_3$ or $X_5$,
a heteroatom of group $X_3$ is not linked via a methylene group of group $X_4$ to a heteroatom of group $X_5$, and
a heteroatom of group A, $X_2$, $X_3$, $X_4$, $X_5$ or $X_5$—$X_4$ is not bound to an ethenyl or ethynyl group of group $X_3$ or $X_5$, B denotes an amino, aminoalkylene, amidino, guanidino or guanidinoalkylene group wherein a hydrogen atom on one of the nitrogen atoms may be replaced by an alkyl, benzyl, ($C_{1-4}$alkoxy)carbonyl, $R_4$—CO—O—($R_5$CH)—O—CO— or phenylalkoxycarbonyl group, wherein
$R_4$ denotes an alkyl, phenyl $C_{1-3}$alkyl, or phenyl group and
$R_5$ denotes a hydrogen atom or a methyl or ethyl group,
or, if B denotes an amidino group, the hydrogen atom may also be replaced by a phosphono, O,O'-dimethylphosphono or O,O'-diethylphosphono group, or B may denote a cyano group, a cyanoalkylene group or, if $X_5$ is a pyridylene ring, B may additionally represent a hydrogen atom or, if $X_5$—$X_4$—$X_3$ or $X_5$—$X_4$ denotes an isoquinolinylene ring and B is linked to the heterocyclic moiety of the isoquinoline ring, B may additionally represent a hydrogen atom, or if B is linked to the imino group of an imidazole ring of the group $X_5$, B may additionally represent a hydrogen atom or a methyl group or, if B is linked to the nitrogen atom of a cyclic alkyleneimino group of the group $X_5$—$X_4$—$X_3$, $X_5$—$X_4$ or $X_5$, B may additionally represent a hydrogen atom or a methyl, ($C_{1-4}$alkoxy)carbonyl, phenylalkoxycarbonyl or $R_4$—CO—O—($R_5$CH)—O—CO— group wherein $R_4$ and $R_5$ are defined as hereinbefore, with the provisos that
a cyano or amidino group is not bound to a nitrogen atom of a heteroarylene group of the group $X_5$,
a nitrogen atom of group B is not linked to a heteroatom of group $X_5$, $X_5$—$X_4$—$X_3$, $X_5$—$X_4$, $X_4$ or $X_3$ via a methylene group optionally substituted by one or two alkyl groups,
a nitrogen atom or a cyano group of group B is not bound in the e-position to an oxygen, nitrogen or sulphur atom of a partially or wholly saturated heterocycle of the group $X_5$, $X_5$—$X_4$ or $X_5$—$X_4$—$X_3$, and
a nitrogen atom of group B is not bound to an ethenyl or ethynyl group of $X_5$, Y denotes a straight-chained or branched alkylene group, an —NH—$CH_2$— group optionally alkyl-substituted at the nitrogen atom, or an —O—$CH_2$— or —S—$CH_2$— group, with the provisos that
Y is not bound via a heteroatom to the nitrogen atom of group A and
a heteroatom of group Y is not bound in the $\alpha$-position to the nitrogen atom of group A, and E denotes a carboxy group or an alkoxycarbonyl group having a total of 2 to 7 carbon atoms which may be substituted in the alkyl moiety from position 2 by a morpholino or pyrrolidin-2-on-1-yl group, or E represents a phenylalkoxycarbonyl group which may be substituted in the phenyl nucleus by one or two methoxy groups, or E represents an $R_6$—CO—O—($R_7$CH)—O—CO— or $R_8$O—CO— group, wherein
$R_6$ denotes a $C_{1-7}$-alkyl group, a $C_{5-7}$-cycloalkyl group, a $C_{1-4}$-alkoxy group, a $C_{5-7}$-cycloalkoxy group, a phenyl, phenoxy, phenylalkyl or phenylalkoxy group, each having 1 to 3 carbon atoms in the alkyl moiety,
$R_7$ denotes a hydrogen atom, a $C_{1-3}$-alkyl group, a $C_{5-7}$-cycloalkyl group or a phenyl group and
$R_8$ denotes a $C_{4-8}$-cycloalkyl group or a cycloalkylalkyl group having 3 to 8 carbon atoms in the cycloalkyl moiety and 1 to 3 carbon atoms in the alkyl moiety, wherein the above-mentioned cycloalkyl moieties may additionally be substituted by a $C_{1-4}$-alkyl group or by a $C_{1-4}$-alkyl group and 1 to 3 methyl groups or by an alkoxy or dialkylamino group each having 1 to 4 carbon atoms in the alkoxy or alkyl moiety, by a phenyl, trifluoromethyl or $C_{3-6}$-cycloalkyl group, or by a fluorine, chlorine or bromine atom and additionally a methylene group in the above-mentioned cycloalkyl moieties which contain 4 to 8 carbon atoms may be replaced by an oxygen or sulphur atom, by an alkylimino group having 1 to 4 carbon atoms in the alkyl moiety or by a sulphinyl or sulphonyl group with the proviso that there are at least 2 carbon atoms between the ring heteroatom and the next heteroatom, or $R_8$ represents a cycloalkenyl or cycloalkenylalkyl group having 5 to 8 carbon atoms in the cycloalkenyl moiety and 1 to 3 carbon atoms in the alkyl moiety, wherein the above-mentioned cycloalkenyl moieties may additionally be substituted by a $C_{1-4}$-alkyl group or by a $C_{1-4}$-alkyl group and 1 to 3 methyl groups, with the proviso that the above-mentioned cycloalkenyl moieties are not linked via a carbon atom, from which a double bond starts, to the oxygen atom of the adjacent —O—CO— group, or $R_8$ represents a bi- or tricycloalkyl or bi- or tricycloalkylalkyl group each having 6 to 10 carbon atoms in the bi- or tricycloalkyl moiety and 1 to 3 carbon atoms in the alkyl moiety, whilst the above-mentioned bi- or tricycloalkyl moieties may additionally be substituted by 1 to 3 methyl groups, or $R_8$ represents a bi- or tricycloalkenyl or bi- or tricycloalkenyl-alkyl group each having 6 to 10 carbon atoms in the bi- or tricycloalkenyl moiety and 1 to 3 carbon atoms in the alkyl moiety, whilst the above-mentioned bi- or tricycloalkenyl moieties may additionally be substituted by 1 to 3 methyl groups, with the proviso that the above-mentioned bi- or tricycloalkenyl moieties are not linked via a carbon atom, from which a double bond starts, to the oxygen atom of the adjacent —O—CO— group, or $R_8$ represents a benzocycloalkenyl group having a total of 9 to 12 carbon atoms, wherein the cycloalkenyl moiety may be mono- or disubstituted by 1 or 2 methyl groups and the aromatic moiety may additionally be mono- or disubstituted by fluorine, chlorine or bromine atoms or by methyl, ethyl, methoxy, ethoxy, trifluoromethyl, cyano or methanesulphonyl groups and the substituents may be identical or different, or $R_8$ represents an optionally phenyl-substituted $C_{3-6}$alkenyl or $C_{3-6}$alkynyl group with the proviso that the above-mentioned alkenyl or alkynyl groups are not linked via a carbon atom, from which a double or triple bond starts, to the oxygen atom of the adjacent —O—CO— group, or E represents a pyridinylalkoxycarbonyl, 5-tetrazolyl, O-alkylphosphono, O,O'-dialkylphosphono or phosphono group with the proviso that E is bound to a carbon atom of group Y and the shortest distance between groups B and E is at least 10 bonds, whilst unless otherwise specified the term "cycloalkyl group" denotes a $C_{3-7}$-cycloalkyl group, the term "an aryl group" denotes a phenyl group optionally mono-, di- or trisubstituted by fluorine, chlorine, bromine or iodine atoms, or alkyl, trifluoromethyl, nitro, amino, alkylamino, dialkylamino, alkanoylamino, alkylsulphonylamino, aminosulphonyl, alkylamino-sulphonyl, dialkylaminosulphonyl, hydroxy, alkoxy, cyano, carboxy, alkoxycarbonyl, aminocarbonyl, alkylaminocarbonyl, dialkylaminocarbonyl, alkylsulphenyl, alkylsulphinyl or alkylsulphonyl groups, wherein the substituents may be identical or different, or a naphthyl group, and the term "arylene group" denotes the above-mentioned corresponding aryl groups and the term "heteroaryl group" denotes a 5-membered heteroaromatic ring which contains an imino group, an oxygen or sulphur atom, one to two nitrogen atoms and an oxygen or sulphur atom or an imino group and one to three nitrogen atoms, and a 6-membered heteroaromatic ring containing 1, 2 or 3 nitrogen atoms, whilst a phenyl ring may be fused onto the above-mentioned rings and additionally the above-mentioned rings may be mono- or disubstituted by a fluorine, chlorine or bromine atom or by an alkyl, alkoxy, hydroxy, amino, dialkylamino, alkylcarbonylamino, alkylsulphonylamino, cyano, carboxy, alkoxycarbonyl, aminocarbonyl, alkylaminocarbonyl, dialkylaminocarbonyl, or trifluoromethyl group or by a $C_{1-4}$-alkylamino group, wherein the substituents may be identical or different, and the term "heteroarylene group" denotes the above-mentioned corresponding heteroaryl groups, and unless otherwise specified the above-mentioned alkyl, alkylene or alkoxy moieties may each contain 1 to 4 carbon atoms and the alkanoyl moieties may contain 2 to 4 carbon atoms.

Examples of the rings mentioned hereinbefore in the definition of groups $X_3$ and $X_5$ include, for example, the phenylene, trifluoromethylphenylene, fluorophenylene, chlorophenylene, bromophenylene, methylphenylene, methylsulphenylphenylene, methylsulphinylphenylene, methylsulphonylphenylene, methoxyphenylene, nitrophenylene, aminophenylene, acetylaminophenylene, methylsulphonylaminophenylene, dimethylphenylene, dimethoxyphenylene, pyridinylene, pyrimidinylene, pyrazinylene, pyridazinylene, furylene, pyrrolylene, N-methyl-pyrrolylene, thiazolylene, imidazolylene, 1-methyl-imidazolylene, 1H-1,2,4-triazolylene, pyrazolylene, 1H-pyridin-2-onylene, 1H,3H-pyrimidin-2,4-dionylene, 2H-pyridazin-3-onylene, 2H-2-methyl-pyridazin- 3-onylene, piperidinylene or piperazinylene group, $X_5$—$X_4$—$X_3$ together may represent an isoindolinylene, 1,2,3,4-tetrahydro-isoquinolinylene or 1H-2,3,4,5-tetrahydro- 3-benzazepinylene group and $X_5$—$X_4$ together may represent an isoquinolinylene or 1,2,3,4-tetrahydroisoquinolinylene group.

Preferred compounds of general formula I above are those wherein

A denotes a pyrrolidine or pyrrolidinone ring substituted by the groups $R_1$ to $R_3$, wherein $R_1$ to $R_3$ are as hereinbefore defined, and the other groups $X_1$ to $X_5$, Y, B and E are as mentioned above, particularly those compounds wherein A denotes a 5-membered cyclic alkyleneimino group substituted by the groups $R_1$ and $R_2$, and in which a methylene group in the 2-position may be replaced by a carbonyl group, whilst $R_1$ denotes a hydrogen atom, a $C_{1-4}$-alkyl group which may be substituted by a phenyl, trifluoromethylphenyl, methylsulphenylphenyl, methylsulphinylphenyl, methylsulphonylphenyl, fluorophenyl, chlorophenyl, methylphenyl, methoxyphenyl, dichlorophenyl or dimethoxyphenyl group, a methyl group substituted by a carboxy, methoxycarbonyl, dimethylaminocarbonyl, pyrrolidinocarbonyl, piperidinocarbonyl, morpholinocarbonyl, thiomorpholinocarbonyl, 1-oxidothiomorpholinocarbonyl or 1,1-dioxido-thiomorpholinocarbonyl group, a 2-methoxy-ethyl, phenyl, pyridinyl, pyrimidinyl, pyrazinyl, pyridazinyl or benzothiazolyl group, a carbonyl group which is substituted by a phenyl, pyridinyl, methyl, methoxymethyl, amino, methylamino, ethylamino, dimethylamino, tetrahydrofuranyl, furyl, thiazolyl, 2-methyl-thiazolyl, pyrazolyl or 1H-1,2,4-triazolylmethyl group, or a sulphonyl group which is substituted by a methyl, phenyl, methoxyphenyl, amino, methylamino or dimethylamino group, and $R_2$ denotes a hydrogen atom or a methyl group, with the provisos that a carbonyl group of the group $R_1$ is not linked to the nitrogen atom of group A if A represents a lactam ring, and a sulphonyl group of group $R_1$ is not linked to the nitrogen atom of group A if A denotes a lactam ring, and is also not positioned at a carbon atom adjacent to the ring nitrogen, $X_1$ denotes a bond or a methylene or ethylene group, $X_2$ denotes a bond, an oxygen atom, a —CONH— group or an imino group optionally substituted by a methyl, acetyl or methanesulphonyl group, $X_3$ and $X_5$, which may be identical or different, represent a phenylene group optionally substituted by a fluorine, chlorine or bromine atom, or by a methyl, trifluoromethyl, methoxy, nitro, amino, acetylamino, methanesulphonylamino, methylsulphenyl, methylsulphinyl or methylsulphonyl group or by two methyl groups, or they represent a pyridinylene, pyrimidinylene, pyrazinylene, pyridazinylene, thiazolylene, furylene, pyrrolylene, imidazolylene, thienylene, 1H-pyridin-2-onylene, 1H,3H-pyrimidin-2,4-dionylene or 2H-pyridazin-3-onylene group optionally substituted by a methyl group or substituted at a carbon atom by a chlorine atom, or a piperidinylene or piperazinylene group optionally substituted by a methyl group, and $X_4$ represents a bond or an —NHCO— group or $X_5$—$X_4$—$X_3$ together represent a phenyl ring onto which a 5-, 6- or 7-membered saturated ring containing an imino nitrogen atom is fused via two adjacent carbon atoms, one of the groups B and $X_2$ being bound to the phenyl ring whilst the other group is bound to the fused-on ring, or $X_5$—$X_4$ together may also denote an isoquinolinylene ring, whilst the group B is in position 1 or 3 and the group $X_3$ is in position 5, 6, 7 or 8, or a 1,2,3,4-tetrahydroisoquinolinylene ring, where the group B is in the 2-position and the group $X_3$ is in position 5, 6, 7 or 8, with the provisos that A and $X_2$, A and $X_3$, $X_2$ and $X_3$, $X_2$ and $X_5$—$X_4$—$X_3$, $X_3$ and $X_5$, $X_4$ and $X_5$ are not linked together via two heteroatoms, a carbonyl group of $X_2$ or $X_4$ is not linked to a ring nitrogen atom of a 1H-pyridin-2-onylene, 1H,3H-pyrimidin- 2,4-dionylene, 2H-pyridazin-3-onylene, pyrrolylene or imidazolylene group mentioned for $X_3$, a heteroatom of group $X_2$ or $X_3$ is not bound via a methylene group to the ring nitrogen atom of group A, a heteroatom of group $X_2$ or $X_3$ is not bound in the α-position to the ring nitrogen atom of group A, a furylene, pyrrolylene or thienylene ring of group $X_3$ or $X_5$ is not linked to a heteroatom of group A, $X_2$, $X_3$, $X_4$ or $X_5$, no further heteroatom is bound in the α-position to the nitrogen atom of a wholly or partially saturated cyclic imine of the group $X_3$, $X_5$ or $X_5$—$X_4$—$X_3$, B denotes an aminomethyl group with the proviso that the aminomethyl group is not bound to a ring nitrogen atom of group $X_5$, $X_5$—$X_4$ or $X_5$—$X_4$—$X_3$, a cyano or amidino group with the proviso that the cyano or amidino group is not bound to a ring nitrogen atom of a 1H-pyridin-2-onylene, 1H,3H-pyrimidin-2,4-dionylene, 2H-pyridazin-3-onylene, pyrrolylene or imidazolylene group mentioned for $X_5$, a guanidino group, with the proviso that the guanidino group is not bound to a ring nitrogen atom of the group $X_5$, $X_5$—$X_4$ or $X_5$—$X_4$—$X_3$, is not in the α-position relative to a nitrogen atom of a partially or wholly saturated cyclic imine of the group $X_5$ or $X_5$—$X_4$—$X_3$ and is not bound to a furylene, pyrrolylene or thienylene group mentioned for $X_5$, an amino group with the proviso that the amino group is not bound to a ring nitrogen atom of the group $X_5$, $X_5$—$X_4$ or $X_5$—$X_4$—$X_3$, is not in the α-position relative to a nitrogen atom of a wholly or partially saturated cyclic imine of the group $X_5$ or $X_5$—$X_4$—$X_3$ and is not bound to a furylene, pyrrolylene or thienylene group mentioned for $X_5$, a hydrogen atom or a methyl group, with the proviso that B is linked to a ring nitrogen atom of the group $X_5$, $X_5$—$X_4$ or $X_5$—$X_4$—$X_3$ and $X_5$ denotes a piperidinylene or piperazinylene group and $X_5$—$X_4$ denotes a 1,2,3,4-tetrahydro-isoquinolinylene group or a hydrogen atom with the proviso that $X_5$—$X_4$ denotes an isoquinolinylene group or $X_5$ denotes a pyridinylene group, whilst if B denotes an amino, aminomethyl, amidino or guanidino group, a hydrogen atom at one of the nitrogen atoms may be replaced by a methyl, benzyl, ($C_{1-4}$alkoxy)carbonyl, benzyloxycarbonyl or $R_4$—CO—O—($R_5$CH)—O—CO— group, wherein
$R_4$ is a $C_{1-4}$-alkyl group and
$R_5$ is a hydrogen atom or a methyl group, or, if B denotes an amidino group, a hydrogen atom may also be replaced by an O,O'-dimethyl-phosphono or O,O'-diethyl-phosphono group, Y represents a methylene or ethylene group and E denotes a carboxy group, an alkoxycarbonyl group having a total of 2 to 7 carbon atoms, a phenylalkoxycarbonyl group having 1 to 3 carbon atoms in the alkoxy moiety, an O-methyl-phosphono, O,O'-dimethylphosphono, phosphono, $R_6$—CO—O—($R_7$CH)—O—CO— or $R_8$O—CO— group, wherein $R_6$ denotes a $C_{1-4}$-alkyl group, a cyclohexyl or phenyl group, a $C_{1-4}$-alkoxy group or a $C_{5-7}$-cycloalkoxy group, $R_7$ denotes a hydrogen atom or a methyl group and $R_8$ denotes a cycloalkyl, cycloalkylmethyl or cycloalkylethyl group each having 5 to 8 carbon atoms in the cycloalkyl moiety, whilst the above-mentioned cycloalkyl moieties may additionally be substituted by a $C_{1-4}$-alkyl group or by a $C_{1-4}$-alkyl group and 1 to 3 methyl groups, by a methoxy, ethoxy, dimethylamino, diethylamino or trifluoromethyl group and, furthermore, in the above-mentioned cycloalkyl moieties a methylene group may be replaced by an oxygen atom or by a methylimino or ethylimino group, with the proviso that there are at least 2 carbon atoms between the cyclic heteroatom and the next heteroatom, or $R_8$ represents a cyclohexenyl or cyclohexenylmethyl group, whilst the above-mentioned cyclohexenyl moieties may additionally be substituted by a methyl group, with the proviso that the above-mentioned cyclohexenyl moieties are not linked to the oxygen atom of the adjacent —O—CO— group via a carbon atom from which a double bond starts, or $R_8$ represents a bicycloalkyl or bicycloalkylalkyl group each having 6 to 8 carbon atoms in the bicycloalkyl moiety and 1 or 2 carbon atoms in the alkyl moiety, whilst the above-mentioned bicycloalkyl moieties may additionally be substituted by 1 to 3 methyl groups, or $R_8$ represents a bicycloalkenyl or bicycloalkenylalkyl group each having 6 to 8 carbon atoms in the bicycloalkenyl moiety and 1 or 2 carbon atoms in the alkyl moiety, whilst the above-mentioned bicycloalkenyl moieties may additionally be substituted by 1 to 3 methyl groups, with the proviso that the above-mentioned bicycloalkenyl moieties are not linked to the oxygen atom of the adjacent —O—CO— group via a carbon atom from which a double bond starts, or $R_8$ represents a benzocycloalkenyl group having a total of 9 or 10 carbon atoms, or $R_8$ represents an alkenyl or alkynyl group each having 3 to 5 carbon atoms with the proviso that the above-mentioned alkenyl or alkynyl groups are not linked to the oxygen atom of the adjacent —O—CO— group via a carbon atom from which a double or triple bond starts, or or $R_8$ represents a cinnamyl group, with the proviso that the shortest distance between the groups B and E is at least 10 bonds, the stereoisomers, tautomers and mixtures thereof and the addition salts thereof with organic or inorganic acids or bases.

Particularly preferred compounds of general formula I above are those wherein

A represents a pyrrolidine ring optionally substituted in the 1-position by a pyridinecarbonyl or pyrimidinyl group or a 2-pyrrolidinone ring optionally substituted in the 1-position by a 3-phenyl-propyl or pyridinyl group, $X_1$ denotes a methylene or ethylene group, $X_2$ denotes a bond, an oxygen atom or a —CONH— or imino group, $X_3$ represents an optionally methyl-substituted 1,4-phenylene, pyridazin-3,6-ylene, 1H-pyridin-2-on-1,3-ylene, 1H-pyridin-2-on-1,5-ylene, 2H-pyridazin-3-on-4,6-ylene or 1H,3H-pyrimidin-2,4-dion-3,5-ylene group with the proviso that a nitrogen atom of the group $X_3$ is not linked to a heteroatom or the —CONH— group of the group $X_2$, $X_4$ denotes a bond or an —NHCO— group with the proviso that the —NHCO— group is not linked to a nitrogen atom of group $X_3$, and $X_5$ denotes a piperidin-1,4-ylene group, an optionally chlorine-substituted 1,4-phenylene, pyridin-2,4-ylene, pyridin-2,5-ylene, pyrimidin-2,5-ylene, pyrazin-2,5-ylene or thiazol-2,5-ylene group with the proviso that the cyclic nitrogen atom of the piperidin-1,4-ylene group is not linked to a nitrogen atom of the group $X_3$ or $X_4$, or $X_5$—$X_4$—$X_3$ together represent an isoindolin-2,5-ylene, 1,2,3,4-tetrahydro-isoquinolin-2,7-ylene or 1H-2,3,4,5-tetrahydro-3-benzazepin-3,7-ylene group with the proviso that the cyclic nitrogen atom of these groups is not linked to a heteroatom of the group $X_2$, or $X_5$—$X_4$ together represent an isoquinolin-1,6-ylene group, wherein group B is in position 1 and group $X_3$ is in position 6, or a 1,2,3,4-tetrahydro-isoquinolin-2,6-ylene group, wherein group B is in position 2 and group $X_3$ is in position 6, B denotes a cyano group, an amidino group in which, at one of the nitrogen atoms, a hydrogen atom may be replaced by an alkoxycarbonyl group having a total of 2 to 5 carbon atoms, or B represents an optionally benzyl-substituted amino group, with the proviso that the amino group is not linked to a cyclic nitrogen atom of the group $X_5$—$X_4$—$X_3$ or $X_5$, or, if B is linked to a cyclic nitrogen atom of the group $X_5$—$X_4$—$X_3$ or $X_5$ or, if B is linked to the group $X_5$—$X_4$, B may additionally represent a hydrogen atom, Y denotes a methylene group and E denotes a carboxy group or an alkoxycarbonyl group having a total of 2 to 5 carbon atoms, with the proviso that the shortest distance between groups B and E is at least 10 bonds, more particularly those compounds wherein A represents a 2-pyrrolidinone ring optionally substituted in the 1-position by a 3-phenylpropyl, pyridin-2-yl or pyridin-3-yl group or a pyrrolidine ring substituted in the 1-position by a pyridin-3-ylcarbonyl or pyrimidin-2-yl group, $X_2$—$X_1$ denotes an —O—CH$_2$—, —NH—CH$_2$—, —CONH—CH$_2$—, —CONH—CH$_2$C$_2$— or, if $X_3$ denotes a 1H-pyridin-2-on-1,3-ylene, 1H-pyridin-2-on-1,5-ylene or 1H,3H-pyrimidin-2,4-dion-3,5-ylene group, $X_2$—$X_1$ may denote a methylene group, $X_3$ denotes a 1,4-phenylene, pyridazin-3,6-ylene, 1H-pyridin-2-on-1,3-ylene, 1H-pyridin-2-on-1,5-ylene, 2H-pyridazin-3-on-4,6-ylene, 2-methyl-2H-pyridazin-3-on-4,6-ylene or 1H,3H-pyrimidin-2,4-dion-3,5-ylene group, wherein the 1H-pyridin-2-on-1,3-ylene, 1H-pyridin-2-on-1,5-ylene and 1H,3H-pyrimidin-2,4-dion-3,5-ylene group is bound to the group $X_2$—$X_1$ via a cyclic nitrogen atom, $X_4$ denotes a bond or an —NHCO— group and $X_5$ denotes a 1,4-phenylene, pyridin-2,4-ylene, pyridin-2,5-ylene, pyrimidin-2,5-ylene, pyrazin-2,5-ylene, piperidin-1,4-ylene or thiazol-2,5-ylene group, wherein the piperidin-1,4-ylene and pyridin-2,4-ylene group are bound to $X_4$ via position 4, or $X_5$—$X_4$—$X_3$ together represent an isoindolin-2,5-ylene group, which is bound to the group $X_2$—$X_1$ via the benzo moiety, or $X_5$—$X_4$ together represent an isoquinolin-1,6-ylene ring or a 1,2,3,4-tetrahydro-isoquinolin-2,6-ylene ring, if $X_3$ denotes a 1,4-phenylene group, the isoquinolin-1,6-ylene ring and the 1,2,3,4-tetrahydro-isoquinolin-2,6-ylene ring being bound to the 1,4-phenylene group via position 6, B denotes an amidino group wherein, at one of the nitrogen atoms, a hydrogen atom may be replaced by an alkoxycarbonyl group with a total of 2 to 5 carbon atoms or, if $X_5$ denotes a 1,4-piperidinylene group, B may additionally represent a hydrogen atom or, if $X_5$—$X_4$ together represent an isoquinolin-1,6-ylene ring, B may represent an amino group or a hydrogen atom, or, if $X_5$—$X_4$ represents a 1,2,3,4-tetrahydro-isoquinolin-2,6-ylene ring, B may represent a hydrogen atom, or, if $X_5$ denotes a pyridin-2,4-ylene ring, B may represent a benzylamino group, Y denotes a methylene group and E denotes a carboxy group or an alkoxycarbonyl group having a total of 2 to 5 carbon atoms, particularly those compounds wherein A, B, E, $X_1$ to $X_5$ and Y are defined as hereinbefore and the group —Y—E is in position 3 and the group B—$X_5$—$X_4$—$X_3$—$X_2$—$X_1$ is in position 5 of the 2-pyrrolidinone or pyrrolidine ring, and one of the groups $X_5$ or $X_3$ denotes a 1,4-phenylene group, the stereoisomers and tautomers thereof, the mixtures and addition salts thereof with organic or inorganic acids or bases.

According to the invention, the new compounds of general formula I may, for example, be obtained according to the following methods known per se:

a) In order to prepare compounds of general formula I wherein E denotes a carboxy group:

converting a compound of general formula

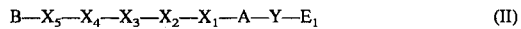

$$B-X_5-X_4-X_3-X_2-X_1-A-Y-E_1 \qquad (II)$$

wherein

A, B, $X_1$ to $X_5$ and Y are as hereinbefore defined and $E_1$, which is bound to a carbon atom, represents a group which may be converted into a carboxy group by hydrolysis, treatment with acids, thermolysis or hydrogenolysis.

For example, functional derivatives of the carboxyl group such as unsubstituted or substituted amides, esters, thioesters, trimethylsilylesters, orthoesters, iminoesters, amidines or anhydrides, or a nitrile group may be converted by hydrolysis into a carboxyl group, esters with tertiary alcohols, e.g. tert.butylesters, may be converted by treatment with an acid or thermolysis into a carboxyl group and esters with aralkanols, e.g. benzylesters, may be converted by hydrogenolysis into a carboxyl group.

The hydrolysis is appropriately carried out either in the presence of an acid such as hydrochloric, sulphuric, phosphoric, trichloroacetic or trifluoroacetic acid, in the presence of a base such as sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture. When treating with an organic acid such as trichloroacetic or trifluoroacetic acid, any alcoholic hydroxy groups present may simultaneously be converted into a corresponding acyloxy group such as a trifluoroacetoxy group.

If E' in a compound of formula II represents a cyano or aminocarbonyl group, these groups may also be converted into a carboxyl group with a nitrite, e.g. sodium nitrite, in the presence of an acid such as sulphuric acid, which may appropriately be used as the solvent at the same time, at temperatures between 0° and 50° C.

If E' in a compound of formula II represents a tert.butyloxycarbonyl group, for example, the tert.butyl group may also be cleaved by treating with an acid such as trifluoroacetic acid, formic acid, p-toluenesulphonic acid, sulphuric acid, phosphoric acid or polyphosphoric acid, optionally in an inert solvent such as methylene chloride, chloroform, benzene, toluene, tetrahydrofuran or dioxane, preferably at temperatures between −10° C. and 120° C., e.g. at temperatures between 0° and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C.

If E' in a compound of formula II represents a benzyloxycarbonyl group, for example, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 10 bar. During hydrogenolysis, other groups may also be reduced at the same time, e.g. a nitro group may be reduced to an amino group or a benzyloxy group to a hydroxy group.

b) In order to prepare compounds of general formula I wherein B represents an amidino group optionally substituted by an alkyl or benzyl group:

Reacting a compound of general formula

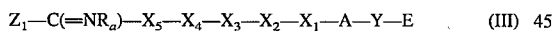

$$Z_1-C(=NR_a)-X_5-X_4-X_3-X_2-X_1-A-Y-E \quad (III)$$

optionally formed in the reaction mixture, wherein A, E, $X_1$ to $X_5$ and Y are as hereinbefore defined, $R_a$ denotes a hydrogen atom, a $C_{1-4}$-alkyl or a benzyl group and $Z_1$ denotes an alkoxy or aralkoxy group such as a methoxy, ethoxy, n-propoxy, isopropoxy or benzyloxy group or an alkylthio or aralkylthio group such as a methylthio, ethylthio, n-propylthio or benzylthio group or an amino group, with an amine of general formula

$$R_a'-NH_2 \quad (IV)$$

wherein $R_a'$ denotes a hydrogen atom, a $C_{1-4}$-alkyl or a benzyl group, or with the acid addition salts thereof.

The reaction is expediently carried out in a solvent such as methanol, ethanol, n-propanol, water, methanol/water, tetrahydrofuran or dioxane at temperatures between 0° and 150° C., preferably at temperatures between 20° and 120° C., with a corresponding free amine or with a corresponding acid addition salt such as for example ammonium carbonate or acetate.

A compound of general formula III may be obtained, for example, by reacting a corresponding nitrile with a suitable alcohol such as methanol, ethanol, n-propanol, isopropanol or benzyl alcohol in the presence of an acid such as hydrochloric acid or in the presence of a corresponding alkoxide such as sodium methoxide or sodium ethoxide or by reacting a corresponding amide with a trialkyloxonium salt such as triethyloxoniumtetrafluoroborate in a solvent such as methylene chloride, tetrahydrofuran or dioxane at temperatures between −10° and 50° C., but preferably at temperatures between 0° and 20° C., or a corresponding nitrile with hydrogen sulphide, appropriately in a solvent such as pyridine or dimethylformamide and in the presence of a base such as triethylamine with subsequent alkylation of the resulting thioamide with a corresponding alkyl or aralkyl halide.

c) In order to prepare compounds of general formula I wherein B contains an amino, amidino or guanidino group substituted by an alkyl or benzyl group, wherein the alkyl moiety may contain 1 to 4 carbon atoms:

Reacting a compound of general formula

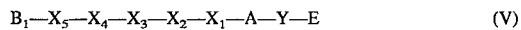

$$B_1-X_5-X_4-X_3-X_2-X_1-A-Y-E \quad (V)$$

wherein $X_1$ to $X_5$, A, E and Y are as hereinbefore defined and $B_1$ contains an amino, amidino or guanidino group, with a compound of general formula

$$Z_2-R_b \quad (VI)$$

wherein $R_b$ denotes an alkyl or benzyl group, whilst the alkyl moiety may contain 1 to 4 carbon atoms, and $Z_2$ denotes a nucleophilic leaving group such as a halogen atom or a sulphonyloxy group, e.g. a chlorine, bromine or iodine atom or a methanesulphonyloxy or p-toluenesulphonyloxy group.

The reaction is conveniently carried out in a solvent or mixture of solvents such as methylene chloride, dimethylformamide, dimethylsulphoxide, toluene, chlorobenzene, tetrahydrofuran, toluene/tetrahydrofuran or dioxane in the presence of an alkylating agent such as methyliodide, ethylbromide, butylbromide, dimethylsulphate or benzyl chloride, preferably in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide, an alkali metal hydride such as sodium hydride or a tertiary organic base such as N-ethyldiisopropylamine, conveniently at temperatures between 0° and 150° C., preferably at temperatures between 0° and 50° C.

d) In order to prepare compounds of general formula I wherein $X_2$ denotes an oxygen or sulphur atom, a sulphonyl group or an imino group optionally substituted by an alkyl, alkylcarbonyl or alkylsulphonyl group:

Reacting a compound of general formula

$$B-X_5-X_4-X_3-X_2'-H \quad (VII)$$

wherein $X_3$ to $X_5$ and B are as hereinbefore defined and $X_2'$ denotes an oxygen or sulphur atom, a sulphonyl group or an imino group optionally substituted by an alkyl, alkylcarbonyl or alkylsulphonyl group, or the alkali metal or alkaline earth metal salts thereof, with a compound of general formula $$Z_3—X_1—A—Y—E \quad (VIII)$$

wherein $X_1$, A, E and Y are as hereinbefore defined and $Z_3$ denotes a nucleophilic leaving group such as a halogen atom or a sulphonyloxy group, e.g. a chlorine, bromine or iodine atom or a methanesulphonyloxy or p-toluenesulphonyloxy group.

The reaction is preferably carried out in a solvent such as tetrahydrofuran, acetonitrile, dioxane, dimethylsulphoxide, sulpholane, dimethylformamide or dimethylacetamide, optionally in the presence of an inorganic base such as potassium carbonate, caesium carbonate, sodium hydroxide, potassium hydroxide, sodium hydride or potassium tert.butoxide or in the presence of a tertiary organic base such as N-ethyldiisopropylamine, which may optionally also serve as solvent, and possibly also in the presence of a phase transfer catalyst such as polyethyleneglycol-750-monomethylether on polystyrene or hexadecyltrimethylammonium chloride at temperatures between 0° and 180° C., but preferably at temperatures between 10° and 160° C.

e) In order to prepare compounds of general formula I wherein $R_1$ represents one of the above-mentioned acyl or sulphonyl groups and A does not denote a lactam ring:

Acylation and sulphonation of a compound of general formula $$B—X_5—X_4—X_3—X_2—X_1—A_1—Y—E \quad (IX)$$

wherein $X_1$ to $X_5$, B, E and Y are as hereinbefore defined and $A_1$ denotes a 4-, 5-, 6- or 7-membered cyclic alkyleneimino group which is substituted by the groups $R_2$ and $R_3$, wherein in a 5- to 7-membered alkyleneimino group an ethylene group may be replaced by an ethenylene group, and which is unsubstituted in the 1-position, with a compound of general formula $$Z_4—R_1' \quad (X)$$

wherein $R_1'$ denotes the acyl or sulphonyl groups mentioned for $R_1$ hereinbefore and $Z_4$ denotes a hydroxy group, a leaving group such as a halogen atom, e.g. a chlorine or bromine atom, an azido group or an acyloxy group, e.g. an acetoxy, methoxycarbonyloxy, ethoxycarbonyloxy or isobutoxycarbonyloxy group, or $Z_4$ together with the hydrogen atom of an imino group adjacent to the carbonyl group denotes another carbon-nitrogen bond.

The reaction is conveniently carried out in a solvent such as methanol, methylene chloride, chloroform, carbon tetrachloride, ether, tetrahydrofuran, dioxane, benzene, toluene, acetonitrile, sulpholane or dimethylformamide, optionally in the presence of an inorganic or organic base, optionally in the presence of an acid-activating agent, optionally in the presence of a dehydrating agent or optionally an agent which activates the imino group, at temperatures between –20° and 200° C., preferably at between –10° and 160 ° C.

If $Z_4$ denotes a hydroxy group, the acylation is preferably carried out in a solvent such as tetrahydrofuran, methylene chloride, chloroform, sulpholane or dimethylformamide in the presence of an acid activating agent or a dehydrating agent, e.g. in the presence of ethylchloroformate, thionylchloride, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole, N,N'-carbonyldiimidazole or N,N'-thionyldiimidazole or triphenylphosphine/carbon tetrachloride, or an agent which activates the imino group, e.g. phosphorus trichloride, and optionally in the presence of a base such as sodium carbonate, potassium carbonate, potassium tert.butoxide or 1-hydroxy-benzotriazole/triethylamine or in the presence of a tertiary organic base such as 4-dimethylamino-pyridine, triethylamine, N-ethyldiisopropylamine, N-methyl-morpholine or pyridine, which may simultaneously serve as solvent, at temperatures between –10° and 100° C., but preferably at temperatures between 0° and 50° C.

However, the acylation or sulphonylation is preferably carried out with a corresponding acid halide or acid anhydride, optionally in the presence of an acid binding agent as described hereinbefore.

In order to prepare a corresponding aminocarbonyl compound the reaction of a compound of general formula IX is preferably carried out with an alkali metal cyanate such as sodium cyanate in water or in an alcohol/water mixture.

f) In order to prepare compounds of general formula I wherein B, B—$X_5$—$X_4$—$X_3$, B—$X_5$—$X_4$ or B—$X_5$ contains a guanidino group optionally substituted by a $C_{1-4}$-alkyl or by a benzyl group:

Reacting a compound of general formula $$B_2—X_5—X_4—X_3—X_2—X_1—A—Y—E \quad (XI)$$

wherein $X_1$ to $X_5$, A, E and Y are as hereinbefore defined and $B_2$, $B_2$—$X_5$—$X_4$—$X_3$, $B_2$—$X_5$—$X_4$ or $B_2$—$X_5$ contains an amino group or a cyclic alkyleneimino group, or the acid addition salts thereof with an amidine of general formula $$R_c—Z_5 \quad (XII)$$

wherein $R_c$ denotes an amidino group optionally substituted by $C_{1-4}$-alkyl groups or by a benzyl group and $Z_5$ denotes a cleavable group such as a 3,5-dimethylpyrazol- 1-yl, sulpho, methoxy, methylthio or ethylthio group, or with the acid addition salts thereof.

The reaction is expediently carried out in a solvent such as dimethylformamide, water, dimethylformamide/water, dioxane, dioxane/water, tetrahydrofuran or tetrahydrofuran/water, optionally in the presence of a tertiary organic base such as triethylamine or an inorganic base such as sodium carbonate at temperatures between 0° and 150° C., preferably at temperatures between 20° and 100° C.

g) In order to prepare compounds of general formula I wherein $X_2$ denotes an —$SO_2$—NH— group or a —CONH— group optionally substituted by an alkyl group at the nitrogen atom:

Reacting a compound of general formula $$B—X_5—X_4—X_3—E_2 \quad (XIII)$$

wherein $X_3$ to $X_5$ and B are as hereinbefore defined and $E_2$ denotes a carboxy or sulpho group, with a compound of general formula $$NHR_d—X_1—A—Y—E \quad (XIV)$$

wherein $X_1$, Y, A and E are as hereinbefore defined and $R_d$ denotes a hydrogen atom or a $C_{1-4}$-alkyl group, or with the reactive derivatives thereof.

The reaction is expediently carried out in a solvent such as tetrahydrofuran, methylene chloride, chloroform, acetonitrile, sulpholane or dimethylformamide or with mixtures thereof, preferably in the presence of an acid activating agent or a dehydrating agent, e.g. in the presence of isobutylchloroformate, thionylchloride, phosphorus trichloride, phosphorus pentoxide, N,N'-dicyclohexylcarbodiimide, N,N'-dicyclohexylcarbodiimide/N-hydroxysuccinimide or 1-hydroxybenzotriazole, N,N'-carbonyldiimidazole or N,N'-thionyldiimidazole or triphenylphosphine/carbon tetrachloride, or an agent which activates the amino group, e.g. phosphorus trichloride, and optionally in the presence of a base such as sodium carbonate, potassium carbonate or potassium tert.butoxide or in the presence of a tertiary organic base such as 4-dimethylamino-pyridine, triethylamine, N-ethyl-diisopropylamine, N-methylmorpholine or pyridine, which may simultaneously serve as solvent, at temperatures between −50° and 100° C., but preferably at temperatures between −30° and 50° C. However, the acylation or sulphonylation may also be carried out with a corresponding acid halide or acid anhydride, optionally in the presence of an acid binding agent and in the presence of an organic or inorganic base.

h) In order to prepare compounds of general formula I wherein E denotes a carboxy group, an alkoxycarbonyl group having a total of 2 to 7 carbon atoms or a phenylalkoxycarbonyl group optionally substituted by 1 or 2 methoxy groups at the phenyl ring:

Oxidation of a compound of general formula $$B-X_5-X_4-X_3-X_2-X_1-A-Y-E_3 \quad (XV)$$

wherein

A, B, $X_1$ to $X_5$ and Y are as hereinbefore defined and $E_3$ denotes a vinyl or 1,2-dihydroxyalkyl group, if necessary with subsequent esterification using a corresponding alcohol.

The oxidation is carried out in a solvent such as methylene chloride, acetonitrile, acetonitrile/water, methylene chloride/acetonitrile/water or carbon tetrachloride/acetonitrile/water in the presence of an oxidising agent such as potassium permanganate or ruthenium tetroxide, wherein the ruthenium tetroxide is preferably formed in the reaction mixture by reacting a ruthenium salt such as ruthenium trichloride with an oxidising agent such as sodium periodate, at temperatures between −10° and 60° C., preferably at temperatures between 0° and 50° C.

The optional subsequent esterification is conveniently carried out in a suitable solvent, e.g. in a corresponding alcohol, pyridine, toluene, methylene chloride, tetrahydrofuran or dioxane, in the presence of an acid activating and/or dehydrating agent such as hydrogen chloride, concentrated sulphuric acid, thionylchloride, ethylchloroformate, carbonyldiimidazole or N,N'-dicyclohexyl-carbodiimide or the isourea esters thereof, optionally in the presence of a reaction accelerator such as copper chloride, or by transesterification, e.g. with a corresponding carbonic acid diester, at temperatures between 0° and 100° C., but preferably at temperatures between 20° C. and the boiling temperature of the solvent in question.

i) In order to prepare compounds of general formula I wherein $R_1$ in the 1-position denotes a heteroaryl group and A is not a lactam ring:

Reacting a compound of general formula $$B-X_5-X_4-X_3-X_2-X_1-A_2-Y-E \quad (XVI)$$

wherein $X_1$ to $X_5$, B, E and Y are as hereinbefore defined and $A_2$ denotes a 4-, 5-, 6- or 7-membered cyclic alkyleneimino group substituted by the groups $R_2$ and $R_3$, wherein, in a 5- to 7-membered ring, an ethylene group may be replaced by an ethenylene group, and which is unsubstituted in the 1-position, with a compound of general formula $$Z_6-R_1'' \quad (XVII)$$

wherein $R_1''$ represents one of the heteroaryl groups mentioned for $R_1$ at the beginning and $Z_6$ denotes a nucleophilic leaving group such as a halogen atom, an alkylsulphenyl, alkylsulphinyl or alkylsulphonyl group, e.g. a chlorine or bromine atom or a methylsulphenyl, methylsulphinyl or methylsulphonyl group.

The reaction is optionally carried out in a solvent such as dioxane, tetrahydrofuran, acetonitrile, dimethylformamide, dimethylacetamide or dimethylsulphoxide, optionally in the presence of an inorganic base such as sodium carbonate or an organic base such as pyridine, triethylamine or N-ethyldiisopropylamine, which may simultaneously serve as solvent, at temperatures between 20° and 200° C., but preferably at temperatures between 60° and 160° C.

j) In order to prepare compounds of general formula I wherein B, $B-X_5-X_4-X_3$, $B-X_5-X_4$ or $B-X_5$ contains a guanidino group:

Reacting a compound of general formula $$B_3-X_5-X_4-X_3-X_2-X_1-A-Y-E \quad (XVIII)$$

wherein $X_1$ to $X_5$, A, E and Y are as hereinbefore defined and $B_3$, $B_3-X_5-X_4-X_3$, $B_3-X_5-X_4$ or $B_3-X_5$ contains an amino group or cyclic alkyleneimino group, or an acid addition salt thereof, with cyanamide.

The reaction is conveniently carried out in a solvent such as dioxane, dioxane/water, tetrahydrofuran or ethanol, preferably at temperatures between 60° and 120° C., e.g. at the boiling temperature of the reaction mixture.

k) In order to prepare compounds of general formula I wherein E denotes an alkoxycarbonyl group having a total of 2 to 7 carbon atoms which may be substituted in the alkyl moiety from position 2 by a morpholino or pyrrolidin-2-on-1-yl group, a phenylalkoxycarbonyl optionally substituted by one or two methoxy groups, a pyridinalkoxycarbonyl or $R_8O-CO-$ group:

Reacting a compound of general formula $$B-X_5-X_4-X_3-X_2-X_1-A-Y-E_4 \quad (XIX)$$

wherein

A, B, $X_1$ to $X_5$ and Y are as hereinbefore defined and $E_4$ denotes a carboxy group or the reactive derivatives thereof such as the esters, anhydrides or halides thereof, with a compound of general formula $$H-R_e \quad (XX)$$

wherein $R_e$ denotes an alkoxy group having 1 to 6 carbon atoms which may be substituted in the alkyl moiety from position 2 by a morpholino or pyrrolidin-2-on-1-yl group, a phenylalkoxy group optionally substituted by one or two methoxy groups, a pyridinylalkoxy or $R_8O$ group, wherein $R_8$ is defined as hereinbefore.

The reaction is expediently carried out in a solvent such as tetrahydrofuran, chloroform, methylene chloride, dimethylformamide or in a corresponding alcohol, optionally in the presence of an acid activating agent or a dehydrating agent, e.g. in the presence of isobutylchloroformate, thionylchloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole, N,N'-carbonyldiimidazole or N,N'-thionyldiimidazole or triphenylphosphine/carbon tetrachloride, and optionally in the presence of a base such as sodium carbonate, potassium carbonate, potassium tert.butoxide or 1-hydroxybenzotriazole/triethylamine or in the presence of a tertiary organic base such as triethylamine, N-ethyl-diisopropylamine, N-methylmorpholine or pyridine, which may simultaneously serve as solvent, at temperatures between −30° and 100° C., but preferably at temperatures between −10° and 80° C. However, the reaction may also be carried out with a corresponding acid halide or acid anhydride, optionally in the presence of an acid binding agent as described hereinbefore.

l) In order to prepare compounds of general formula I wherein $X_2$ denotes a —CONH— group optionally substituted at the nitrogen atom by a $C_{1-4}$-alkyl group and $X_3$ or $X_5$—$X_4$—$X_3$ contains a cyclic imino group, the ring nitrogen atom of which is linked to the carbonyl group of $X_2$:

Reacting a compound of general formula $$B—X_5—X_4—X_3—H \qquad (XXI)$$

wherein

B and $X_3$ to $X_5$ are as hereinbefore defined, with a compound of general formula $$NHR_d—X_1—A—Y—E \qquad (XXII)$$

wherein

A, E, $X_1$ and Y are as hereinbefore defined and $R_d$ denotes a hydrogen atom or a $C_{1-4}$-alkyl group, in the presence of a compound of general formula $$Z_7—CO—Z_8 \qquad (XXIII)$$

wherein $Z_7$ and $Z_8$, which may be identical or different, represent nucleophilic leaving groups such as halogen atoms or an N-azolyl group, e.g. a chlorine atom, an N-imidazolyl or N-(1,2,4-triazolyl) group.

The reaction is preferably carried out in the presence of phosgene or N,N'-carbonyldiimidazole, appropriately in a solvent such as tetrahydrofuran, dioxane, acetonitrile, methylene chloride or dimethylformamide in the presence of an organic base such as imidazole, triethylamine or pyridine, which may also serve as solvent, at temperatures between −20° and 60° C., preferably at temperatures between −10° and 30° C.

The reaction is, however, preferably carried out by reacting one of the compounds of general formula XXI or XXII with one of the above-mentioned compounds of general formula XXIII and then reacting it in the reaction mixture with the other compound of formula XXI or XXII.

m) In order to prepare compounds of general formula I wherein B contains an aminomethylene group:

Reducing a compound of general formula $$B_4—X_5—X_4—X_3—X_2—X_1—A—Y—E \qquad (XXIV)$$

wherein

A, E, $X_1$ to $X_5$ and Y are as hereinbefore defined and $B_4$ denotes one of the groups mentioned for B hereinbefore which contain a cyano group.

The reduction is preferably carried out in a suitable solvent such as methanol, methanol/water, methanol/water/ammonia, methanol/hydrochloric acid, ethanol, ether, tetrahydrofuran, dioxane or glacial acetic acid in the presence of catalytically activated hydrogen, e.g. hydrogen in the presence of Raney nickel, platinum or palladium/charcoal or in the presence of a metal hydride such as sodium borohydride, lithium borohydride or lithium aluminium hydride at temperatures between 0° and 100° C., preferably at temperatures between 20° and 80° C.

n) In order to prepare compounds of general formula I wherein $X_2$ denotes an optionally alkyl-substituted imino group and $X_3$ denotes one of the heteroarylene groups mentioned hereinbefore:

Reacting a compound of general formula $$B—X_5—X_4—X_3'—Z_9 \qquad (XXV)$$

wherein

B, $X_4$ and $X_5$ are as hereinbefore defined, $X_3'$ denotes one of the heteroarylene groups mentioned for $X_3$ hereinbefore and $Z_9$ denotes a nucleophilic leaving group such as a halogen atom, an alkylsulphenyl, alkylsulphinyl or alkylsulphonyl group, e.g. a chlorine or bromine atom or a methylsulphenyl, methylsulphinyl or methylsulphonyl group, with a compound of general formula $$NHR_d—X_1—A—Y—E \qquad (XXVI)$$

wherein

A, E, Y and $X_1$ are as hereinbefore defined and $R_d$ denotes a hydrogen atom or a $C_{1-4}$-alkyl group.

The reaction is conveniently carried out in a suitable solvent such as dimethylsulphoxide, dimethylformamide, dimethylacetamide, dioxane or toluene, optionally in the presence of an inorganic base such as sodium carbonate or sodium hydrogen carbonate or a tertiary organic base such as pyridine, triethylamine or N-ethyldiisopropylamine, which may simultaneously serve as solvent, at temperatures between 20° and 180° C., but preferably at temperatures between 60° and 140° C.

o) In order to prepare compounds of general formula I wherein $X_2$ denotes a bond, $X_3$ denotes one of the heteroarylene groups mentioned hereinbefore and $X_3$ is bound to $X_1$ by the cyclic nitrogen atom of a —CO—N— group:

Reacting a compound of general formula $$B—X_5—X_4—X_3''—H \qquad (XXVII)$$

wherein

B, $X_4$ and $X_5$ are as hereinbefore defined and $X_3''$ denotes one of the heteroarylene groups mentioned for $X_3$ hereinbefore, wherein one or two methine groups adjacent to a nitrogen atom are each replaced by a hydroxymethine group, or the tautomers thereof, with a compound of general formula $$Z_{10}—X_1—A—Y—E \qquad (XXVIII)$$

wherein

A, E, $X_1$ and Y are as hereinbefore defined and $Z_{10}$ denotes a nucleophilic leaving group such as a halogen atom or a sulphonyloxy group, e.g. a chlorine or bromine atom or a methanesulphonyloxy or p-toluenesulphonyloxy group.

The reaction is conveniently carried out in a suitable solvent such as dimethylformamide, dimethylacetamide, dimethylsulphoxide, N-methyl-pyrrolidone, tetrahydrofuran or dioxane, preferably in the presence of a base such as sodium hydride, potassium tert.butoxide, potassium carbonate or sodium hydrogen carbonate at temperatures between 0° and 160° C., preferably at temperatures between ambient temperature and 120° C.

p) In order to prepare compounds of general formula I wherein B, B—$X_5$—$X_4$—$X_3$, B—$X_5$—$X_4$ or B—$X_5$ contains an amino, cyclic alkyleneimino, amidino or guanidino group substituted by an alkoxycarbonyl group having a total of 2 to 5 carbon atoms or by a phenylalkoxycarbonyl or $R_4$—CO—O—($R_5$CH)—O—CO— group:

Reacting a compound of general formula

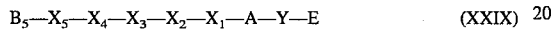   $B_5$—$X_5$—$X_4$—$X_3$—$X_2$—$X_1$—A—Y—E   (XXIX)

wherein

A, E, $X_1$ to $X_5$ and Y are as hereinbefore defined and $B_5$, $B_5$—$X_5$—$X_4$—$X_3$, $B_5$—$X_5$—$X_4$ or $B_5$—$X_5$ contains an amino, cyclic alkyleneimino, amidino or guanidino group, with a compound of general formula

   $Z_{11}$—$R_f$   (XXX)

wherein $R_f$ denotes an alkoxycarbonyl group having a total of 2 to 5 carbon atoms, a phenylalkoxycarbonyl or an $R_4$—CO—O—($R_5$CH)—O—CO— group wherein $R_4$ and $R_5$ are as hereinbefore defined, and $Z_{11}$ denotes a nucleophilic leaving group such as a halogen atom or an aryloxy group, e.g. a chlorine or bromine atom or a p-nitrophenoxy group.

The reaction is conveniently carried out in a solvent such as tetrahydrofuran, methylene chloride, chloroform, ethyl acetate or dimethylformamide, conveniently in the presence of a base such as sodium carbonate, potassium carbonate or sodium hydroxide solution or in the presence of a tertiary organic base such as triethylamine, N-ethyl-diisopropylamine, N-methylmorpholine or pyridine, which may simultaneously serve as solvent, at temperatures between –30° and 100° C., but preferably at temperatures between –10° and 60° C.

q) In order to prepare compounds of general formula I wherein E denotes an alkoxycarbonyl group having a total of 2 to 7 carbon atoms, a phenylalkoxycarbonyl group which may be substituted by one or two methoxy groups in the phenyl nucleus, or a pyridinealkoxycarbonyl, $R_6$—CO—O—($R_7$CH)—O—CO— or $R_8$O—CO— group:

Reacting a compound of general formula

   B—$X_5$—$X_4$—$X_3$—$X_2$—$X_1$—A—Y—COOH   (XXX)

wherein

A, B, $X_1$ to $X_5$ and Y are as hereinbefore defined, with a compound of general formula

   $Z_{11}$—$E_5$   (XXXII)

wherein $E_5$ denotes a $C_{1-6}$-alkyl group, a phenylalkyl group which may be substituted by one or two methoxy groups in the phenyl nucleus, a pyridylalkyl, $R_6$—CO—O— ($R_7$CH)— or $R_8$— group, wherein $R_6$ to $R_8$ are as hereinbefore defined, and $Z_{12}$ denotes a nucleophilic leaving group such as a halogen atom, e.g. a chlorine, bromine or iodine atom, or a methanesulphonyloxy or p-toluenesulphonyloxy group.

The reaction is conveniently carried out in a solvent such as methylene chloride, tetrahydrofuran, dioxane, dimethylsulphoxide or dimethylformamide, optionally in the presence of a reaction accelerator such as sodium or potassium iodide and preferably in the presence of a base such as sodium carbonate, potassium carbonate or sodium hydroxide solution or in the presence of a tertiary organic base such as N-ethyl-diisopropylamine or N-methyl-morpholine, which may simultaneously serve as solvent, or optionally in the presence of silver carbonate or silver oxide at temperatures between –30° and 100° C., but preferably at temperatures between –10° and 80° C.

r) In order to prepare compounds of general formula I wherein B denotes an amidino group substituted by an O,O'-dimethyl-phosphono or O,O'-diethyl-phosphono group:

Reacting a compound of general formula

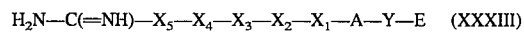   $H_2N$—C(=NH)—$X_5$—$X_4$—$X_3$—$X_2$—$X_1$—A—Y—E   (XXXIII)

wherein

A, E, $X_1$ to $X_5$ and Y are as hereinbefore defined, with a compound of general formula

   $(R_9O)_2PO$—$Z_{13}$   (XXXIV)

wherein $R_9$ denotes a methyl or ethyl group and $Z_{13}$ denotes a nucleophilic leaving group such as a cyano group or a halogen atom, e.g. a chlorine or bromine atom.

The reaction is conveniently carried out in a solvent or mixture of solvents such as tetrahydrofuran, methylene chloride, chloroform, ethyl acetate or dimethylformamide, expediently in the presence of an inorganic base such as sodium carbonate, potassium carbonate or sodium hydroxide solution or in the presence of a tertiary organic base such as triethylamine, N-ethyl-diisopropylamine, N-methylmorpholine or pyridine, which may simultaneously serve as solvent, at temperatures between –30° and 100° C., but preferably at temperatures between –10° C. and 60° C.

If according to the invention a compound of general formula I is obtained which contains a nitro group as substituent, this may be converted by reduction into a corresponding amino compound of general formula I, and/or if a compound of general formula I is obtained which contains a hydroxy, amino, alkylamino or imino group, this may be converted by acylation, sulphonylation or alkylation into a corresponding compound of general formula I, and/or if a compound of general formula I is obtained which contains a carbonyl bridge, this may be converted by reduction into a corresponding compound of general formula I which contains a methylene bridge, and/or if a compound of general formula I is obtained which contains an alkylsulphenyl, arylsulphenyl or thiomorpholino group or a thioether bridge, this may be converted by oxidation into a corresponding S-oxide compound of general formula I and/or if a compound of general formula I is obtained which contains an alkylsulphenyl, alkylsulphinyl, arylsulphenyl, arylsulphinyl, thiomorpholino or 1-oxidothiomorpholino group or a thioether bridge, this may be converted by oxidation into a corresponding S,S-dioxide compound of general formula I and/or if a compound of general formula I is obtained which contains an ester group this may be converted by transesterification into a corresponding ester and/or if a compound of general formula I is obtained which contains a pyridyl or an isoquinolinyl group, this may be converted by hydrogenation into a corresponding piperidinyl compound or a corresponding 1,2,3,4-tetrahydro-isoquinolinyl compound and/or if a compound of general formula I is obtained which contains a partially or fully saturated alkyleneimino group, this may be converted by alkylation into a corresponding N-alkyl-alkyleneimino compound.

The subsequent reduction of the nitro group is preferably carried out in a solvent such as water, water/ethanol, methanol, glacial acetic acid, ethyl acetate or dimethylformamide, usefully with hydrogen in the presence of a hydrogenation catalyst such as Raney nickel, platinum or palladium/charcoal, with metals such as iron, tin or zinc in the presence of an acid such as zinc/acetic acid or zinc/calcium chloride, with salts such as iron(II)sulphate, tin(II)chloride, sodium sulphide, sodium hydrogen sulphite or sodium dithionite, or with hydrazine in the presence of Raney nickel at temperatures between 0° and 100° C., but preferably at temperatures between 20° and 80° C.

The subsequent acylation or sulphonylation of an amino, alkylamino, imino or hydroxy group is conveniently carried out in a solvent such as methylene chloride, chloroform, carbon tetrachloride, ether, tetrahydrofuran, dioxane, benzene, toluene, acetonitrile or dimethylformamide, optionally in the presence of an acid activating agent or a dehydrating agent, e.g. in the presence of ethylchloroformate, thionylchloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, optionally in the presence of an inorganic base such as sodium carbonate or a tertiary organic base such as triethylamine, pyridine or 4-dimethylamino-pyridine, which may simultaneously be used as solvents, at temperatures between −25° and 150° C., but preferably at temperatures between −10° C. and the boiling temperature of the solvent used. However, the subsequent acylation or sulphonylation is carried out as described above, preferably with a corresponding acid halide or acid anhydride, and may also be carried out without a solvent.

The subsequent alkylation of a hydroxy, amino, alkylamino or imino compound is preferably carried out in a solvent or mixture of solvents such as methylene chloride, dimethylformamide, dimethylsulphoxide, benzene, chlorobenzene, tetrahydrofuran, benzene/tetrahydrofuran or dioxane in the presence of an alkylating agent such as methyliodide, methylbromide, ethylbromide, dimethylsulphate or benzylchloride, for example in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide or an alkali metal hydride such as sodium hydride, appropriately at temperatures between 0° and 150° C., preferably at temperatures between 0° and 50° C.

The subsequent alkylation of an amino or alkylamino compound may also be carried out by reductive amination in a suitable solvent such as methanol, ethanol, tetrahydrofuran, dioxane, acetonitrile or mixtures thereof with water in the presence of a suitable reducing agent such as a suitable complex metal hydride, but preferably in the presence of sodium cyanoborohydride, or with hydrogen in the presence of a hydrogenation catalyst such as palladium/charcoal at temperatures between 0° and 50° C., but preferably at ambient temperature.

The subsequent reduction of a carbonyl bridge is preferably carried out in a solvent such as methanol, ethanol or isopropanol, optionally in the presence of an acid such as hydrochloric or acetic acid with hydrogen in the presence of a catalyst such as platinum or palladium/charcoal at temperatures between 0° and 100° C., but preferably at temperatures between 20° C. and 80° C.

The subsequent oxidation of a thioether is preferably carried out in a solvent or mixture of solvents, e.g. in water, water/pyridine, acetone, glacial acetic acid, methylene chloride, glacial acetic acid/aceticanhydride, dilute sulphuric acid or trifluoroacetic acid, at temperatures between −80° and 100° C. depending on the oxidising agent used.

In order to prepare a corresponding S-oxide compound of general formula I oxidation is appropriately carried out with one equivalent of the oxidising agent used, e.g. with hydrogen peroxide in glacial acetic acid, trifluoroacetic acid or formic acid at 0° to 20° C. or in acetone at 0° to 60° C., with a peracid such as performic acid in glacial acetic acid or trifluoroacetic acid at 0° to 50° C. or with m-chloroperbenzoic acid in methylene chloride or chloroform at −20° to 60° C., with sodium metaperiodate in aqueous methanol or ethanol at −15° to 25° C., with bromine in glacial acetic acid or aqueous acetic acid, with N-bromo-succinimide in ethanol, with tert.butyl-hypochlorite in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphurylchloride in methylene chloride at −70° C. and the resulting thioetherchlorine complex is conveniently hydrolysed with aqueous ethanol.

In order to prepare an S,S-dioxide compound of general formula I, oxidation is expediently carried out with one or with two or more equivalents of the oxidising agent used, e.g. with hydrogen peroxide in glacial acetic acid/aceticanhydride, trifluoroacetic acid or in formic acid at 20° to 100° C. or in acetone at 0° to 60° C., with a peracid such as performic acid or m-chloroperbenzoic acid in glacial acetic acid, trifluoroacetic acid, methylene chloride or chloroform at temperatures between 0° and 60° C., with nitric acid in glacial acetic acid at 0 to 20° C., with chromic acid or potassium permanganate in glacial acetic acid, water/sulphuric acid or in acetone at 0° to 20° C.

The subsequent reaction of an ester group with an alcohol is preferably carried out in a corresponding alcohol as solvent, optionally in the presence of another solvent such as methylene chloride or ether, preferably in the presence of an acid such as hydrochloric acid at temperatures between 0° and 100° C., preferably at temperatures between 20° and 80° C.

The subsequent catalytic hydrogenation of a pyridyl or isoquinolinyl group is carried out with hydrogen in the presence of a catalyst such as palladium/charcoal or platinum dioxide in a solvent such as methanol, ethanol, dioxane, ethyl acetate or glacial acetic acid, optionally in the presence of an acid such as hydrochloric acid. However, the catalytic hydrogenation is preferably carried out in the presence of platinum dioxide and glacial acetic acid at temperatures between 0° and 50° C., preferably at ambient temperature, under a hydrogen pressure of 1 to 7 bar, preferably 1 to 4 bar.

The subsequent alkylation of an alkylene imino group is carried out preferably by reductive amination in a suitable solvent such as methanol, ethanol, tetrahydrofuran, dioxane, acetonitrile or in a mixture of the solvents with water in the presence of a suitable complex metal hydride, preferably in the presence of sodium cyano boronhydride or with hydrogen in the presence of a hydrogenation catalyst such as palladium/charcoal at temperatures between 0° and 50° C., but preferably at ambient temperature. However, the methylation is carried out preferably with formaldehyde/formic acid at the boiling temperature of the reaction mixture.

In the reactions described hereinbefore, any reactive groups present such as hydroxy, carboxy, phosphono, amidino, guanidino, amino or alkylamino groups may be protected during the reaction by means of conventional protecting groups which are cleaved again after the reaction.

For example, the protective group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group, the protecting group for an amidino or guanidino group may be the benzyloxycarbonyl group and for the guanidino group additionally the 4-methoxy-2,3,6-trimethylphenylsulphonyl group, the protecting group for a phosphono group may be a trimethylsilyl, methyl, ethyl or benzyl group, and the protecting group for an amino, alkylamino or imino group may be an acetyl, benzoyl, ethoxycarbonyl, tert.butoxycarbonyl, benzyloxycarbonyl, benzyl or methoxybenzyl group and for the amino group a phthalyl group may also be considered.

The optional subsequent cleaving of a protecting group may, for example, be carried out hydrolytically in an aqueous solvent, e.g. in water, methanol/water, isopropanol/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or by ether cleaving, e.g. in the presence of iodotrimethylsilane, at temperatures between 0° and 100° C., preferably at temperatures between 10° and 50° C.

However, a benzyl, methoxybenzyl or benzyloxy-carbonyl group may be cleaved hydrogenolytically, for example, using hydrogen in the presence of a catalyst such as palladium/charcoal in a solvent such as methanol, ethanol, dioxane, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably 3 to 5 bar.

A methoxybenzyl group may also be cleaved in the presence of an oxidising agent such as cerium(IV)ammonium nitrite in a solvent such as methylene chloride, acetonitrile or acetonitrile/water at temperatures between 0° and 50° C., but preferably at ambient temperature.

A tert.butyl or tert.butyloxycarbonyl group is preferably cleaved by treating with an acid such as trifluoroacetic or hydrochloric acid, optionally using a solvent such as methylene chloride, dioxane, ethyl acetate or ether.

The cleaving of only one alkyl group from an O,O'-dialkylphosphono group is preferably carried out using sodium iodide in a solvent such as acetone, ethylmethylketone, acetonitrile or dimethylformamide at temperatures between 40° and 150° C., but preferably at temperatures between 60° and 100° C.

The cleaving of both alkyl groups from an O,O'-dialkylphosphono group is carried out, for example, with iodotrimethylsilane, bromotrimethylsilane or chlorotrimethylsilane/sodium iodide in a solvent such as methylene chloride, chloroform or acetonitrile at temperatures between 0° C. and the boiling temperature of the reaction mixture, but preferably at temperatures between 20° and 60° C.

The cleaving of a phthalyl group is preferably carried out in the presence of hydrazine or a primary amine such as methylamine, ethylamine or n-butylamine in a solvent such as methanol, ethanol, isopropanol, toluene/water or dioxane at temperatures between 20° and 50° C.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one optically active carbon atom may be resolved into their enantiomers.

Thus, for example, the cis/trans mixtures obtained may be resolved by chromatography into the cis and trans isomers thereof and the compounds of general formula I which occur in racemate form may be separated by methods known per se (cf. Allinger N. L. and Eliel E. L. in "Topics in Stereochemistry", Vol 6, Wiley Interscience, 1971) into their optical antipodes and compounds of general formula I having at least 2 asymmetric carbon atoms may be separated on the basis of their physical-chemical differences using known methods, e.g. by chromatography and/or fractional crystallisation, into the diastereomers thereof which, if they occur in racemic form, may subsequently be separated into the enantiomers as mentioned above.

The separation of enantiomers is preferably effected by column separation on chiral phases or by recrystallisation from an optically active solvent or by reacting with an optically active substance which forms salts with the racemic compound, especially acids, and separation of the diastereomeric salt mixture thus obtained, e.g. on the basis of their different solubilities, whilst the free antipodes may be released from the pure diastereomeric salts by the action of suitable agents. Particularly common, optically active acids include, for example, the D- and L-forms of tartaric and dibenzoyltartaric acid, di-o-tolyl tartaric acid, malic acid, mandelic acid, camphorsulphonic acid, glutamic acid, aspartic acid or quinic acid.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid or maleic acid.

In addition, the new compounds of formula I thus obtained, if they contain a carboxyl group, may subsequently, if desired, be converted into the addition salts thereof with inorganic or organic bases, more particularly, for pharmaceutical use, into the physiologically acceptable addition salts thereof. Examples of suitable bases include sodium hydroxide, potassium hydroxide, cyclohexylamine, ethanolamine, diethanolamine and triethanolamine.

The compounds of formulae II to XXXIV used as starting materials are known from the literature in some cases or may be obtained by methods known from the literature (see the Examples).

As already mentioned, the new cyclic imino derivatives of general formula I and the compounds known from U.S. Pat. No. 3,364,221, namely 1-(2-carboxyethyl)-4-[3-(4-piperidinyl)propyl]piperidine, 1-(carboxymethyl)-4-[5-(4-piperidinyl)pentyl]piperidine, 1-(2-carboxyethyl)-4-[3-(2-piperidinyl)propyl]piperidine, 1-(2-carboxyethyl)-3-[3-(3- piperidinyl)propyl]piperidine and 1-(4-carboxybutyl)-4-[3-(4-piperidinyl)propyl]piperidine and the addition salts thereof, particularly the physiologically acceptable addition salts thereof with inorganic or organic acids or bases, have valuable properties. Thus, the compounds of general formula I, wherein B—$X_5$ denotes a pyridinyl group, or B—$X_5$—$X_4$—$X_3$ or B—$X_5$—$X_4$ denotes an isoquinolinyl group or B, B—$X_5$, B—$X_5$—$X_4$ or B—$X_5$—$X_4$—$X_3$ contains an optionally substituted amino or imino group or a group which can optionally be converted in vivo into an optionally substituted amino or imino group, e.g. an amino or imino group substituted by an alkoxycarbonyl group and Y-E contains a carboxyl, phosphono, O-alkyl-phosphono or 5-tetrazolyl group or a group which may be converted in vivo into a carboxyl, phosphono, O-alkyl-phosphono or tetrazolyl group, e.g. a carbonyl group substituted by an alkoxy group, have valuable pharmacological properties and in addition to having an inhibitory effect on inflammation and bone degradation, have, in particular, antithrombotic, antiaggregatory and tumour- or metastasis-inhibiting effects. The other compounds of general formula I are particularly valuable intermediate products for preparing the above-mentioned pharmacologically active compounds.

By way of example, the compounds of general formula I were investigated for their biological effects as follows:
1. Fibrinogen binding to human thrombocytes The blood obtained by puncturing an antecubital vein is anticoagulated with trisodium citrate (final concentration: 13 mM) and centrifuged for 10 minutes at 170×g. The supernatant platelet-rich plasma is poured onto a Sepharose 2B column (Pharmacia) and eluted with a solution of 90 mM common salt, 14 mM trisodium citrate, 5 mM glucose and 50 mM Tris(hydroxymethyl)aminomethane, adjusted to pH 7.4. The gel-filtered platelets (GFP) appearing before the plasma proteins are used for the binding experiments.

50 μl of a 60 mM calcium chloride solution, 50 μl of a 0.6 mM adenosine diphosphate solution, 100 μl of substance solution or solvent and 50 μl of fibrinogen solution (containing 3 μg of $^{125}$I fibrinogen) are added to 750 μl of GFP and incubated for 20 minutes at ambient temperature. The non-specific binding is determined in the presence of 3 mg/ml of cold fibrinogen.

900 μl of the incubated material are carefully pipetted onto 250 μl of silicon oil (AP 38: AR 20, 1:2 v/v, Wacker Chemie) in Eppendorf tubes and centrifuged for 2 minutes at 10,000×g. The aqueous supernatant and some of the oil are drawn off, the tips of the tubes are cut off together with the platelet pellet and the quantity of bound fibrinogen is determined in a gamma counter. The concentration of substance which brings about a 50% inhibition in fibrinogen binding is determined from a series of concentrations and is given as the $IC_{50}$ value.
2. Antithrombotic activity
Method The thrombocyte aggregation is measured using the Born and Cross method (J. Physiol. 170: 397 (1964)) in platelet-rich plasma taken from healthy volunteers. To inhibit coagulation the blood is mixed with 3.14% sodium citrate in a ratio by volume of 1:10.
Collagen-induced aggregation The pattern of the decrease in optical density of the platelet suspension is photometrically measured and recorded after the addition of aggregation-triggering substance. The rate of aggregation is concluded from the angle of inclination of the density curve. The point on the curve where there is maximum light transmittance is used to calculate the optical density.

The amount of collagen used is as small as possible but sufficient to produce an irreversible reaction curve. Standard commercial collagen produced by Hormonchemie of Munich is used. Before the addition of the collagen the plasma is incubated for 10 minutes with the substance at 37° C.

From the measurements obtained an $EC_{50}$ is determined graphically, indicating a 50% change in the optical density in terms of the inhibition of aggregation.

The Table which follows contains the results found:

| Substance (Example No.) | Fibrinogen-binding test $IC_{50}$[nM] | Inhibition of platelet aggregation $EC_{50}$[nM] |
| --- | --- | --- |
| 1 | 0.010 | 0.06 |
| 1 (3) | 0.042 | 0.10 |
| 4 (2) | 0.200 | 0.54 |
| 4 (3) | 0.160 | 38.00 |
| 4 (4) | 0.140 | 0.21 |
| 4 (6) | 0.031 | 0.16 |
| 4 (8) | 0.770 | 5.50 |
| 4 (11) | 0.032 | 0.10 |
| 4 (13) | 0.059 | 0.59 |
| 4 (15) | 0.590 | 3.00 |
| 4 (18) | 0.055 | 0.43 |
| 6 (3) | 13.000 | 2.50 |
| 11 | 0.270 | 0.89 |
| 12 (6) | 0.570 | 3.80 |

Moreover, the compound of Example 5, for example, inhibits the collagen-induced thrombocyte aggregation ex vivo in Rhesus monkeys for more than 8 hours after oral administration of 1 mg/kg.

The compounds according to the invention are well tolerated because after intravenous administration of 30 mg/kg of the compounds of Examples 1 and 4(18) to three mice, no animals died.

In the light of their inhibitory effect on cell-cell or cell-matrix interactions, the new cyclic imino derivatives of general formula I and the physiologically acceptable addition salts thereof are suitable for combating or preventing diseases in which smaller or greater cell aggregates occur or in which cell-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above the dosage is between 0.1 μg and 30 mg/kg of body weight, preferably 1 μg to 15 mg/kg of body weight, given in up to 4 doses per day. For this purpose the compounds of formula I produced according to the invention, optionally in conjunction with other active substances such as thromboxane receptor antagonists and thromboxane synthesis inhibitors or combinations thereof, serotonin antagonists, α-receptor antagonists, alkylnitrates such as glycerol trinitrate, phosphodiesterase inhibitors, prostacyclin and the analogues thereof, fibrinolytics such as tPA, prourokinase, urokinase, streptokinase, or anticoagulants such as heparin, dermatane sulphate, activated protein C, vitamin K antagonists, hirudine, inhibitors of thrombin or other activated clotting factors, may be incorporated together with one or more inert conventional carriers and/or diluents, e.g. corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

Example I 2-tert.Butyloxycarbonyl-5-isoindoline carboxylic acid 6.64 g of 5-isoindoline carboxylic acid hydrochloride in 80 ml of dioxane/water (2:1) are mixed with 70 ml of 1N sodium hydroxide solution and then with 8.72 g of di-tert.butylpyrocarbonate and the mixture is stirred for 3½ hours at ambient temperature. The reaction mixture is evaporated down to some extent, adjusted to pH 2 with saturated aqueous potassium hydrogen sulphate solution and extracted several times with ethyl acetate. The combined organic phases are washed with saturated saline solution, dried and concentrated by rotary evaporation. The crude product is dissolved in 400 ml of ethyl acetate and washed three times with 20 ml of water. The organic phase is stirred with magnesium sulphate and activated charcoal, then filtered and evaporated down.

Yield: 6.0 g (71% of theory),
Melting point: 175°–177° C. (decomp.)
$R_f$ value: 0.48 (silica gel; ethyl acetate)

The following compounds are obtained analogously:
(1) 3-tert.butyloxycarbonyl-1H-2,3,4,5-tetrahydro-3-benzazepine- 7-carboxylic acid
  Melting point: 142°–147° C.
  $R_f$ value: 0.60 (silica gel; cyclohexane/ethyl acetate=1:1)
  Calculated: C 65.96; H 7.27; N 4.81; Found: 65.98; 7.36; 4.95.
(2) 7-acetyl-2-tert.butyloxycarbonyl-1,2,4,5-tetrahydroisoquinoline
  $R_f$ value: 0.68 (silica gel; cyclohexane/ethyl acetate=1:1)
(3) 4-(1-tert.butyloxycarbonyl-4-piperidinyl)benzoic acid
  $R_f$ value: 0.34 (silica gel; methylene chloride/cyclohexane/methanol/conc. aqueous ammonia=68:15:15:2)
(4) 3-tert.butyloxycarbonyl-7-hydroxy-1H-2,3,4,5-tetrahydro- 3-benzazepine
  $R_f$ value: 0.60 (silica gel; methylene chloride/ethanol=15:1)
(5) 4-(1-tert.butyloxycarbonyl-4-piperidinyl)phenol
  $R_f$ value: 0.63 (silica gel; methylene chloride/ethanol=15:1)

Example II 4-(5-Cyano-2-pyridyl)phenol 3.4 g of 4-(5-cyano-2-pyridyl)anisole and 35 g of pyridine hydrochloride are stirred for 2½ hours at 180° C. After cooling the mixture is digested with water and the precipitate is suction filtered. The precipitate is dissolved in ethyl acetate, dried and concentration by evaporation.

Yield: 2.3 g (73% of theory),
Melting point: 172°–175° C.
$R_f$ value: 0.48 (silica gel; methylene chloride/ethyl acetate=9:1)

The following compounds are obtained analogously:
(1) 4-(2-cyano-5-pyridyl)phenol
  Melting point: 191°–193° C.
  $R_f$ value: 0.65 (silica gel; methylene chloride/ethyl acetate=9:1)
(2) 4-(5-cyano-2-pyrazinyl)phenol
  Melting point: 205°–209° C.
  $R_f$ value: 0.45 (silica gel; methylene chloride/ethyl acetate=9:1)
(3) 4-(5-cyano-2-thiazolyl)phenol
  Melting point: 218°–220° C.
  $R_f$ value: 0.44 (silica gel; methylene chloride/ethyl acetate=9:1)
(4) 6-(4-hydroxyphenyl)isoquinoline
  $R_f$ value: 0.50 (silica gel; ethyl acetate/cyclohexane=7:1)

Example III 4-(5-Cyano-2-pyridyl)anisole 9 g of 4-(5-bromo-2-pyridyl)anisole, 7.7 g of copper(I)cyanide and 45 ml of dry dimethylformamide are refluxed for 6 hours. After cooling the mixture is evaporated down and the residue is distributed between 180 ml of 6N hydrochloric acid and ethyl acetate. The organic phase is separated off, the aqueous phase is extracted twice with ethyl acetate and the combined organic phases are washed with water and dilute aqueous ammonia.

The organic phase is dried and evaporated down.
Yield: 4.4 g (62% of theory),
Melting point: 103°–105° C.
$R_f$ value: 0.44 (silica gel; methylene chloride)
Calculated: C 74.27; H 4.79; N 13.33; Found: 73.98; 4.58; 13.04.

The following compound is obtained analogously:
(1) 4-(5-cyano-2-pyrazinyl)anisole
  Melting point: 132°–134° C.
  $R_f$ value: 0.68 (silica gel; methylene chloride)

Example IV 4-(2-Cyano-5-pyridyl)anisole 1.75 g of 3-(4-methoxyphenyl)pyridine-N-oxide, 3.5 ml of trimethylsilylcyanide, 2.4 ml of triethylamine and 10 ml of acetonitrile are refluxed for 8 hours. After the addition of 2 ml of trimethylsilylcyanide the mixture is refluxed for a further 8 hours. After cooling, it is mixed with 3M sodium carbonate solution and extracted with methylene chloride. The organic phase is dried and evaporated down. The residue is purified by silica gel chromatography with cyclohexane/ethyl acetate (3:1).

Yield: 1.05 g (57% of theory),
Melting point: 120°–122° C.
$R_f$ value: 0.33 (silica gel; cyclohexane/ethyl acetate=4:1)
Calculated: C 74.27; H 4.79; N 13.33; Found: 74.51; 4.86; 13.28.

Example V 3-(4-Methoxyphenyl)pyridine-N-oxide 2.4 g of 3-(4-methoxyphenyl)pyridine, 10 ml of glacial acetic acid and 3 ml of 35% aqueous hydrogen peroxide are stirred for 4 hours at 60° C. and 5 hours at 100° C. After cooling, 10 ml of water are added and the mixture is evaporated down to half. After the addition of ice water the mixture is neutralised with sodium hydroxide solution and the precipitate is suction filtered. The filtrate is extracted with methylene chloride and the precipitate is taken up in methylene chloride. The combined methylene chloride solutions are dried and concentrated by rotary evaporation. After purifying over a silica gel column with ethyl acetate/methanol (4:1) 1.9 g (73% of theory) are left.

Melting point: 109°–110° C.

R$_f$ value: 0.70 (silica gel; ethyl acetate/methanol=4:1)

Calculated: C 71.62; H 5.51; N 6.96; Found: 71.30; 5.50; 6.85.

Example VI

2-Bromo-5-(4-methoxyphenyl)pyrazine 26.1 g of 5-(4-methoxyphenyl)-2(1H)pyrazinone and 140 g of phosphorusoxybromide are heated to 100° C. for 45 minutes. After cooling, the hardened mass is added in batches to ice and water, with stirring. After 30 minutes stirring the mixture is left to stand for 18 hours and the precipitate is suction filtered. The filtrate is extracted with methylene chloride and the precipitate is dissolved in methylene chloride extract. The methylene chloride solution is washed with sodium bicarbonate solution, dried, filtered over activated charcoal and evaporated down.

Yield: 23.5 g (69% of theory),

Melting point: 140°–141° C.

Example VII

5-Isoindoline carboxlic acid-hydrochloride 6.83 g of 2-acetyl-5-isoindoline carboxylic acid×0.2 H$_2$O are refluxed for 16 hours in 160 ml of semiconcentrated hydrochloric acid. The mixture is then cooled and evaporated to dryness. The crude product is used in Example I without any further purification.

R$_f$ value: 0.11 (silica gel; methylene chloride/methanol= 10:1)

The following compounds are obtained analogously:

(1) 1H-2,3,4,5-tetrahydro-3-benzazepine-7-carboxylic acid chloride

R$_f$ value: 0.09 (silica gel; 1,2-dichloroethane/isopropanol/methanol/conc. aqueous ammonia=63:15:15:7)

(2) 4-(4-piperidinyl)benzoic acid-hydrochloride

Melting point: >230° C.

(3) 7-hydroxy-1H-2,3,4,5-tetrahydro-3-benzazepine

R$_f$ value: 0.34 (silica gel; methylene chloride/cyclohexane/methanol/conc. aqueous ammonia=68:15:15:2)

(4) 4-(4-piperidinyl)phenol

R$_f$ value: 0.30 (silica gel; methylene chloride/methanol/conc. aqueous ammonia=4:1:0.25)

Example VIII

1-Amino-6-(4-hydroxyphenyl)isoquinoline 2.5 g of 1-amino-6-(4-benzyloxyphenyl)isoquinoline in 50 ml of dimethylformamide are hydrogenated with 2.5 g of palladium/activated charcoal (10% palladium) at ambient temperature and then at 50° C. under a hydrogen pressure of 3.4 bars for 3 hours. The catalyst is then removed by suction filtering, the mixture is evaporated to dryness and the residue is purified by chromatography over a silica gel column with methylene chloride/methanol (4:1).

Yield: 0.5 g (28% of theory),

R$_f$ value: 0.20 (silica gel; methylene chloride/methanol= 4:1)

The following compounds are obtained analogously:

(1) 4-[(2-benzylamino-4-pyridyl)aminocarbonyl]phenol

R$_f$ value: 0.26 (silica gel; methylene chloride/methanol= 9:1) and 4-[(2-benzylamino-6-chloro-4-pyridyl)aminocarbonyl]phenol R$_f$ value: 0.58 (silica gel; methylene chloride/methanol= 9:1) by hydrogenation of 4-[(2-benzylamino-6-chloro-4-pyridyl)aminocarbonyl]-1-benzyloxy-benzene at ambient temperature.

Example IX

1-Amino-6-(4-benzyloxyphenyl)isoquinoline 7.1 g of sodium amide and 10.8 g of 6-(4-benzyloxyphenyl)-isoquinoline are added to 26.2 ml of N,N,N',N'-tetramethylethylenediamine and 30 ml of dry xylene and the mixture is stirred for 18 hours at 120° C. It is then cooled to 0° C. and 20 ml of ice water are carefully added dropwise. The mixture is evaporated to dryness and the residue is decocted with 150 ml of methanol. After cooling, the precipitate is suction filtered and dried.

Yield: 4.6 g (41% of theory),

R$_f$ value: 0.17 (silica gel; methylene chloride/methanol= 10:1)

Example X 6-(4-Benzyloxyphenyl)isoquinoline 13.3 g of 6-trifluoromethylsulphonyloxy-isoquinoline, 15.1 g of 4-benzyloxyphenylboronic acid anhydride, 2.8 g of tetrakistriphenylphosphine palladium, 72 ml of 2M aqueous sodium carbonate solution and 150 ml of 1,2-dimethoxyethane are refluxed for 24 hours under nitrogen. After cooling, 200 ml of water are added, the precipitate is suction filtered, washed with water and dried. After purification over a silica gel column with methylene chloride/methanol (20:1), 11.8 g (79% of theory) are obtained.

Melting point: 167°–168° C.

R$_f$ value: 0.48 (silica gel; methylene chloride/methanol= 20:1)

Calculated: C 84.86; H 5.50; N 4.50; Found: 84.78; 5.52; 4.42.

The following compound is obtained analogously:

(1) 6-(4-methoxyphenyl)isoquinoline

R$_f$ value: 0.57 (silical gel; ethyl acetate/cyclohexane=7:1)

Example XI 4-Benzyloxyphenylboronic acid anhydride

At −70° C. a Grignard solution prepared from 55.5 g of 4-benzyloxybromobenzene and 5.3 g of magnesium in 300 ml of tetrahydrofuran/toluene (4:1) is added dropwise within 45 minutes to a solution of 80 g of triisopropylborate in 300 ml of tetrahydrofuran/toluene (1:1). The mixture is slowly heated to ambient temperature overnight and then added to a mixture of 200 g of ice and 100 ml of conc. hydrochloric acid. After one hour's stirring the organic phase is separated and the aqueous phase is extracted five times with a total of 1 liter of methylene chloride/methanol (9:1). The combined organic phases are dried and evaporated down and the residue is purified by chromatography over silica gel with methylene chloride/ethyl acetate (4:1) and methylene chloride/methanol (4:1).

Yield: 19.1 g (43.1% of theory),

Melting point: 199°–201° C.

R$_f$ value: 0.28 (silica gel; methylene chloride/ethyl acetate=4:1)

Calculated: C 74.34; H 5.28; Found: 74.32; 5.31.

Example XII

6-Trifluoroethylsulphonyloxy-isoquinoline 10 g of 6-hydroxyisoquinoline are dissolved in 150 ml of dry pyridine at 50° C. and cooled to −20° C. Then 11.6 ml of trifluoromethanesulphonic acid anhydride are added dropwise within 15 minutes with vigorous stirring. The mixture is stirred for a further 30 minutes at −20° C. and then for 16 hours at 0° C. The reaction mixture is evaporated down and the residue is evaporated several times with toluene. The residue is taken up in 250 ml of tert.butyl-methylether and extracted five times with 20 ml of water. The organic phase is separated off, dried and evaporated down and the residue is purified by chromatography over a silica gel column using ethyl acetate.

Yield: 15.9 g (84% of theory),
$R_f$ value: 0.76 (silica gel; ethyl acetate/cyclohexane=9:1)
Calculated: C 43.33; H 2.18; N 5.05; S 11.56; Found: 43.29; 2.35; 5.15; 11.62.

Example XIII

2-Acetyl-5-isoindoline carboxylic acid×0.2 $H_2O$ 1.76 g of 2,5-diacetylisoindoline are suspended in a solution of 5.2 g of sodium hydroxide in 50 ml of water. At 10° C. 1.4 ml of bromine are added dropwise within 20 minutes with vigorous stirring. The reaction mixture is stirred for 20 minutes at 10° C. and 15 minutes at 20° C. Then 100 ml of water are added, the precipitated bromoform is separated off and the aqueous phase is extracted with methylene chloride. The aqueous phase is mixed with a little sodium disulphite and then acidified with 10 ml of concentrated hydrochloric acid whilst cooling with ice. The precipitate is suction filtered and washed with ice water. The crude product is stirred for 4 hours with 2N hydrochloric acid, suction filtered, washed with water and dried in vacuo at 80° C.

Yield: 1.1 g (65% of theory),
Melting point: >220° C.
$R_f$ value: 0.38 (silica gel; ethyl acetate/methanol=10:1)
Calculated: C 63.27; H 5.50; N 6.71; Found: 63.20; 5.22; 6.67.

The following compounds are obtained analogously:
(1) 3-acetyl-1H-2,3,4,5-tetrahydro-3-benzazepine-7-carboxylic acid
$R_f$ value: 0.20 (silica gel; 1,2-dichloroethane/isopropanol/methanol/conc. aqueous ammonia=63:15:15:7)
(2) 2-tert.butyloxycarbonyl-1,2,3,4-tetrahydroisoquinoline-7-carboxylic acid
$R_f$ value: 0.65 (silica gel; cyclohexane/ethyl acetate=1:1)
(3) 4-(1-acetyl-4-piperidinyl)benzoic acid
$R_f$ value: 0.25 (silica gel; methylene chloride/cyclohexane/methanol/conc. aqueous ammonia=68:15:15:2)

Example XIV 2,5-Diacetylisoindoline 5.0 g of 2-acetylisoindoline in 10 ml of methylene chloride are added dropwise to 10.3 g of aluminium trichloride in 30 ml of methylene chloride at ambient temperature. After 16 hours' stirring at ambient temperature the reaction mixture is poured onto a mixture of 100 g of ice and 20 ml of concentrated hydrochloric acid with vigorous stirring. The organic phase is separated off and the aqueous phase is extracted four times with 50 ml of methylene chloride. The combined organic phases are washed with saturated aqueous saline solution, dried and evaporated down. The crude product is purified by chromatography over a silica gel column with ethyl acetate/methanol (15:1).

Yield: 1.9 g (30% of theory),
Melting point: 136°–140° C.
$R_f$ value: 0.40 (silica gel; ethyl acetate/methanol=10:1)
Calculated: C 70.92; H 6.45; N 6.89; Found: 71.12; 6.56; 6.90.

The following compounds are obtained analogously:
(1) 3,7-diacetyl-1H-2,3,4,5-tetrahydro-3-benzazepine
$R_f$ value: 0.50 (silica gel; methylene chloride/ethanol=15:1)
(2) 4-(1-acetyl-4-piperidinyl)acetophenone
$R_f$ value: 0.44 (silica gel; methylene chloride/ethanol=15:1)

Example XV (3R,5S)-3-Allyl-5-[(4'-cyano-4-biphenylyl)oxymethyl]-1-(2-pyridyl)-2-pyrrolidinone 6.3 g of (3R,5S)-3-allyl-5-[(4'-cyano-4-biphenylyl)oxymethyl]-2-pyrrolidinone, 4.0 g of 2-bromopyridine, 5.5 g of potassium carbonate, 1.3 g of tris-[2-(2-methoxyethoxy)ethyl]amine and 0.3 g each of copper(I)chloride and copper(I)iodide are refluxed in 100 ml of xylene under nitrogen for 5 hours. After cooling, the mixture is diluted with ethyl acetate and filtered and the filtrate is washed with water, dilute sodium hydrogen sulphite solution, water and saturated saline solution, dried and evaporated down. The crude product is purified by chromatography over a silica gel column using cyclohexane/ethyl acetate (85:15).

Yield: 6.3 g (81% of theory),
Melting point: 107°–109° C.
$R_f$ value: 0.41 (silica gel; cyclohexane/ethyl acetate=8:2)
Calculated: C 76.26; H 5.66; N 10.26; Found: 75.80; 5.68; 10.09.

The following compound is obtained analogously:
(1) (3R,5S)-3-allyl-5-[(4'-cyano-4biphenylyl)oxymethyl]-1-(3-pyridyl)-2-pyrrolidinone
Melting point: 118°–121° C.
$R_f$ value: 0.41 (silica gel; cyclohexane/ethyl acetate=2:8)
Calculated: C 76.26; H 5.66; N 10.26; Found: 75.90; 5.73; 10.00.

Example XVI

7-Cyano-1H-2,3,4,5-tetrahydro-3-benzazepine 80 ml of trifluoroacetic acid in 80 ml of methylene chloride are added dropwise to 10.9 g of 3-tert.butyloxycarbonyl- 7-cyano-1H-2,3,4,5-tetrahydro-3-benzazepine in 80 ml of methylene chloride. After 15 minutes the mixture is evaporated down, the residue is distributed between 1N potassium carbonate solution and methylene chloride and the organic phase is washed with water, dried and evaporated down.

Yield: 5.9 g (85% of theory),
$R_f$ value: 0.67 (silica gel; methanol/conc. aqueous ammonia=9:1)
The following compound is obtained analogously:
(1) 7-cyano-1,2,3,4-tetrahydroisoquinoline
$R_f$ value: 0.40 (silica gel; methanol)
Calculated: C 75.92; H 6.37; N 17.71; Found: 75.43; 6.53; 17.45.

Example XVII 3-tert.Butyloxycarbonyl-7-cyano-1H-2,3,4,5-tetrahydro-3-benzazepine 17 g of 3-tert.butyloxycarbonyl-1H-2,3,4,5-tetrahydro-3-benzazepine- 7-carboxylic acid amide, 19.2 g of triphenylphosphine, 5.9 ml of carbon tetrachloride, 8.2 ml of triethylamine and 90 ml of chloroform are stirred for 9 hours at 60° C. The reaction mixture is washed with water, dried and evaporated down. The residue is purified by chromatography over a silica gel column using cyclohexane/ethyl acetate (1:1).

Yield: 10.9 g (68% of theory),
$R_f$ value: 0.77 (silica gel; cyclohexane/ethyl acetate=1:1)

The following compound is obtained analogously:
(1) 2-tert.butyloxycarbonyl-7-cyano-1,2,3,4-tetrahydroisoquinoline $R_f$ value: 0.82 (silica gel; cyclohexane/ethyl acetate=1:1)

Example XVIII 3-tert.Butyloxycarbonyl-1H-2,3,4,5-tetrahydro-3-benzazepine- 7-carboxylic acid amide At 0° C. 15 g of N,N'-dicyclohexylcarbodiimide are added to a solution of 19.3 g of 3-tert.butyloxycarbonyl-1H-2,3,4,5-tetrahydro-3-benzazepine-7-carboxylic acid and 10.8 g of 1-hydroxy-1H-benzotriazole in 350 ml of tetrahydrofuran and the mixture is stirred for 15 minutes at 0° C. and 45 minutes after removal of the ice bath. At 10° C. 6.7 ml of conc. aqueous ammonia are added and the mixture is stirred for 2½ hours at ambient temperature. The precipitate is removed by suction filtering and the filtrate is evaporated down. The residue is distributed between ethyl acetate and water, the organic phase is separated off, dried and evaporated down. The residue is stirred with diisopropylether and the solid matter is suction filtered. The solid substance is purified by chromatography over a silica gel column using ethyl acetate.

Yield: 15.5 g (81% of theory),
Melting point: 173°–174° C.
$R_f$ value: 0.53 (silica gel; ethyl acetate)
Calculated: C 66.18; H 7.64; N 9.65; Found: 66.42; 7.81; 9.77.

The following compound is obtained analogously:
(1) 2-tert.butyloxycarbonyl-1,2,3,4-tetrahydroisoquinoline-7-carboxylic acid amide $R_f$ value: 0.52 (silica gel; ethyl acetate)

Example XIX (3R,5S)-3-Allyl-5-[[(3-tert.butyloxycarbonyl-1H-2,3,4,5-tetrahydro- 3-benzazepine-7-yl)carbonylamino]methyl]-1-(3-phenylpropyl)-2-pyrrolidinone 3.4 g of carbonyldiimidazole are added to 4.4 g of 3-tert-butyloxycarbonyl- 1H-2,3,4,5-tetrahydro-3-benzazepine- 7-yl carboxylic acid in 30 ml of dry tetrahydrofuran and the mixture is stirred for one hour with gentle heating. Then 4.1 g of (3R,5S)-3-allyl-5-aminomethyl- 1-(3-phenylpropyl)-2-pyrrolidinone in 10 ml of tetrahydrofuran are added dropwise and the mixture is stirred for 16 hours at ambient temperature. 100 ml of 1N hydrochloric acid are added and the mixture is extracted with ethyl acetate. The combined organic phases are washed with water and sodium hydrogen carbonate solution, dried, filtered over activated charcoal and some silica gel and evaporated down.

Yield: 6.6 g (80% of theory),
$R_f$ value: 0.37 (silica gel; ethyl acetate/cyclohexane=2:1)
The following compound is obtained analogously:
(1) (3R,5S)-3-allyl-5-[[[(1-tert.butyloxycarbonyl-4-piperidinyl)phenyl] carbonylamino]methyl]-1-(3-phenylpropyl)- 2 -pyrrolidinone $R_f$ value: 0.30 (silica gel; ethyl acetate/cyclohexane=2:1)

Example XX (3R,5S)-3-Allyl-5-[(3-tert.butyloxycarbonyl-1H-2,3,4,5-tetrahydro- 3-benzazepine-7-yl)oxymethyl]-1-(3-phenylpropyl)- 2-pyrrolidinone 5.1 g of 3-tert.butyloxycarbonyl-7-hydroxy-1H-2,3,4,5-tetrahydro- 3-benzazepine in 80 ml of dimethylformamide are stirred with 8.2 g of caesium carbonate for half an hour at 55° C. Then 6.8 g of (3R,5S)-3-allyl-5-[(methanesulphonyloxy)methyl]-1-(3-phenylpropyl)-2-pyrrolidinone in 40 ml of dimethylformamide are added dropwise and the mixture is stirred for 16 hours at 55° C. The reaction mixture is added to water and extracted with ethyl acetate. The combined organic phases are washed with water and saturated saline solution, dried, filtered over activated charcoal and evaporated down. The residue is purified by chromatography over silica gel using cyclohexane/ethyl acetate (2:1).

Yield: 7.5 g (77% of theory),
$R_f$ value: 0.36 (silica gel; cyclohexane/ethyl acetate=2:1)
The following compound is obtained analogously:
(1) (3R,5S)-3-allyl-5-[[4-(1-tert.butyloxycarbonyl-4-piperidinyl )phenyl]oxymethyl]-1-(3-phenylpropyl)-2-pyrrolidinone $R_f$ value: 0.39 (silica gel; cyclohexane/ethyl acetate=2:1)

Example XXI

3-Acetyl-7-hydroxy-1H-2,3,4,5-tetrahydro-3-benzazepine 11.9 g of 7-acetoxy-3-acetyl-1H-2,3,4,5-tetrahydro-3-benzazepine and 9 g of potassium carbonate are refluxed in 100 ml of methanol for one hour. The mixture is suction filtered and the filtrate is evaporated down. The residue is distributed between ethyl acetate and dilute hydrochloric acid. The organic phase is separated off, dried, filtered through activated charcoal and a little silica gel and the filtrate is evaporated down. The residue is triturated with a little methylene chloride, suction filtered and dried.

Yield: 5.0 g (51% of theory)
$R_f$ value: 0.41 (silica gel; methylene chloride/ethanol= 15:1)
The following compound is obtained analogously:
(1) 4-(1-acetyl-4-piperidinyl)phenol $R_f$ value: 0.40 (silica gel; methylene chloride/ethanol= 15:1)

Example XXII

7-Acetoxy-3-acetyl-1H-2,3,4,5-tetrahydro-3-benzazepine 11.5 g of 3,7-diacetyl-1H-2,3,4,5-tetrahydro-3-benzazepine, 17 g of m-chloroperbenzoic acid and 100 ml of chloroform are stirred for 4 days at ambient temperature in the dark. The precipitate is suction filtered, the precipitate is washed with methylene chloride and the entire filtrate is diluted with methylene chloride then extracted twice with sodium hydrogen sulphite solution, twice with sodium hydrogen carbonate solution and once with saturated saline solution, then dried and evaporated down.

Yield: 11.9 g (97% of theory),
$R_f$ value: 0.50 (silica gel; methylene chloride/ethanol= 15:1)
The following compound is obtained analogously:
(1) 1-acetyl-4-(4-acetoxyphenyl)-piperidine $R_f$ value: 0.44 (silica gel; methylene chloride/ethanol= 15:1)

Example XXIII (3R,5S)-3-Allyl-5-[[6-(4-cyanophenyl)-3-pyridazinyl] oxymethyl]- 1-(3-phenylpropyl)-2-pyrrolidinone 3.8 g of (3R,5S)-3-allyl-5-hydroxymethyl-1-(3-phenylpropyl)- 2-pyrrolidinone in 30 ml of dimethylformamide are mixed with 0.65 g of sodium hydride (55% dispersion in paraffin oil) and stirred for 10 minutes at ambient temperature. Then 3.0 g of 3-chloro- 6-(4-cyanophenyl)pyridazine are added in batches and the mixture is stirred for one hour at ambient temperature. The reaction mixture is stirred into water, some common salt is added and the mixture is then extracted with ethyl acetate. The organic phase is washed with water, dried, filtered and evaporated down. After chromatography over a silica gel column using cyclohexane/ethyl acetate (2:1; addition of 5% methanol) 3.3 g are left (52% of theory).

$R_f$ value: 0.31 (silica gel; methylene chloride/methanol= 50:1)

Example XXIV (3R,5S)-3-Allyl-5-[[6-(4-cyanophenyl)-3-pyridazinyl]aminomethyl]- 1-(3-phenylpropyl)-2-pyrrolidinone 6.2 g of (3R,5S)-3-allyl-5-aminomethyl]-2-pyrrolidinone, 4.9 g of 3-chloro-6-(4-cyanophenyl)pyridazine, 3.2 g of sodium carbonate and 50 ml of dimethylsulphoxide are stirred for 5 hours at 160° C., cooled, added to an aqueous saline solution and extracted with ethyl acetate. The organic phase is washed with water, dried, filtered and evaporated down. After purification over a silica gel column with methylene chloride/methanol (15:1) 4.2 g are left (41% of theory).

$R_f$ value: 0.33 (silica gel; methylene chloride/methanol= 15:1)

Example XXV

3-[(4-Cyanophenyl)aminocarbonyl]-2(1H)-pyridone 84 g of 2-chloro-3-[(4-cyanophenyl)aminocarbonyl]pyridine, 1 liter of glacial acetic acid and 111 g of sodium acetate-trihydrate are stirred for 48 hours at 130° C. Then the mixture is evaporated down and the residue is added to 1 liter of water. The precipitate is suction filtered, washed several times with water, acetone and diethylether and dried.

Yield: 74 g (95% of theory),
Melting point: 320°–322° C.
Calculated: C 65.27; H 3.79; N 17.56; Found: 65.25; 3.89; 17.55.

The starting material (melting point: 198°–201° C.) is obtained by reacting 2-chloro-nicotinic acid chloride with 4-aminobenzonitrile in the presence of triethylamine.

The following compounds are obtained analogously:
(1) 5-[(4-cyanophenyl)aminocarbonyl]-2(1H)-pyridone
Melting point: 330°–332° C.

The starting material (melting point: 216°–218° C.) is obtained by reacting 6-chloro-nicotinic acid chloride with 4-aminobenzonitrile in the presence of triethylamine.
(2) 5-[(4-cyanophenyl)aminocarbonyl]-2,4(1H,3H)-pyrimidine-dione
Melting point: >330° C.

The starting material (melting point: 162°–164° C.) is obtained by reacting 2,4-dichloro-pyrimidine-5-carboxylic acid chloride and 4-aminobenzonitrile in the presence of triethylamine.

Example XXVI

4-[(2-Benzylamino-6-chloro-4-pyridyl)aminocarbonyl]-1-benzyloxybenzene

The acid chloride obtained from 2.4 g of 4-benzyloxybenzoic acid with thionylchloride is refluxed for a total of 7 hours with 50 ml of methylene chloride, 2.5 g of 4-amino-2-benzylamino-6-chloro-pyridine, 1.5 ml of triethylamine and 0.5 g of 4-dimethylaminopyridine and then stirred for 2½ days at ambient temperature. The mixture is cooled and the crystals are suction filtered.

Yield: 3.4 g (73% of theory)
$R_f$ value: 0.56 (silica gel; diethylether/petroleum ether= 7:3)

Example XXVII

4-Amino-2-benzylamino-6-chloro-pyridine 23.5 g of 2-benzylamino-6-chloro-4-nitro-pyridine-N-oxide in 1.5 liters of tetrahydrofuran are hydrogenated with 2 g of Raney nickel for 12 hours at 40° C. under a hydrogen pressure of 5 bars. The filtration of the mixture yields filtrate 1. The residue is hydrogenated with 2 g of Raney nickel in tetrahydrofuran/dimethylformamide for a further 5 hours at 40° C. The mixture is filtered, the filtrate is evaporated down and the residue is triturated with methylene chloride/methanol (50:1). The solid substance is suction filtered and discarded and the mother liquor is evaporated down together with filtrate 1. Purification of the residue by repeated chromatography over a silica gel column using methylene chloride/methanol (50:1) and crystallisation from methylene chloride yields 5.4 g (28% of theory).

$R_f$ value: 0.68 (silica gel; methylene chloride/methanol= 19:1)

Example XXVIII

2-Benzylamino-6-chloro-4-nitro-pyridine-N-oxide 18.5 g of 2,6-dichloro-4-nitro-pyridine-N-oxide, suspended in 100 ml of ethanol, are mixed with 18.6 ml of benzylamine at ambient temperature and then refluxed for 3 hours. After cooling, the precipitate is suction filtered and washed with ethanol and diethylether.

Yield: 23.7 g (95% of theory)
$R_f$ value: 0.41 (silica gel; methylene chloride/methanol= 19:1)

Example XXIX 4-(5-Cyano-2-thiazolyl)anisole

At −30° C. a mixture of 42 ml of chloroacetonitrile and 54 ml of ethyl formate in 200 ml of tert.butylmethylether is added dropwise to 74.4 g of potassium tert.butoxide in 600 ml of tert.butylmethylether and 200 ml of dry ethanol. Then the mixture is stirred for 2½ days at ambient temperature. 9.1 g of 4-methoxythiobenzamide and 400 ml of dry ethanol are added to the resulting suspension and this is refluxed for 3 hours. The reaction mixture is evaporated down, mixed with water and extracted with ethyl acetate. The organic phase is separated off, dried and evaporated down. The residue is purified by chromatography over a silica gel column using methylene chloride. The product fractions are evaporated down, the residue is triturated with tert.butylmethylether and the crystals are suction filtered and dried.

Yield: 1.06 g (9% of theory, based on 4-methoxythiobenzamide),
Melting point: 141°–142° C.
$R_f$ value: 0.56 (silica gel; toluene/ethyl acetate=19:1)
Calculated: C 61.09; H 3.72; N 12.96; S 14.83; Found: 61.18; 3.79; 13.23; 14.61.

Example XXX 3-(4-Cyanobenzoyl)-2-hydroxy-propionic acid 25 g of 4-cyanoacetophenone and 24 g of glyoxylic acid monohydrate are stirred for 5 hours at 95° C. in a water jet vacuum. A viscous oil is obtained which is dissolved in a mixture of saturated sodium hydrogen carbonate solution and ethyl acetate. The organic phase is separated off, the aqueous phase is acidified with 2N hydrochloric acid and extracted several times with ethyl acetate. The combined ethyl acetate phases are washed with water, dried and evaporated down. The residue is triturated with diethylether, suction filtered and further reacted as a crude product.

Yield: 18.2 g (48% of theory), $R_f$ value: 0.25 (silica gel; methylene chloride/methanol/ethyl acetate=8:2:0.2)

Example XXXI 6-(4-Cyanophenyl)-2H-pyridazin-3-one 19.2 g of 3-(4-cyanobenzoyl)-2-hydroxy-propionic acid and 20 ml of 80% hydrazine solution in 200 ml of glacial acetic acid are refluxed for 2 hours. The mixture is left to cool, the precipitate is removed by suction filtering and washed with acetic acid and diethylether.

Yield: 10.3 g (60% of theory)

$R_f$ value: 0.32 (silica gel; methylene chloride/methanol= 19:1)

Example XXXII

3-Chloro-6-(4-cyanophenyl)pyridazine

A suspension of 27.6 g of 6-(4-cyanophenyl)-2H-pyridazin- 3-one in 200 ml of phosphorusoxychloride is refluxed for 2 hours. The reaction solution is stirred into 1 liter of water, the precipitate is suction filtered, washed with water and dried.

Yield: 25.7 g (85% of theory), $R_f$ value: 0.75 (silica gel; methylene chloride/methanol= 19:1)

Example XXXIII

Diethyl [2-(4-bromophenyl)-2-oxo-ethyl]malonate 124 g of potassium tert.butoxide are added to a solution of 165 ml of diethylmalonate in 600 ml of dimethylformamide. 307 g of 4-bromophenacylbromide are added in batches whilst cooling in a water bath, whereupon the reaction solution heats up to about 70° C. The mixture is stirred for 2 hours at ambient temperature, the reaction solution is poured into dilute saline solution and extracted with ethyl acetate. The organic phase is washed with water, dried over sodium sulphate and filtered over activated charcoal. After the solvent has been removed using a rotary evaporator 398 g of a red oil are obtained which is further reacted without being purified.

$R_f$ value: 0.40 (silica gel; cyclohexane/ethyl acetate=5:1)

Example XXXIV 6-(4-Bromophenyl)-4,5-dihydro-4-ethoxycarbonyl-2H-pyridazin- 3-one 240 ml of 80% hydrazine hydrate solution are added to a solution of 398 g of diethyl [2-(4-bromophenyl)-2-oxoethyl] malonate in 1.5 liter of glacial acetic acid and the mixture is refluxed for 2 hours. When the reaction solution cools a precipitate is formed which is suction filtered, washed with water and dried. To isolate further product, the mother liquor is mixed with water, the precipitate is suction filtered and recrystallised from glacial acetic acid.

Yield: 213 g (61% of theory), $R_f$ value: 0.31 (silica gel; cyclohexane/ethyl acetate=2:)

Example XXXV 6-(4-Bromophenyl)-4-ethoxycarbonyl-2H-pyridazin-3-one

A solution of 40 ml of bromine in 100 ml of glacial acetic acid is added dropwise to a suspension of 213 g of 6-(4-bromophenyl)-4,5-dihydro-4-ethoxycarbonyl-2H-pyridazin- 3-one in 2.0 liters of glacial acetic acid and the resulting mixture is stirred for 45 minutes at ambient temperature. It is diluted with 2.0 liters of water and excess bromine is destroyed with dilute sodium sulphite solution. The precipitate is suction filtered, washed with water and dried.

Yield: 206 g (97% of theory), $R_f$ value: 0.39 (silica gel; methylene chloride/methanol= 15:1)

Example XXXVI 6-(4-Cyanophenyl)-4-ethoxycarbonyl-2H-pyridazin-3-one 6.9 g of copper(I)cyanide are added to a solution of 24.6 g of 6-(4-bromophenyl)-4-ethoxycarbonyl-2H-pyridazin-3-one in 100 ml of dimethylformamide and the mixture is refluxed for 6 hours. The reaction solution is cooled and stirred into water. The precipitate is suction filtered and dried. 23 g of crude product are obtained which is further reacted without purification.

$R_f$ value: 0.39 (silica gel; methylene chloride/methanol= 15:1)

Example XXXVII 6-(4-Cyanophenyl)-4-ethoxycarbonyl-2-methyl-2H-pyridazin- 3-one 500 ml of tetrahydrofuran and 1.6 liters of toluene is stirred into a suspension of 18 g of crude 6-(4-cyanophenyl)-4-ethoxycarbonyl-2H-pyridazin-3-one, 7.5 ml of methyliodide, 2.0 g of methyl-trioctylammonium chloride in 200 ml of 2M potassium hydrogen carbonate solution for 16 hours at ambient temperature. 3 ml of methyliodide are added and the mixture is stirred for a further 4 hours. The precipitate is suction filtered and the filtrate is washed with water. The organic phase is dried over sodium sulphate, the solvent is evaporated off in vacuo and the crude product is chromatographed over silica gel.

Yield: 11.2 g (59% of theory), $R_f$ value: 0.49 (silica gel; methylene chloride/methanol= 9:1)

Example XXXVIII

4-Carboxy-6-(4-cyanophenyl)-2-methyl-2H-pyridazin-3-one

A solution of 7.14 g of lithium hydroxide-monohydrate in 170 ml of water is added to a solution of 12.0 g of 6-(4-cyanophenyl)- 4-ethoxycarbonyl-2-methyl-2H-pyridazin-3-one in 200 ml of tetrahydrofuran and the mixture is stirred for 1.5 hours. It is acidified with 1N hydrochloric acid, the tetrahydrofuran is evaporated off in vacuo, the precipitate is suction filtered and dried.

Yield: 11.2 g,

Melting point: 190°–194° C.

$R_f$ value: 0.33 (silica gel; methylene chloride/methanol/conc. aqueous ammonia=4:1:0.25)

The following compound is obtained analogously:

(1) 4-carboxy-6-(4-cyanophenyl)-2H-pyridazin-3-one

Melting point: over 290° C.

Example 1

(3S,5S)-5-[[4-(5-amidino-2-pyridyl)phenyl]oxymethyl]-3-carboxymethyl- 2-pyrrolidinone 3 ml of trifluoroacetic acid are added to a suspension of 0.35 g of (3S,5S)-5-[[4-(5-amidino-2-pyridyl)phenyl]oxymethyl]-3[(tert.butyloxycarbonyl)methyl]-2-pyrrolidinone-hydrochloride in 3 ml of methylene chloride. After 75 minutes' stirring at ambient temperature the mixture is evaporated down. The residue is mixed with water and substantially dissolved with 1N sodium hydroxide solution. It is filtered and the filtrate is adjusted to pH 7 using 2N hydrochloric acid. The jelly-like precipitate is suction filtered, washed with a little water and acetone and dried in vacuo at 80° C.

Yield: 254 mg (84% of theory),
Melting point: 259°–261° C.
$R_f$ value: 0.59 (reversed phase silica gel; methanol/5% aqueous saline solution=6:4)

The following compounds are obtained analogously:
(1) (3S,5S)-5-[[4-(2-amidino-5-pyrimidyl)phenyl]oxymethyl]-3-carboxymethyl-2-pyrrolidinone×0.75 HCl×2 H$_2$O Melting point: 207°–209° C. (decomp., sintering from 186° C.)
$R_f$ value: 0.58 (reversed phase silica gel; methanol/5% aqueous saline solution=6:4)
Calculated: C 49.96; H 5.49; N 16.18; Cl 6.14; Found: 49.77; 5.27; 15.95; 6.36.

(2) (3S,5S)-5-[[4-(5-amidino-2-pyrimidyl)phenyl]oxymethyl]-3-carboxymethyl-2-pyrrolidinone
$R_f$ value: 0.72 (reversed phase silica gel; methanol/5% aqueous saline solution=6:4)
Calculated: C 58.53; H 5.18; N 18.96; Found: 58.22; 5.25; 18.81.

(3) (3S,5S)-5-[[4-(5-amidino-2-thiazolyl)phenyl]oxymethyl]-3-carboxymethyl-2-pyrrolidinone×0.6 H$_2$O
$R_f$ value: 0.63 (reversed phase silica gel; methanol/5% aqueous saline solution=6:4)
Calculated: C 53.00; H 5.03; N 14.55; S 8.32; Found: 52.91; 5.11; 14.44; 8.53.
Mass spectrum: (M+H)$^+$=375

(4) (3S,5S)-3-carboxymethyl-5-[[4-(6-isoquinolinyl)phenyl]-oxymethyl]-2-pyrrolidinone
$R_f$ value: 0.42 (reversed phase silica gel; methanol/10% aqueous saline solution=3:1)
Mass spectrum: M$^+$=376

Example 2

(3S,5S)-5-[[4-(5-amidino-2-pyridyl)phenyl]oxymethyl]-3-[(tert.butyloxycarbonyl)methyl]-2-pyrrolidinone-hydrochloride 2.1 g of (3S,5S)-3-[(tert.butyloxycarbonyl)methyl]-5-[[4-(5-cyano-2-pyridyl)phenyl]oxymethyl]-2-pyrrolidinone in 50 ml of dry methanol are stirred with 8.5 ml of 0.13M sodium methoxide solution for 40 hours at ambient temperature. 63 μl of glacial acetic acid followed by 0.5 g of ammonium chloride are added and the mixture is stirred for 2½ days at ambient temperature After evaporation the mixture is purified by column chromatography on silica gel using methylene chloride/methanol (6:1).

Yield: 1 g (42% of theory),
Melting point: 207° C. (decomp.)
$R_f$ value: 0.56 (silica gel; methylene chloride/methanol= 4:1)

The following compounds are obtained analogously:
(1) (3S,5S)-5-[[4-(2-amidino-5-pyridyl)phenyl]oxymethyl]-3-[(tert.butyloxycarbonyl)-methyl]-2-pyrrolidinone-hydrochloride
$R_f$ value: 0.50 (silica gel; methylene chloride/methanol= 6:1)

(2) (3S,5S)-5-[[4-(5-amidino-2-pyrazinyl)phenyl]oxymethyl]-3-[(tert.butyloxycarbonyl)methyl]-2-pyrrolidinone-hydrochloride
Melting point: 213° C. (decomp.)
$R_f$ value: 0.55 (silica gel; methylene chloride/methanol= 6:1)

(3) (3S,5S)-5-[[4-(2-amidino-5-pyrimidyl)phenyl]oxymethyl]-3-[(tert.butyloxycarbonyl)methyl]-2-pyrrolidinone-hydrochloride
Melting point: 197°–198° C.
$R_f$ value: 0.33 (reversed phase silica gel; methanol/5% aqueous saline solution=6:4)

(4) (3S,5S)-5-[[4-(5-amidino-2-pyrimidyl)phenyl]oxymethyl]-3-[(tert.butyloxycarbonyl)methyl]-2-pyrrolidinone-hydrochloride
Melting point: 277°–279° C. (decomp.)
$R_f$ value: 0.38 (reversed phase silica gel; methanol/5% aqueous saline solution=6:4)

(5) (3S,5S)-5-[[4-(5-amidino-2-thiazolyl)phenyl]oxymethyl] -3-[(tert.butyloxycarbonyl)methyl]-2-pyrrolidinone-hydrochloride
$R_f$ value: 0.46 (reversed phase silica gel; methanol/5% aqueous saline solution=6:4)

(6) (3S,5S)-5-[[4-(6-amidino-3-pyridazinyl)phenyl]oxymethyl] -3-[(methoxycarbonyl)methyl]-2-pyrrolidinone-hydrochloride (7) (3S,5S)-5-[[4-(5-amidino-2-pyrimidyl)phenyl]oxymethyl] -3-[(methoxycarbonyl)methyl]-1-phenyl-2-pyrrolidinone-hydrochloride (8) (3R,5R)-5-[[4-(5-amidino-2-pyrimidyl)phenyl]oxymethyl] -3-[(methoxycarbonyl)methyl]-2-pyrrolidinone-hydrochloride (9) (3S,5S)-5-[[4-(5-amidino-2-pyrimidyl)phenyl]oxymethyl] -3-[(methoxycarbonyl)methyl]-3-methyl-2-pyrrolidinone-hydrochloride

(10) (3S,5S)-5-[[4-(5-amidino-2-thiazolyl)phenyl]oxymethyl] -1-(2-methoxyethyl)-3-[(methoxycarbonyl)methyl] -2-pyrrolidinone-hydrochloride

(11) (3R,4R)-4-[[4-(5-amidino-2-pyrimidyl)phenyl]oxymethyl] -3-[(methoxycarbonyl)methyl]-3-methyl-2-pyrrolidinone-hydrochloride

(12) (3S,5S)-4-[[4-(5-amidino-2-pyrimidyl)phenyl]oxymethyl] -1,3-bis-[(methoxycarbonyl)methyl]-2-pyrrolidinone-hydrochloride

(13) (3S,5S)-5-[[4-(5-amidino-2-pyrimidyl)phenyl]oxymethyl] -1-[(dimethylaminocarbonyl)methyl]-3-[(methoxycarbonyl)methyl]-2-pyrrolidinone-hydrochloride

(14) (3S,5S)-5-[[4-(5-amidino-2-pyrimidyl)phenyl]oxymethyl] -3-[(methoxycarbonyl)methyl]-1-[(morpholine-N-carbonyl)methyl] -2-pyrrolidinone-hydrochloride

(15) (3S,5S)-5-[[4-(5-amidino-2-pyrimidyl)phenyl]oxymethyl] -3-[(methoxycarbonyl)methyl]-1-[(thiomorpholine-N-carbonyl)methyl]-2-pyrrolidinone-hydrochloride

(16) (3S,5S)-5-[[4-(5-amidino-2-pyrimidyl)phenyl]oxymethyl] -3-[(methoxycarbonyl)methyl]-1-[(S-oxidothiomorpholine-N-carbonyl)methyl] -2-pyrrolidinone-hydrochloride

(17) (3S,5S)-5-[[4-(5-amidino-2-pyrimidyl)phenyl]oxymethyl] -3-[(methoxycarbonyl)methyl]-1-[(S,S-dioxidothiomorpholine-N-carbonyl)methyl] -2-pyrrolidinone-hydrochloride

(18) (3S,5S)-1-acetyl-5-[[4-(5-amidino-2-pyrimidyl)phenyl]oxymethyl] -3-[(methoxycarbonyl)methyl]-pyrrolidine-hydrochloride

(19) (3S,5S)-5-[[4-(5-amidino-2-pyridyl)phenyl]oxymethyl] -1-methoxyacetyl-3-[(methoxycarbonyl)methyl]pyrrolidine-hydrochloride

(20) (3S,5S)-5-[[4-(5-amidino-2-pyrimidyl)phenyl]oxymethyl] -1-methanesulphonyl-3-[(methoxycarbonyl)methyl] -pyrrolidine-hydrochloride

(21) (3S,5S)-5-[[4-(5-amidino-2-pyridyl)phenyl]oxymethyl] -1-dimethylaminosulphonyl-3-[(methoxycarbonyl)methyl]-pyrrolidine-hydrochloride

(22) (3S,5S)-5-[[4-(5-amidino-2-pyridyl)phenyl]oxymethyl] -1-benzoyl-3-[(methoxycarbonyl)methyl]pyrrolidine-hydrochloride
(23) (3S,5S)-5-[[4-(5-amidino-2-pyridyl)phenyl]oxymethyl] -1-ethylaminocarbonyl-3-[(methoxycarbonyl)methyl] -pyrrolidine-hydrochloride
(24) (3S,5S)-5-[[4-(5-amidino-2-pyridyl)phenyl]oxymethyl] -1-dimethylaminocarbonyl-3-[(methoxycarbonyl)methyl]-pyrrolidine-hydrochloride
(25) (3S,5S)-5-[[4-(5-amidino-2-pyridyl)phenyl]oxymethyl] -3-[(methoxycarbonyl)methyl]-1-(4methoxyphenyl-sulphonyl)-pyrrolidine-hydrochloride
(26) (3R,5S)-5-[[4-(5-amidino-2-pyrazinyl)phenyl]oxymethyl] -3-[(methoxycarbonyl)methyl]-2-pyrrolidinone-hydrochloride
(27) (3S,5S)-5-[[4-(5-amidino-2-pyrimidyl)phenyl]oxymethyl] -3-[(methoxycarbonyl)methyl]-1-nicotinoylpyrrolidine-hydrochloride
(28) 1-[4-(5-amidino-2-pyrimidyl)phenyl]-4-(O-methylphosphonomethyl)-2-pyrrolidinone
(29) 1-[4-(5-amidino-2-pyrimidyl)phenyl]-4-phosphonomethyl-2-pyrrolidinone
(30) (3R,5S)-5-[[4-(5-amidino-2-thiazolyl)phenyl]oxymethyl] -3-[2-(methoxycarbonyl)ethyl]-2-pyrrolidinone-hydrochloride Example 3

(3S,5S)-5-[[4-(5-Amidino-2-pyridyl)phenyl]oxymethyl] -3-[(methoxycarbonyl)methyl]-2-pyrrolidinone×1.6 HCl×1.5 $H_2O$ 0.55 g of (3S,5S)-5-[[4-(5-amidino-2-pyridyl)phenyl] oxymethyl]-3-[(tert.butyloxycarbonyl)methyl]-2-pyrrolidinone in 15 ml of dry methanol are mixed with 2 ml of saturated methanolic hydrochloric acid and stirred for 18 hours at ambient temperature. A further 15 ml of methanol and 2 ml of saturated methanolic hydrochloric acid are added and the mixture is stirred for a further 24 hours. The mixture is then evaporated down and the residue is combined with methanol and evaporated to dryness. The residue is triturated with tert.butyl-methylether and a little methanol and suction filtered. Purification over a silica gel column using methylene chloride/methanol (4:1) yields 0.28 g (46% of theory).

Melting point: 253° C. (decomp.)

$R_f$ value: 0.42 (reversed phase silica gel; methanol/5% aqueous saline solution=6:4)

Calculated: C 51.35; H 5.73; N 11.98; Cl 12.13; Found: 51.49; 5.51; 11.71; 12.12.

Mass spectrum: $(M+H)^+=383$

The following compounds are obtained analogously:
(1) (3S,5S)-5-[[4-(2-amidino-5-pyridyl)phenyl]oxymethyl]-3-[(methoxycarbonyl)methyl]-2-pyrrolidinone×1.3 HCl×0.3 $H_2O$ $R_f$ value: 0.54 (reversed phase silica gel; methanol/5% aqueous saline solution=6:4)

Calculated: C 55.19; H 5.54; N 12.87; Cl 10.59; Found: 55.13; 5.76; 12.56; 10.83.
(2) (3S,5S)-5-[[4-(5-amidino-2-pyrazinyl)phenyl]oxymethyl] -3-[(methoxycarbonyl)methyl]-2-pyrrolidinone-hydrochloride $R_f$ value: 0.52 (reversed phase silica gel; methanol/5% aqueous saline solution=6:4)
(3) (3S,5S)-5-[[4-(2-amidino-5-pyrimidyl)phenyl]oxymethyl]-3-[(methoxycarbonyl)methyl]-2-pyrrolidinone×1.5 HCl×1 $H_2O$ Melting point: 193°–195° C.

$R_f$ value: 0.51 (reversed phase silica gel; methanol/5% aqueous saline solution=6:4)

Calculated: C 50.03; H 5.42; N 15.36; Cl 11.66; Found: 49.85; 5.61; 15.59; 11.76.
(4) (3S,5S)-5-[[4-(5-amidino-2-pyrimidyl)phenyl]oxymethyl]-3-[(methoxycarbonyl)methyl]-2-pyrrolidinone×1.4 HCl×2 $H_2O$ $R_f$ value: 0.45 (reversed phase silica gel; methanol/5% aqueous saline solution=6:4)

Calculated: C 48.50; H 5.66; N 14.89; Cl 10.55; Found: 48.72; 5.64; 14.57; 10.75.
(5) (3S,5S)-5-[[4-(5-amidino-2-thiazolyl)phenyl]oxymethyl]-3-[(methoxycarbonyl)methyl]-2-pyrrolidinone-hydrochloride $R_f$ value: 0.45 (reversed phase silica gel; methanol/5% aqueous saline solution=6:4)

Mass spectrum: $(M+H)^+=389$

Example 4

(3S,5S)-5-[[4-(2-Amidino-5-pyridyl)phenyl]oxymethyl]-3-carboxymethyl- 2-pyrrolidinone 180 mg of (3S,5S)-5-[[4-(2-amidino-5-pyridyl)phenyl] oxymethyl]-3-[(methoxycarbonyl)methyl]-2-pyrrolidinone×1.3 HCl×0.3 $H_2O$, 5 ml of methanol and 1.3 ml of 1N NaOH are stirred for 5 hours at ambient temperature. Then 0.26 g of ammonium chloride are added and the mixture is stirred for half an hour. The mixture is evaporated down and the precipitate is suction filtered and dried.

Yield: 115 mg (72% of theory),

Melting point: 276°–278° C.

$R_f$ value: 0.62 (reversed phase silica gel; methanol/5% aqueous saline solution=6:4)

Calculated: C 60.47; H 5.61; N 14.85; Found: 60.54; 5.66; 14.77.

The following compounds are obtained analogously:
(1) (3S,5S)-5-[[4-(5-amidino-2-pyrazinyl)phenyl]oxymethyl] -3-carboxymethyl-2-pyrrolidinone Melting point: 272°–275° C.

$R_f$ value: 0.66 (reversed phase silica gel; methanol/5% aqueous saline solution=6:4)

Calculated: C 56.33; H 5.41; N 18.25; Found: 56.47; 5.50; 17.78.
(2) (3S,5S)-5-[(4'-amidino-4-biphenylyl)oxymethyl]-3-carboxymethyl- 1-(2-pyrimidyl)-pyrrolidine×0.25 HCl×0.4 $H_2O$ Melting point: 254°–257° C.

$R_f$ value: 0.27 (reversed phase silica gel; methanol/5% aqueous saline solution=6:4)

Calculated: C 64.37; H 5.86; N 15.64; Cl 1.98; Found: 64.46; 5.65; 15.45; 1.85.
(3) (3S,5S)-5-[[4-(1-amino-6-isoquinolinyl)phenyl]oxymethyl] -3-carboxymethyl-2-pyrrolidinone-hydrochloride After the addition of ammonium chloride, 1N hydrochloric acid is added and the precipitate is suction filtered.

Melting point: >200° C.

$R_f$ value: 0.47 (reversed phase silica gel; methanol/5% aqueous saline solution=6:4)

Mass spectrum: $M^+=391$
(4) (3S,5S)-5-[(4'-amidino-4-biphenylyl)oxymethyl]-3-carboxymethyl- 1-nicotinoyl-pyrrolidine Melting point: 227°–230° C. (decomp.)

$R_f$ value: 0.08 (silica gel; methylene chloride/methanol/ conc. aqueous ammonia=10:2:0.4)
(5) (3S,5S)-5-[(4'-amidino-4-biphenylyl)oxymethyl]-3-carboxymethyl- 1-(2-pyridyl)-2-pyrrolidinone Melting point: 230°–233° C. (decomp.)

$R_f$ value: 0.28 (reversed phase silica gel; methanol/10% aqueous saline solution=6:4)

(6) (3S,5S)-5-[(4'-amidino-4-biphenylyl)oxymethyl]-3-carboxymethyl- 1-(3-pyridyl)-2-pyrrolidinone×1.2 H₂O Melting point: 209°–211° C. (decomp.)

R_f value: 0.54 (reversed phase silica gel; methanol/10% aqueous saline solution=6:4)

Calculated: C 64.45; H 5.71; N 12.03; Found: 64.33; 5.70; 11.94.

(7) (3s,5s)-5-[[(7-amidino-1H-2,3,4,5-tetrahydro-3-benzazepin- 3-yl)carbonylamino]methyl]-3-carboxymethyl-1-( 3-phenylpropyl)-2-pyrrolidinone×0.5 H₂O R_f value: 0.36 (silica gel; methylene chloride/methanol/ conc. aqueous ammonia=30:15:3)

Calculated: C 65.35; H 7.05; N 13.61; Found: 65.00; 7.00; 13.39.

Mass spectrum: (M+H)⁺=506

(8) (3S,5S)-5-[2-[(7-amidino-1H-2,3,4,5-tetrahydro-3-benzazepin- 3-yl)carbonylamino]ethyl]-3-carboxymethyl-1-( 3-phenylpropyl)-2-pyrrolidinone×2 H₂O Melting point: from 190° C. (decomp.)

R_f value: 0.12 (silica gel; methylene chloride/methanol/ conc. aqueous ammonia=80:20:5)

Calculated: C 62.88; H 7.44; N 12.60; Found: 62.88; 7.22; 12.48.

(9) (3S,5S)-5-[2-[(7-amidino-1,2,3,4-tetrahydro-2-isoquinolinyl)carbonylamino] ethyl]-3-carboxymethyl-1-(3-phenylpropyl)- 2-pyrrolidinone×1.5 H₂O R_f value: 0.24 (silica gel; methylene chloride/methanol/ conc. aqueous ammonia=80:20:5)

Calculated: C 63.14; H 7.19; N 13.15; Found: 63.09; 7.27; 13.05.

(10) (3S,5S)-5-[[(7-amidino-1,2,3,4-tetrahydro-2-isoquinolinyl)carbonylamino]methyl]-3-carboxymethyl-1(3-phenylpropyl)-2-pyrrolidinone×0.5 H₂O R_f value: 0.22 (silica gel; methylene chloride/methanol/ conc. aqueous ammonia=80:20:5)

Calculated: C 64.78; H 6.85; N 13.99; Found: 64.67; 6.84; 14.00.

(11) (3S,5S)-5-[[6-(4-amidinophenyl)-3-pyridazinyl] oxymethyl-3-carboxymethyl-1-(3-phenylpropyl)- 2-pyrrolidinone×1 H₂O R_f value: 0.16 (silica gel; methylene chloride/methanol/ conc. aqueous ammonia=16:4:1)

Calculated: C 64.14; H 6.18; N 13.85; Found: 64.07; 6.14; 13.96.

(12) (3S,5S)-5-[[6-(4-amidinophenyl)-3-pyridazinyl]aminomethyl]-3-carboxymethyl-1-(3-phenylpropyl)-2-pyrrolidinone R_f value: 0.28 (silica gel; methylene chlorid/methanol/ conc. aqueous ammonia=8:4:1)

(13) (3S,5S)-5-[[6-(4-amidinophenyl)-3-pyridazinyl] aminomethyl]-3-carboxymethyl-2-pyrrolidinone R_f value: 0.13 (silica gel; methylene chloride/methanol/ conc. aqueous ammonia=8:4:1)

(14) (3S,5S)-5-[[[6-(4-amidinophenyl)-3(2H)-pyridazinon-4-yl]carbonyl]aminomethyl]-3-carboxymethyl-2-pyrrolidinone R_f value: 0.094 (silica gel; methylene chloride/methanol/ conc. aqueous ammonia= 8:4:1)

(15) (3S,5S)-5-[[[6-(4-amidinophenyl)-2-methyl-3(2H)-pyridazinon- 4-yl]carbonyl]aminomethyl]-3-carboxymethyl-2-pyrrolidinone R_f value: 0.24 (silica gel; methylene chloride/methanol/ conc. aqueous ammonia=8:4:1)

(16) (3S,5S)-5-[[[6-(4-amidinophenyl)-3(2H)-pyridazinon-4-yl]carbonyl]aminomethyl]-3-carboxymethyl-1-(3-phenylpropyl)-2-pyrrolidinone R_f value: 0.30 (silica gel; methylene chloride/methanol/ conc. aqueous ammonia=8:4:1)

(17) (3S,5S)-5-[[3-[(4-amidinophenyl)aminocarbonyl]-(2-(1H)-pyridon-1-yl]methyl]-3-carboxymethyl-2-pyrrolidinone R_f value: 0.36 (silica gel; methylene chloride/methanol/ glacial acetic acid=30:10:1, developed twice)

(18) (3S,5S)-5-[[3-[(4-amidinophenyl)aminocarbonyl]-(2(1H)-pyridon-1-yl]methyl]-3-carboxymethyl-1-(3-phenylpropyl)- 2-pyrrolidinone×1.5 H₂O R_f value: 0.26 (silica gel; tetrahydrofuran/1N-hydrochloric acid=10:1)

Calculated: C 62.58; H 6.16; N 12.58; Found: 62.42; 6.21; 12.64.

(19) (3S,5S)-5-[[5-[(4-amidinophenyl)aminocarbonyl]-2(1H)-pyridon-1-yl]methyl]-3-carboxymethyl-1-(3-phenylpropyl)- 2-pyrrolidinone×1 H₂O R_f value: 0.33 (silica gel; methylene chloride/methanol/ glacial acetic acid=30:10:1)

Calculated: C 63.61; H 6.07; N 12.79; Found: 63.83; 6.14; 12.90.

(20) (3S,5S)-5-[[5-[(4-amidinophenyl)aminocarbonyl]-2,4-(1H,3H)pyrimidindion-3-yl]methyl]-3-carboxymethyl-1-(3-phenylpropyl)- 2-pyrrolidinone×1 H₂O R_f value: 0.14 (silica gel; methylene chloride/methanol/ conc. aqueous ammonia=10:10:1)

Calculated: C 59.57; H 5.71; N 14.89; Found: 59.42; 5.86; 14.62.

(21) (3S,5S)-5-[[6-(4-amidinophenyl)-3-pyridazinyl] oxymethyl]-3-carboxymethyl-2-pyrrolidinone

(22) (3S,5S)-5-[[4-(5-amidino-2-thienyl)phenyl]oxymethyl] -3-carboxymethyl-2-pyrrolidinone

(23) (3S,5S)-5-[[4-(5-amidino-2-furyl)phenyl]oxymethyl] -3-carboxymethyl-2-pyrrolidinone

(24) (3S,5S)-5-[[4-(5-amidino-1-methyl-2-pyrrolyl)phenyl] oxymethyl]-3-carboxymethyl-2pyrrolidinone

(25) (3S,5S)-5-[[4-(4-amidino-1-methyl-2-imidazolyl)phenyl] oxymethyl]-3-carboxymethyl-2pyrrolidinone

(26) (3S,5S)-5-[[4-(6-amidino-3-pyridazinyl)phenyl]oxymethyl] -3-carboxymethyl-2-pyrrolidinone

(27) (3S,5S)-5-[[6-(4-amidinophenyl)-3-pyridazinyl]oxymethyl] -3-carboxymethyl-1-methyl-2-pyrrolidinone

(28) (3S,5S)-5-[[6-(4-amidinophenyl)-3-pyridazinyl]oxymethyl] -1-benzyl-3-carboxymethyl-2-pyrrolidinone

(29) (3S,5S)-5-[[6-(4-amidinophenyl)-3-pyridazinyl]oxymethyl] -3-carboxymethyl-1-[3-(3,4dimethoxyphenyl)propyl] -2-pyrrolidinone

(30) (3S,5S)-5-[[6-(4-amidinophenyl)-3-pyridazinyl]oxymethyl] -3-carboxymethyl-1-[3-(3-trifluoromethylphenyl) propyl] -2-pyrrolidinone

(31) (3S,5S)-5-[[6-(4-amidinophenyl)-3-pyridazinyl] oxymethyl]-3-carboxymethyl-1-[3-(2,4-dichlorophenyl)propyl] -2-pyrrolidinone

(32) (3S,5S)-5-[[6-(4-amidinophenyl)-3-pyridazinyl]oxymethyl] -3-carboxymethyl-1-[3-(4-methylthiophenyl)propyl] -2-pyrrolidinone

(33) (3S,5S)-5-[[6-(4-amidinophenyl)-3-pyridazinyl]oxymethyl] -3-carboxymethyl-1-[3-(4-methylsulphonylphenyl )propyl] -2-pyrrolidinone

(34) (3S,5S)-5-[[4-(5-amidino-2-pyrimidyl)phenyl]oxymethyl] -3-carboxymethyl-1-phenyl-2-pyrrolidinone

(35) (3R,5R)-5-[[4-(5-amidino-2-pyrimidyl)phenyl]oxymethyl] -3-carboxymethyl-2-pyrrolidinone

(36) (3S,5S)-5-[[4-(5-amidino-2-pyrimidyl)phenyl]oxymethyl] -3-carboxymethyl-3-methyl-2-pyrrolidinone

(37) (3S,5S)-5-[[4-(5-amidino-2-thiazolyl)phenyl]oxymethyl] -3-carboxymethyl-1-(2-methoxyethyl)-2pyrrolidinone

(38) (3R,4R)-4-[[4-(5-amidino-2-pyrimidyl)phenyl]oxymethyl] -3-carboxymethyl-3-methyl-2-pyrrolidinone
(39) (3S,5S)-5-[(4'-amidino-3'-fluoro-4-biphenylyl)oxymethyl] -3-carboxymethyl-1-nicotinoyl-pyrrolidine
(40) (3S,5S)-5-[(4'-amidino-3-bromo-4-biphenylyl)oxymethyl] -3-carboxymethyl-1-nicotinoyl-pyrrolidine
(41) (3S,5S)-5-[(4'-amidino-2,3-dimethyl-4-biphenylyl)oxymethyl] -3-carboxymethyl-1-nicotinoyl-pyrrolidine
(42) (3S,5S)-5-[(4'-amidino-3-nitro-4-biphenylyl)oxymethyl] -3-carboxymethyl-1-nicotinoyl-pyrrolidine
(43) (3S,5S)-5-[(3-acetylamino-4'-amidino-4-biphenylyl)oxymethyl] -3-carboxymethyl-1-nicotinoyl -pyrrolidine
(44) (3S,5S)-5-[(4'-amidino-3-methanesulphonylamino-4-biphenylyl)oxymethyl]-3-carboxymethyl-1-nicotinoylpyrrolidine
(45) (3S,5S)-5-[[4-(5-amidino-2-pyrimidyl)phenyl]oxymethyl] -1,3-bis(carboxymethyl)-2-pyrrolidinone
(46) (3S,5S)-5-[[4-(5-amidino-2-pyrimidyl)phenyl]oxymethyl] -3-carboxymethyl-1-[(dimethylaminocarbonyl)methyl] -2-pyrrolidinone
(47) (3S,5S)-5-[[4-(5-amidino-2-pyrimidyl)phenyl]oxymethyl] -3-carboxymethyl -1-[(morpholine-N-carbonyl)methyl] -2-pyrrolidinone
(48) (3S,5S)-5-[[4-(5-amidino-2-pyrimidyl)phenyl]oxymethyl] -3-carboxymethyl-1-[(thiomorpholine-N-carbonyl)methyl] -2-pyrrolidinone
(49) (3S,5S)-5-[[4-(5-amidino-2-pyrimidyl)phenyl]oxymethyl] -3-carboxymethyl -1-[(S-oxido-thiomorpholine-N-carbonyl)methyl] -2-pyrrolidinone
(50) (3S,5S)-5-[[4-(5-amidino-2-pyrimidyl)phenyl]oxymethyl] -3-carboxymethyl-1-[(S, S-dioxidothiomorpholine-N-carbonyl)methyl] -2-pyrrolidinone
(51) (3S,5S)-1-acetyl-5-[[4-(5-amidino-2-pyrimidyl)phenyl]oxymethyl] -3-carboxymethyl-pyrrolidine
(52) (3S,5S)-5-[[4-(5-amidino-2-pyridyl)phenyl]oxymethyl] -3-carboxymethyl-1-methoxyacetyl-pyrrolidine
(53) (3S,5S)-5-[[4-(5-amidino-2-pyrimidyl)phenyl]oxymethyl] -3-carboxymethyl-1-methanesulphonylpyrrolidine
(54) (3S,5S)-5-[[4-(5-amidino-2-pyridyl)phenyl]oxymethyl] -3-carboxymethyl-1-dimethylaminosulphonylpyrrolidine
(55) (3S,5S)-5-[[4-(5-amidino-2-pyridyl)phenyl]oxymethyl] -1-benzoyl-3-carboxymethyl-pyrrolidine
(56) (3S,5S)-5-[[4-(5-amidino-2-pyrimidyl)phenyl]oxymethyl] -3-carboxymethyl-1-ethylaminocarbonylpyrrolidine
(57) (3S,5S)-5-[[4-(5-amidino-2-pyrimidyl)phenyl]oxymethyl] -3-carboxymethyl-1-dimethylaminocarbonylpyrrolidine
(58) (3S,5S)-5-[[4-(5-amidino-2-pyridyl)phenyl]oxymethyl] -3-carboxymethyl-1-(4-methoxyphenylsulphonyl)pyrrolidine
(59) (3S,5S)-3-carboxymethyl-5-[[6-[4-(N-methylamidino)-phenyl]-3-pyridazinyl]oxymethyl]-2-pyrrolidinone
(60) (3R,5S)-5-[[4-(5-amidino-2-pyrazinyl)phenyl]oxymethyl] -3-carboxymethyl-2-pyrrolidinone
(61) (3S,5S)-5-[(4'-amidino-4-biphenylyl)oxymethyl]-3-carboxymethyl- 1-(2-benzthiazolyl)-pyrrolidine
(62) (3S,5S)-5-[(4'-amidino-4-biphenylyl)oxymethyl]-3-carboxymethyl- 1-(2-pyrazinyl)-pyrrolidine
(63) (3S,5S)-5-[(4'-amidino-4-biphenylyl)oxymethyl]-3-carboxymethyl- 1-(3-furancarbonyl)-pyrrolidine
(64) (3S,5S)-5-[(4'-amidino-4-biphenylyl)oxymethyl]-3-carboxymethyl- 1-(tetrahydrofuran-2-carbonyl)-pyrrolidine
(65) (3S,5S)-5-[(4'-amidino-4-biphenylyl)oxymethyl]-3-carboxymethyl- 1-[(2-methyl-4-thiazolyl)carbonyl]pyrrolidine
(66) (3S,5S)-5-[(4'-amidino-4-biphenylyl)oxymethyl]-3-carboxymethyl- 1-(4-pyrazolylcarbonyl)-pyrrolidine
(67) (3S,5S)-5-[(4'-amidino-4-biphenylyl)oxymethyl]-3-carboxymethyl- 1-[((1H)-1,2,4-triazol-1-yl)methylcarbonyl]-pyrrolidine
(68) (3S,5S)-5-[(4'-amidino-4-biphenylyl)oxymethyl]-3-carboxymethyl-1-(4-pyridylcarbonyl)-pyrrolidine
(69) (3S,5S)-5-[[4-(5-amidino-2-pyrimidyl)phenyl]oxymethyl] -3-carboxymethyl-1-nicotinoyl-pyrrolidine
(70) (3S,5S)-5-[[4-(4-amidinophenyl)-2-thiazolyl]aminomethyl] -3-carboxymethyl-2-pyrrolidinone
(71) (3S,5S)-5-[[N-[5-(4-amidinophenyl)-2-pyrazinyl]—N-methyl]aminomethyl] -3-carboxymethyl-2-pyrrolidinone
(72) (3S,5S)-5-[(4'-amidino-3-methylsulphenyl-4-biphenylyl)oxymethyl] -3-carboxymethyl-1-nicotinoylpyrrolidine
(73) (3S,5S)-5-[(4'-amidino-3-methylsulphonyl-4-biphenylyl)oxymethyl] -3-carboxymethyl-1-nicotinoylpyrrolidine
(74) (3S,5S)-5-[[1-(4-amidinophenyl)piperidin-4-yl]aminomethyl] -3-carboxymethyl-2-pyrrolidinone
(75) (3S,5S)-5-[[N-[1-(4-amidinophenyl)piperidin-4-yl]-N-methyl]aminomethyl] -3-carboxymethyl-2-pyrrolidinone
(76) (3S,5S)-5-[[N-acetyl-N-[1-(4-amidinophenyl)-piperidin-4 -yl]]aminomethyl]-3-carboxymethyl-2-pyrrolidinone
(77) (3S,5S)-5-[[N-[1-(4-amidinophenyl)piperidin-4-yl] -N-methanesulphonyl]aminomethyl]-3-carboxymethyl-2-pyrrolidinone
(78) (3S,5S)-5-[[1-(4-amidinophenyl)piperidin-4-yl]oxymethyl] -3-carboxymethyl-1-(3-phenylpropyl)-2-pyrrolidinone
(79) (3S,5S)-5-[2-[1-(4-amidinophenyl)piperazin-4-yl] ethyl] -3-carboxymethyl-2-pyrrolidinone
(80) (3R,5S)-5-[[4-(5-amidino-2-thiazolyl)phenyl]oxymethyl] -3-(2-carboxyethyl)-2-pyrrolidinone
(81) (3S,5S)-5-[[1-(4-amidinophenyl)piperidin-4-yl]oxymethyl] -3-carboxymethyl-2-pyrrolidinone
(82) (3S,5S)-3-carboxymethyl-5-[[4-(2-methyl-1,2,3,4-tetrahydro- 6-isoquinolinyl)phenyl]oxymethyl]-2-pyrrolidinone Example 5

(3S,5S)-5-[[4-[5-(N-Methoxycarbonylamidino)-2-pyridyl] phenyl]oxymethyl] -3-[(methoxycarbonyl)methyl]-2-pyrrolidinone 3 ml of 0.2M sodium hydroxide solution are added dropwise to 100 mg of (3S,5S)-5-[[4-(5-amidino-2-pyridyl)phenyl]oxymethyl]-3-[(methoxycarbonyl)methyl]-2-pyrrolidinone×1.6 HCl×1.5 H$_2$O and 19.4 µl of methyl chloroformate in 10 ml of methylene chloride with vigorous stirring at ambient temperature. Then the mixture is stirred for a further 2½ hours at ambient temperature. It is diluted with methylene chloride, the organic phase is separated off, dried and evaporated down.

Yield: 50.4 mg (55% of theory),
Melting point: 180°–183° C.
Mass spectrum: (M+H)$^+$=441

The following compounds are obtained analogously:
(1) (3S,5S)-5-[[4-[2-(N-methoxycarbonylamidino)-5-pyridyl]phenyl]oxymethyl] -3-[(methoxycarbonyl)methyl]-2-pyrrolidinone
Melting point: 167°–169° C.
Mass spectrum: (M+H)$^+$=441
(2) (3S,5S)-5-[[4-[5-(N-methoxycarbonylamidino)-2-pyrazinyl]phenyl]oxymethyl] -3-[(methoxycarbonyl)methyl]-2-pyrrolidinone
Melting point: 210°–212° C.
Mass spectrum: (M+H)$^+$=442
(3) (3S,5S)-5-[[4-[5-(N-ethoxycarbonylamidino)-2-pyridyl] phenyl]oxymethyl] -3-[(ethoxycarbonyl)methyl]-2-pyrrolidinone (4) (3S,5S)-5-[[4-[5-(N-benzyloxycarbonylamidino)-2-pyridyl]phenyl]oxymethyl] -3-[(methoxycarbonyl)methyl]-2-pyrrolidinone (5) (3S,5S)-5-[[4-[5-(N-isobutoxycarbonylamidino)-2-pyrimidyl]phenyl]oxymethyl] -3-[(methoxycarbonyl)methyl]-2-pyrrolidinone (6) (3S,5S)-3-[(cyclohexyloxycarbonyl)methyl]-5-[[4-[5-(N-methoxycarbonylamidino)- 2-pyridyl]phenyl]oxymethyl]-2-pyrrolidinone

Example 6

(3S,5S)-5-[(4'-amidino-4-biphenylyl)oxymethyl]-3-[(methoxycarbonyl)methyl]-1-(2-pyrimidyl)-pyrrolidine×2.25 HCl×1 H$_2$O 12 ml of dry methanol are saturated with dry hydrochloric acid gas whilst cooling with ice. The methanolic hydrochloric acid is added to a solution of 0.86 g of (3S,5S)-5-[(4'-cyano-4-biphenylyl)oxymethyl]-3-[(methoxycarbonyl)methyl]-1-(2-pyrimidyl)pyrrolidine in 2 ml of dry methanol and the mixture is saturated again with hydrochloric acid. The mixture is covered with petroleum ether and left to stand overnight. It is then evaporated down and the residue is stirred with 12 ml of dry methanol and 0.9 g of ammonium carbonate for 20 hours at ambient temperature. It is then concentrated by evaporation and the residue is stirred with 20 ml of methylene chloride/methanol (85:15). It is suction filtered, the filtrate is evaporated down and stirred with 5 ml of methanol and 4 ml of concentrated aqueous ammonia for 18 hours at ambient temperature. It is then acidified with hydrochloric acid and concentrated by evaporation. The residue is stirred with methylene chloride/methanol (85:15), then filtered and evaporated down. After chromatography over a silica gel column, 0.46 g (42%) of theory are obtained.

R$_f$ value: 0.48 (silica gel; methylene chloride/methanol= 4:1)

Calculated: C 55.04; H 5.77; N 12.84; Cl 14.62; Found: 54.78; 5.70; 12.74; 14.32.

Mass spectrum: M$^+$=445

The following compounds are obtained analogously:

(1) (3S,5S)-5-[(4'-amidino-4-biphenylyl)oxymethyl]-3-[(methoxycarbonyl)methyl] -1-nicotinoyl-pyrrolidinehydrochloride R$_f$ value: 0.48 (silica gel; methylene chloride/methanol= 5:1)

(2) (3S,5S)-5-[(4'-amidino-4-biphenylyl)oxymethyl]-3-[(methoxycarbonyl)methyl] -1-(2-pyridyl)-2-pyrrolidinone×1.1 HCl×0.5 H$_2$O R$_f$ value: 0.23 (reversed phase silica gel; methanol/10% aqueous saline solution=6:4)

Calculated: C 61.52; H 5.58; N 11.04; Cl 7.68; Found: 61.73; 5.68; 10.92; 7.54.

(3) (3S,5S)-5-[(4'-amidino-4-biphenylyl)oxymethyl]-3-[(methoxycarbonyl)methyl] -1-(3-pyridyl)-2-pyrrolidinone×1.2 HCl×1 H$_2$O R$_f$ value: 0.39 (reversed phase silica gel; methanol/10% aqueous saline solution=6:4)

Calculated: C 60.02; H 5.66; N 10.77; Cl 8.18; Found: 60.16; 5.94; 10.55; 8.04.

(4) (3S,5S)-5-[[(7-amidino-1H-2,3,4,5-tetrahydro-3-benzazepin- 3-yl)carbonylamino]methyl]-3-[(methoxycarbonyl)methyl] -1-(3-phenylpropyl)-2-pyrrolidinone-hydrochloride R$_f$ value: 0.46 (silica gel; methylene chloride/methanol/ conc. aqueous ammonia=4:1:0.25)

Mass spectrum: (M+H)$^+$=520

(5) (3S,5S)-5-[2-[(7-amidino-1H-2,3,4,5-tetrahydro-3-benzazepin- 3-yl)carbonylamino]ethyl]-3-[(methoxycarbonyl)methyl] -1-(3-phenylpropyl)-2-pyrrolidinone-hydrochloride R$_f$ value: 0.26 (silica gel; methylene chloride/methanol/ conc. aqueous ammonia=80:20:5)

(6) (3S,5S)-5-[2-[(7-amidino-1,2,3,4-tetrahydro-2 -isoquinolinyl)carbonylamino]ethyl] -3-[(methoxycarbonyl)methyl] -1-(3-phenylpropyl)-2-pyrrolidinone-hydrochloride× 0.6 H$_2$O R$_f$ value: 0.29 (silica gel; methylene chloride/methanol/ conc. aqueous ammonia=80:20:5)

Calculated: C 61.44; H 6.97; N 12.35; Found: 61.32; 6.94; 12.58.

(7) (3S,5S)-5-[[(7-amidino-1,2,3,4-tetrahydro-2-isoquinolinyl)carbonylamino]methyl] -3-[(methoxycarbonyl)methyl]-1-(3-phenylpropyl)-2-pyrrolidinone-hydrochloride× 0.75 H$_2$O R$_f$ value: 0.50 (silica gel; methylene chloride/methanol/ conc. aqueous ammonia=80:20:5)

Calculated: C 60.53; H 6.80; N 12.60; Found: 60.57; 6.86; 12.54.

(8) (3S,5S)-5-[[6-(4-amidinophenyl)-3-pyridazinyl]oxymethyl] -3-[(methoxycarbonyl)methyl]-1-(3-phenylpropyl)-2-pyrrolidinone-hydrochloride R$_f$ value: 0.32 (silica gel; methylene chloride/cyclohexane/methanol/conc. aqueous ammonia=68:15:15:2)

(9) (3S,5S)-5-[[6-(4-amidinophenyl)-3-pyridazinyl]aminomethyl] -3-[(methoxycarbonyl)methyl]-1-( 3-phenylpropyl)-2-pyrrolidinone-hydrochloride R$_f$ value: 0.31 (silica gel; methylene chloride/methanol/ conc. aqueous ammonia=16:4:1)

(10) (3S,5S)-5-[[6-(4-amidinophenyl)-3-pyridazinyl]aminomethyl]-3-[(methoxycarbonyl)methyl]-2-pyrrolidinone-hydrochloride R$_f$ value: 0.27 (silica gel; methylene chloride/methanol/ conc. aqueous ammonia=16:4:1)

(11) (3S,5S)-5-[[[6-(4-amidinophenyl)-3(2H)-pyridazinon-4-yl]carbonyl]aminomethyl]-3-[(methoxycarbonyl)methyl]-2-pyrrolidinone-hydrochloride R$_f$ value: 0.34 (silica gel; methylene chloride/methanol/ conc. aqueous ammonia=8:4:1)

(12) (3S,5S)-5-[[[6-(4-amidinophenyl)-2-methyl-3(2H)-pyridazinon- 4-yl]carbonyl]aminomethyl]-3-[(methoxycarbonyl)methyl]-2-pyrrolidinone-hydrochloride R$_f$ value: 0.31 (silica gel; methylene chloride/methanol/ conc. aqueous ammonia=16:4:1)

(13) (3S,5S)-5-[[[6-(4-amidinophenyl)-3(2H)-pyridazinon-4-yl] carbonyl]aminomethyl]-3-[(methoxycarbonyl)methyl] -1-(3-phenylpropyl)-2-pyrrolidinone-hydrochloride R$_f$ value: 0.19 (silica gel; methylene chloride/methanol/ cyclohexane/conc. aqueous ammonia=68:15:15:2)

(14) (3S,5S)-5-[[3-[(4-amidinophenyl)aminocarbonyl] -2(1H)-pyridon-1-yl]methyl]-3-[(methoxycarbonyl)methyl] -2-pyrrolidinone-hydrochloride R$_f$ value: 0.55 (silica gel; methylene chloride/methanol/ glacial acetic acid=30:10:1)

(15) (3S,5S)-5-[[3-[(4-amidinophenyl)aminocarbonyl] -2(1H)-pyridon-1-yl]methyl]-3-[(methoxycarbonyl)methyl] -1-(3-phenylpropyl)-2-pyrrolidinone-hydrochloride R$_f$ value: 0.54 (silica gel; methylene chloride/methanol/ glacial acetic acid=80:20:1)

(16) (3S,5S)-5-[[5-[(4-amidinophenyl)aminocarbonyl] -(2(1H)-pyridon-1-yl]methyl] -1-(3-phenylpropyl)-2-pyrrolidinone-hydrochloride R$_f$ value: 0.44 (silica gel; methylene chloride/methanol/ glacial acetic acid=80:20:1)

(17) (3S,5S)-5-[[5-[(4-amidinophenyl)aminocarbonyl]-2,4-(1H,3H)-pyrimidindion-3-yl]methyl]-3-[(methoxycarbonyl)methyl]-1-(3-phenylpropyl)-2-pyrrolidinone-hydrochloride $R_f$ value: 0.54 (silica gel; methylene chloride/methanol= 3:1)

(18) (3S,5S)-5-[[6-(4-amidinophenyl)-3-pyridazinyl]oxymethyl] -3-[(methoxycarbonyl)methyl]-2-pyrrolidinone-hydrochloride

(19) (3S,5S)-5-[[4-(5-amidino-2-thienyl)phenyl]oxymethyl] -3-[(methoxycarbonyl)methyl]-2-pyrrolidinone-hydrochloride

(20) (3S,5S)-5-[[4-(5-amidino-2-furyl)phenyl]oxymethyl]-3-[(methoxycarbonyl)methyl]-2-pyrrolidinone-hydrochloride

(21) (3S,5S)-5-[[4-(5-amidino-1-methyl-2-pyrrolyl)phenyl]oxymethyl] -3-[(methoxycarbonyl)methyl]-2-pyrrolidinone-hydrochloride

(22) (3S,5S)-5-[[4-(4-amidino-1-methyl-2-imidazolyl)phenyl]oxymethyl] -3-[(methoxycarbonyl)methyl] -2-pyrrolidinone-hydrochloride

(23) (3S,5S)-5-[[6-(4-amidinophenyl)-3-pyridazinyl]oxymethyl] -3-[(methoxycarbonyl)methyl]-1-methyl- 2-pyrrolidinone-hydrochloride

(24) (3S,5S)-5-[[6-(4-amidinophenyl)-3-pyridazinyl]oxymethyl] -1-benzyl-3-[(methoxycarbonyl)methyl]-2-pyrrolidinone-hydrochloride

(25) (3S,5S)-5-[[6-(4-amidinophenyl)-3-pyridazinyl]oxymethyl] -1-[3-(3,4-dimethoxyphenyl)propyl]-3-[(methoxycarbonyl)methyl] -2-pyrrolidinone-hydrochloride

(26) (3S,5S)-5-[[6-(4-amidinophenyl)-3-pyridazinyl]oxymethyl] -3-[(methoxycarbonyl)methyl]-1-[3-( 3-trifluoromethyl-phenyl)propyl]-2-pyrrolidinone-hydrochloride

(27) (3S,5S)-5-[[6-(4-amidinophenyl)-3-pyridazinyl]oxymethyl] -1-[3-(2,4-dichlorophenyl)propyl]-3-[(methoxycarbonyl)methyl] -2-pyrrolidinone-hydrochloride

(28) (3S,5S)-5-[[6-(4-amidinophenyl)-3-pyridazinyl]oxymethyl] -3-[(methoxycarbonyl)methyl]-1-[3-(4-methylthiophenyl)-propyl] -2-pyrrolidinone-hydrochloride

(29) (3S,5S)-5-[[6-(4-amidinophenyl)-3-pyridazinyl]oxymethyl ]-3-[(methoxycarbonyl)methyl]-1-[3-(4-methylsulphonylphenyl)propyl] -2-pyrrolidinone-hydrochloride

(30) (3S,5S)-5-[(4'-amidino-3'-fluoro-4-biphenylyl)oxymethyl] -3-[(methoxycarbonyl)methyl]-1-nicotinoylpyrrolidine-hydrochloride

(31) (3S,5S)-5-[(4'-amidino-3-bromo-4-biphenylyl)oxymethyl] -3-[(methoxycarbonyl)methyl]-1-nicotinoylpyrrolidine-hydrochloride

(32) (3S,5S)-5-[(4'-amidino-2,3-dimethyl-4-biphenylyl)oxymethyl] -3-[(methoxycarbonyl)methyl]-1-nicotinoylpyrrolidine-hydrochloride

(33) (3S,5S)-5-[(4'-amidino-3-nitro-4-biphenylyl)oxymethyl] -3-[(methoxycarbonyl)methyl]-1-nicotinoylpyrrolidine-hydrochloride

(34) (3S,5S)-5-[(3-acetylamino-4'-amidino-4-biphenylyl)oxymethyl]-3-[(methoxycarbonyl)methyl]-1-nicotinoylpyrrolidine-hydrochloride

(35) (3S,5S)-5-[(4'-amidino-3-methanesulphonylamino-4-biphenylyl)oxymethyl] -3-[(methoxycarbonyl)methyl]-1-nicotinoyl-pyrrolidine-hydrochloride

(36) (3S,5S)-5-[(methoxycarbonyl)methyl]-5-[[6-[4-(N-methylamidino)phenyl] -3-pyridazinyl]oxymethyl]-2-pyrrolidinone-hydrochloride Reaction with methylamine instead of ammonium carbonate.

(37) (3S,5S)-5-[(4'-amidino-4-biphenylyl) oxymethyl]-1-( 2-benzothiazolyl)-3-[(methoxycarbonyl)methyl] pyrrolidine-hydrochloride

(38) (3S,5S)-5-[(4'-amidino-4-biphenylyl)oxymethyl]-3-[(methoxycarbonyl)methyl]-1-(2-pyrazinyl)-pyrrolidine-hydrochloride

(39) (3S,5S)-5-[(4'-amidino-4-biphenylyl)oxymethyl]-1-(3-furancarbonyl)-3-[(methoxycarbonyl)methyl]pyrrolidine-hydrochloride

(40) (3S,5S)-5-[(4'-amidino-4-biphenylyl)oxymethyl]-3-[(methoxycarbonyl)methyl]-1-(tetrahydrofuran-2-carbonyl)-pyrrolidine-hydrochloride

(41) (3S,5S)-5-[(4'-amidino-4-biphenylyl)oxymethyl]-3-[(methoxycarbonyl)methyl]-1-[(2-methyl-4-thiazolyl)carbonyl]-pyrrolidine-hydrochloride

(42) (3S,5S)-5-[(4'-amidino-4-biphenylyl)oxymethyl]-3-[(methoxycarbonyl)methyl]-1-(4-pyrazolylcarbonyl)pyrrolidine-hydrochloride

(43) (3S,5S)-5-[(4'-amidino-4-biphenylyl)oxymethyl]-3-[(methoxycarbonyl)methyl]-1-[((1H)-1,2,4-triazol-1-yl)methylcarbonyl] -pyrrolidine-hydrochloride

(44) (3S,5S)-5-[(4'-amidino-4-biphenylyl)oxymethyl]-3-[(methoxycarbonyl)methyl]-1-(4-pyridylcarbonyl)pyrrolidine-hydrochloride

(45) (3S,5S)-5-[[4-(4-amidinophenyl)-2-thiazolyl]aminomethyl] -3-[(methoxycarbonyl)methyl]-2-pyrrolidinone-hydrochloride

(46) (3S,5S)-5-[[N-[5-(4-amidinophenyl)-2-pyrazinyl]-N-methyl]aminomethyl] -3-[(methoxycarbonyl)methyl]-2-pyrrolidinone-hydrochloride

(47) (3S,5S)-5-[(4'-amidino-3-methylsulfenyl-4-biphenylyl)-oxymethyl] -3-[(methoxycarbonyl)methyl]-1-nicotinoyl-pyrrolidine-hydrochloride

(48) (3S,5S)-5-[(4'-amidino-3-methylsulphonyl-4-biphenylyl)-oxymethyl] -3-[(methoxycarbonyl)methyl]-1-nicotinoyl-pyrrolidine-hydrochloride

(49) (3S,5S)-5-[[1-(4-amidinophenyl)piperidin-4-yl]aminomethyl] -3-[(methoxycarbonyl)methyl]-2pyrrolidinone-hydrochloride

(50) (3S,5S)-5-[[N-[1-(4-amidinophenyl)piperidin-4-yl]-N-methyl]aminomethyl] -3-[(methoxycarbonyl)methyl]-2pyrrolidinone-hydrochloride

(51) (3S,5S)-5-[[N-acetyl—N-[1-(4-amidinophenyl)piperidin- 4-yl]]aminomethyl]-3-[(methoxycarbonyl)methyl]-2-pyrrolidinone-hydrochloride

(52) (3S,5S)-5-[[N-[1-(4-amidinophenyl)piperidin-4-yl]-N-methanesulphonyl] aminomethyl]-3-[(methoxycarbonyl)methyl]-2-pyrrolidinone-hydrochloride

(53) (3S,5S)-5-[[1-(4-amidinophenyl)piperidin-4-yl]oxymethyl] -3-[(methoxycarbonyl)methyl]-1-(3-phenylpropyl)-2-pyrrolidinone-hydrochloride

(54) (3S,5S)-5-[2-[1-(4-amidinophenyl)piperazin-4-yl]ethyl] -3-[(methoxycarbonyl)methyl]-2-pyrrolidinone-hydrochloride

(55) (3S,5S)-5-[[1-(4-amidinophenyl)piperidin-4-yl]oxymethyl] -3-[(methoxycarbonyl)methyl]-2pyrrolidinone-hydrochloride Example 7

(3S,5S)-5-[[4-(1-Amino-6-isoquinolinyl)phenyl]oxymethyl] -3-[(methoxycarbonyl)methyl]-2-pyrrolidinone×0.25 H$_2$O 0.5 g of 1-amino-6-(4-hydroxyphenyl)isoquinoline, 0.62 g of (3S,5S)-5-[(methanesulphonyloxy)methyl]-3-[(methoxycarbonyl)methyl]-2-pyrrolidinone and 0.76 g of cesium carbonate are stirred in 20 ml of dry dimethylformamide for 48 hours at 60° C. A further 0.3 g of (3S,5S)-5-[(methanesulphonyloxy)methyl]-3-[(methoxycarbonyl)methyl]-2-pyrrolidinone and 0.5 g of cesium carbonate are added and the mixture is stirred for a further 2½ days at 60° C. After cooling, the mixture is poured onto 100 ml of water and extracted seven times with 50 ml of methylene chloride. The combined organic phases are dried and concentrated by evaporation. After chromatography over a silica gel column with ethyl acetate/methanol (4:1) 0.25 g (29% of theory) are obtained.

Melting point: 220°–222° C.

$R_f$ value: 0.22 (silica gel; ethyl acetate/methanol=4:1)

Calculated: C 67.39; H 5.78; N 10.25; Found: 67.54; 5.98; 9.95.

The following compounds are obtained analogously:

(1) (3S,5S)-5-[[4-(6-isoquinolinyl)phenyl]oxymethyl]-3-[(tert.butyloxycarbonyl)methyl]-2-pyrrolidinone $R_f$ value: 0.23 (silica gel; ethyl acetate)

(2) (3S,5S)-3-[(methoxycarbonyl)methyl]-5-[[4-(2-methyl-1,2,3,4-tetrahydro-6-isoquinolinyl)phenyl]oxymethyl]-2-pyrrolidinone

Example 8

(3S,5S)-3-[(tert.Butyloxycarbonyl)methyl]-5-[[4-(5-cyano-2-pyridyl)phenyl]oxymethyl]-2-pyrrolidinone 1.7 g of 4-(5-cyano-2-pyridyl)phenol, 3.3 g of (3S,5S)-3-[(tert.butyloxycarbonyl)methyl]-5-[(methanesulphonyloxy)methyl]-2-pyrrolidinone and 3.6 g of cesium carbonate are stirred in 25 ml of dry dimethylformamide for 2½ days at ambient temperature. 150 ml of water are added, the mixture is stirred for half an hour and then suction filtered. The solids filtered off are dissolved in ethyl acetate, dried and evaporated down. The crude product is purified by chromatography over a silica gel column using ethyl acetate.

Yield: 2.1 g (60% of theory),

Melting point: 125°–127° C.

$R_f$ value: 0.66 (silica gel; ethyl acetate)

The following compounds are obtained analogously:

(1) (3S,5S)-3-[(tert.butyloxycarbonyl)methyl]-5-[[4-(2-cyano- 5-pyridyl)phenyl]oxymethyl]-2-pyrrolidinone Melting point: 117°–118° C.

$R_f$ value: 0.29 (silica gel; ethyl acetate/cyclohexane=4:1)

(2) (3S,5S)-3-[(tert.butyloxycarbonyl)methyl]-5-[[4-(5-cyano- 2-pyrazinyl)phenyl]oxymethyl]-2-pyrrolidinone Melting point: 155°–156° C.

$R_f$ value: 0.37 (silica gel; ethyl acetate/cyclohexane=4:1)

Calculated: C 64.69; H 5.92; N 13.72; Found: 64.50; 6.02; 13.50.

(3) (3S,5S)-3-[(tert.butyloxycarbonyl)methyl]-5-[[4-(2-cyano- 2-pyrimidyl)phenyl]oxymethyl]-2-pyrrolidinone Potassium tert.butoxide was used instead of cesium carbonate.

Melting point: 152°–154° C.

$R_f$ value: 0.49 (silica gel; ethyl acetate/cyclohexane=4:1)

Calculated: C 64.69; H 5.92; N 13.72; Found: 64.42; 6.04; 13.69.

(4) (3S,5S)-5-[[4-[(2-benzylamino-4-pyridyl)aminocarbonyl]-phenyl]oxymethyl]-3-[(methoxycarbonyl)methyl]-1-(3-phenylpropyl)-2-pyrrolidinone $R_f$ value: 0.55 (silica gel; methylene chloride/methanol= 9:1)

(5) (3S,5S)-5-[[4-[(2-benzylamino-6-chloro-4-pyridyl)aminocarbonyl]phenyl]oxymethyl]-3-[(methoxycarbonyl)methyl]-1-(3-phenylpropyl)-2-pyrrolidinone $R_f$ value: 0.53 (silica gel; methylene chloride/methanol= 9:1)

(6) (3S,5S)-3-[(tert.butyloxycarbonyl)methyl]-5-[[4-(5-cyano- 2-pyrimidyl)phenyl]oxymethyl]-2-pyrrolidinone Melting point: 160°–162° C.

$R_f$ value: 0.51 (silica gel; ethyl acetate/cyclohexane=6:1)

(7) (3S,5S)-3-[(tert.butyloxycarbonyl)methyl]-5-[[4-(5-cyano- 2-thiazolyl)phenyl]oxymethyl]-2-pyrrolidinone Melting point: 127°–129° C.

$R_f$ value: 0.48 (silica gel; ethyl acetate/cyclohexane=6:1)

Example 9

(3S,5S)-5-[(4'-Cyano-4-biphenylyl)oxymethyl]-3-[(methoxycarbonyl)methyl]-1-(2-pyrimidyl)-pyrrolidine 2.0 g of (3S,5S)-5-[(4'-cyano-4-biphenylyl)oxymethyl]-3-[(methoxycarbonyl)methyl]-pyrrolidine-hydrochloride, 0.62 g of 2-chloropyrimidine and 1.8 ml of N-ethyldiisopropylamine are stirred for 3 hours at 140° C. After cooling, the mixture is distributed between water and methylene chloride, the organic phase is separated off, dried and evaporated down. After purification over a silica gel column using methylene chloride/ethyl acetate (9:1) 1.0 g (45% of theory) are obtained.

$R_f$ value: 0.58 (silica gel; methylene chloride/ethyl acetate=9:1)

Calculated: C 70.07; H 5.65; N 13.08; Found: 69.80; 5.69; 12.86.

Example 10

(3S,5S)-5-[(4'-Cyano-4-biphenylyl)oxymethyl]-3-[(methoxycarbonyl)methyl]-1-nicotinoyl-pyrrolidine 5 ml of triethylamine and then 1.4 g of nicotinoyl chloride are added to 3.0 g of (3S,5S)-5-[(4'-cyano-4-biphenylyl)oxymethyl]-3-[(methoxycarbonyl)methyl]-pyrrolidine-hydrochloride in 50 ml of methylene chloride. After 3 hours the mixture is concentrated by rotary evaporation, the residue is mixed with 200 ml of water and extracted with ethyl acetate. The organic phase is separated off, dried and evaporated down. The residue is purified by chromatography over a silica gel column using methylene chloride/methanol (10:1).

Yield: 2.4 g (68% of theory),

Melting point: 110°–112° C.

$R_f$ value: 0.62 (silica gel; methylene chloride/methanol= 10:1)

Calculated: C 71,19; H 5,53; N 9.23; Found: 71.10; 5.25; 9.20.

Example 11

(3S,5S)-5-[2-[(2-amidino-5-isoindolinyl)carbonylamino] ethyl] -3-carboxymethyl-1-(3-phenylpropyl)-2-pyrrolidinone 190 mg of (3S,5S)-3-carboxymethyl-5-[2-[(5-isoindolinyl)carbonylamino]ethyl] -1-(3-phenylpropyl)-2pyrrolidinone, 34 mg of S-ethylisothiourea-hydrobromide, 54 mg of sodium carbonate and 3 ml of dry dimethylformamide are stirred for 4 hours at 100° C. and for 16 hours at ambient temperature. The mixture is then evaporated to dryness and the residue is purified by chromatography over a silica gel column using methanol/conc. aqueous ammonia (9:1).

Yield: 49 mg (25% of theory), $R_f$ value: 0.22 (silica gel; methylene chloride/methanol/ conc. aqueous ammonia=35:15:4)

The following compounds are obtained analogously:

(1) (3S,5S)-5-[[(2-amidino-5-isoindolinyl)carbonylamino] methyl]-3-carboxymethyl-1-(3-phenylpropyl)-2-pyrrolidinone× 2 H₂O $R_f$ value: 0.33 (silica gel; methylene chloride/methanol/ conc. aqueous ammonia=35:15:4)

Calculated: C 60.08, H 6.86, N 13.63; Found: 60.35; 6.88; 13.48.

(2) (3S,5S)-5-[2-[(2-amidino-1,2,3,4-tetrahydro-7-isoquinolinyl)carbonylamino] ethyl]-3-carboxymethyl-1-(3phenylpropyl)-2-pyrrolidinone $R_f$ value: 0.34 (silica gel; methanol/conc. aqueous ammonia=9:1)

(3) (3S,5S)-5-[[(2-amidino-1,2,3,4-tetrahydro-7-isoquinolinyl)carbonylamino]methyl]-3-carboxymethyl-1-(3-phenylpropyl)-2-pyrrolidinone $R_f$ value: 0.36 (silica gel; methanol/conc. aqueous ammonia=9:1)

Calculated: C 65.97; H 6.77; N 14.24; Found: 65.73; 6.83; 14.01.

(4) (3s,5s)-5-[[(3-amidino-1H-2,3,4,5-tetrahydro-3-benzazepin- 7-yl)carbonylamino]methyl]-3-carboxymethyl-1-(3-phenylpropyl)-2-pyrrolidinone $R_f$ value: 0.27 (silica gel; methanol/conc. aqueous ammonia=95:5)

Calculated: C 66.51; H 6.98; N 13.85; Found: 66.85; 6.97; 13.76.

(5) (3S,5S)-5-[(3-amidino-1H-2,3,4,5-tetrahydro-3-benzazepin- 7-yl)oxymethyl]-3-carboxymethyl-1-(3-phenylpropyl)- 2-pyrrolidinone×2 $H_2O$ $R_f$ value: 0.17 (silica gel; methylene chloride/methanol/ conc. ammonia=50:50:5)

Calculated: C 63.01; H 7.44; N 10.89; Found: 62.81; 7.20; 11.18.

(6) (3S,5S)-5-[[4-(1-amidino-4-piperidinyl)phenyl]oxymethyl]-3-carboxymethyl-1-(3-phenylpropyl)-2-pyrrolidinone×1 $H_2O$ $R_f$ value: 0.31 (silica gel; methylene chloride/methanol/ conc. aqueous ammonia=8:4:1)

Calculated: C 65.86; H 7.50; N 10.97; Found: 65.70; 7.56; 11.18.

Example 12

(3S,5S)-3-Carboxymethyl-5-[2-[(5-isoindolinyl)carbonylamino]-ethyl]-1-(3-phenylpropyl)-2-pyrrolidinone A mixture of 3 ml of trifluoroacetic acid and 3 ml of methylene chloride is added dropwise at ambient temperature to 510 mg of (3S,5S)-5-[2-[(2-tert.butyloxycarbonyl-5-isoindolinyl)carbonylamino]ethyl] -3-carboxymethyl-1-(3-phenylpropyl)-2-pyrrolidinone×0.75 $H_2O$ in 3 ml of methylene chloride and then the resulting mixture is stirred for one hour at ambient temperature. It is evaporated to dryness, the residue is taken up in 5 ml of methylene chloride and made just alkaline with methanolic ammonia. It is evaporated down and the residue is purified by chromatography over a silica gel column using methylene chloride/methanol/conc. aqueous ammonia (10:6:1).

Yield: 250 mg (60% of theory), $R_f$ value: 0.46 (silica gel; methylene chloride/methanol/ conc. aqueous ammonia=35:15:4)

Mass spectrum: $(M+H)^+=450$

The following compounds are obtained analogously:

(1) (3S,5S)-3-carboxymethyl-5-[[(5-isoindolinyl)carbonylamino]methyl] -1-(3-phenylpropyl)-2-pyrrolidinone $R_f$ value: 0.48 (silica gel; methylene chloride/methanol/ conc. aqueous ammonia=35:15:4)

(2) (3S,5S)-3-carboxymethyl-1-(3-phenylpropyl)-5-[2-[(1, 2,3,4-tetrahydro-7-isoquinolinyl)carbonylamino]ethyl]-2-pyrrolidinone $R_f$ value: 0.40 (silica gel; methanol/ethyl acetate/conc. aqueous ammonia=20:10:1)

Calculated: C 69.95; H 7.18; N 9.06; Found: 70.10; 7.26; 8.99.

(3) (3S,5S)-3-carboxymethyl-1-(3-phenylpropyl)-5-[[(1,2,3, 4-tetrahydro-7-isoquinolinyl)carbonylamino]methyl] -2-pyrrolidinone $R_f$ value: 0.38 (silica gel; methanol/ethyl acetate/conc. aqueous ammonia=20:10:1)

Calculated: C 69.47; H 6.95; N 9.35; Found: 69.64; 7.02; 9.09.

(4) (3S,5S)-3-carboxymethyl-1-(3-phenylpropyl)-5-[[(1H-2,3,4,5-tetrahydro-3-benzazepin-7-yl)carbonylamino]methyl]-2-pyrrolidinone×1 $H_2O$ $R_f$ value: 0.13 (silica gel; methanol/ethyl acetate/conc. aqueous ammonia=20:10:1)

Calculated: C 67.33; H 7.33; N 8.73; Found: 67.44; 7.36; 8.83.

(5) (3S,5S)-3-carboxymethyl-1-(3-phenylpropyl)-5-[2-[(1H-2,3,4,5-tetrahydro-3-benzazepin-7-yl)carbonylamino] ethyl] -2-pyrrolidinone×0.5 $H_2O$ $R_f$ value: 0.45 (silica gel; methylene chloride/methanol= 9:1, developed twice)

Calculated: C 69.11; H 7.46; N 8.64; Found: 68.84; 7.68; 8.49.

(6) (3S,5S)-3-carboxymethyl-1-(3-phenylpropyl)-5-[2-[[4-(4 -piperidinyl)phenyl]carbonylamino]ethyl]-2-pyrrolidinone×0.75 $H_2O$ $R_f$ value: 0.32 (silica gel; methylene chloride/methanol= 9:1), Calculated: C 68.96; H 7.68; N 8.32; Found: 69.08; 7.69; 8.41.

(7) (3S,5S)-3-carboxymethyl-1-(3-phenylpropyl)-5-[[[4-(4 -piperidinyl)phenyl]carbonylamino]methyl]-2-pyrrolidinone×1 $H_2O$ $R_f$ value: 0.13 (silica gel; methanol/ethyl acetate/conc. aqueous ammonia=20:10:1), Calculated: C 67.85; H 7.53; N 8.48; Found: 68.03; 7.52; 8.51.

(8) (3S,5S)-3-carboxymethyl-1-(3-phenylpropyl)-5-[(1H-2,3,4,5-tetrahydro-3-benzazepin-7-yl)oxymethyl]-2-pyrrolidinone×1 $H_2O$ $R_f$ value: 0.22 (silica gel; methanol/ethyl acetate/conc. aqueous ammonia=20:10:1), Calculated: C 68.70; H 7.54; N 6.16; Found: 68.67; 7.36; 6.12.

(9) (3S,5S)-3-carboxymethyl-1-(3-phenylpropyl)-5-[[4-(4 -piperidinyl)phenyl]oxymethyl]-2-pyrrolidinone×1 $H_2O$ $R_f$ value: 0.14 (silica gel; methylene chloride/ethyl acetate/conc. aqueous ammonia=20:10:1), Calculated: C 69.21; H 7.74; N 5.98; Found: 69.38; 7.71; 6.15.

Example 13

(3S,5S)-5-[2-[(2-tert.Butyloxycarbonyl-5-isoindolinyl)carbonylamino]ethyl]-3-carboxymethyl-1-(3-phenylpropyl)-2-pyrrolidinone×0.75 $H_2O$ 0.7 g of (3S,5S)-5-[2-[(2-tert.butyloxycarbonyl-5-isoindolinyl)-carbonylamino] ethyl]-3-[(methoxycarbonyl)methyl]-1-(3-phenyl-propyl)-2-pyrrolidinone×0.5 $H_2O$ in 3 ml of methanol are mixed with 3.73 ml of 1N sodium hydroxide solution and the mixture is stirred for 3 hours at ambient temperature. The methanol content is evaporated off and the residue is acidified by the addition of saturated aqueous potassium hydrogen sulphate solution. The precipitate is suction filtered and dried.

Yield: 510 mg (73% of theory), $R_f$ value: 0.48 (silica gel; ethyl acetate/glacial acetic acid=50:1), Calculated: C 66.12; H 7.25; N 7.46; Found: 66.08; 7.30;

7.42.

The following compounds are obtained analogously:

(1) (3S,5S)-5-[[(2-tert.butyloxycarbonyl-5-isoindolinyl)-carbonylamino] methyl]-3-carboxymethyl-1-(3-phenylpropyl)-2-pyrrolidinone×1.2 H$_2$O $R_f$ value: 0.54 (silica gel; ethyl acetate/glacial acetic acid=50:1), Calculated: C 64.66; H 7.13; N 7.54; Found: 64.42; 6.87; 7.69.

(2) (3S,5S)-5-[2-[(2-tert.butyloxycarbonyl-1,2,3,4-tetrahydro- 7-isoquinolinyl)carbonylamino]ethyl]-3-carboxymethyl- 1-(3-phenylpropyl)-2-pyrrolidinone×0.75 H$_2$O Calculated: C 66.59; H 7.42; N 7.28; Found: 66.49; 7.39; 7.33.

(3) (3S,5S)-5-[[(2-tert.butyloxycarbonyl-1,2,3,4-tetrahydro-7-isoquinolinyl)carbonylamino]methyl]-3-carboxymethyl-1-(3-phenylpropyl)-2-pyrrolidinone×0.75 H$_2$O Calculated: C 66.11; H 7.25; N 7.46; Found: 66.05; 7.26; 7.52.

(4) (3S,5S)-5-[[4-(5-benzyloxycarbonylamidino-2-pyridyl)-phenyl]oxymethyl] -3-carboxymethyl-2-pyrrolidinone Example 14

(3S,5S)-5-[2-[(2-tert.Butyloxycarbonyl-5-isoindolinyl)carbonylamino]ethyl] -3-[(methoxycarbonyl)methyl]-1-(3-phenyl-propyl)- 2-pyrrolidinone×0.5 H$_2$O 0.75 g of 2-tert.butyloxycarbonyl-5-isoindoline carboxylic acid in 15 ml of dry dimethylformamide are mixed at −10° C. with 0.41 g of 1-hydroxy-1H-benzotriazole, 1.06 g of (3S,5S)-5-(2-aminoethyl)-3-[(methoxycarbonyl)methyl]-1-(3-phenylpropyl)-2-pyrrolidinone-hydrochloride in 10 ml of dimethylformamide, 0.83 ml of triethylamine and 0.74 g of N,N'-dicyclohexylcarbodiimide. The reaction mixture is stirred for 16 hours and slowly heated to ambient temperature. It is evaporated to dryness, the residue is mixed with 50 ml of water and extracted four times with 20 ml of ethyl acetate. The combined organic phases are washed four times with saturated aqueous sodium hydrogen carbonate solution and twice with saturated aqueous saline solution, dried and evaporated down. The residue is purified by chromatography over a silica gel column with ethyl acetate.

Yield: 0.7 g (42% of theory), $R_f$ value: 0.33 (silica gel; ethyl acetate)

Calculated: C 67.11; H 7.39; N 7.34; Found: 67.26; 7.65; 7.44.

The following compounds are obtained analogously:

(1) (3S,5S)-5-[[(2-tert.butyloxycarbonyl-5-isoindolinyl)carbonylamino]methyl]-3-[(methoxycarbonyl)methyl]-1-(3-phenyl-propyl)-2-pyrrolidinone×0.25 H$_2$O $R_f$ value: 0.40 (silica gel; ethyl acetate)

Calculated: C 67.19; H 7.18; N 7.58; Found: 67.12; 7.49; 7.66.

(2) (3S,5S)-5-[2-[(2-tert.butyloxycarbonyl-1,2,3,4-tetrahydro- 7-isoquinolinyl)carbonylamino]ethyl]-3-[(methoxycarbonyl)-methyl] -1-(3-phenylpropyl)-2-pyrrolidinone $R_f$ value: 0.35 (silica gel; ethyl acetate)

(3) (3S,5S)-5-[[(2-tert.butyloxycarbonyl-1,2,3,4-tetrahydro-7-isoquinolinyl)carbonylamino]methyl]-3-[(methoxycarbonyl)-methyl] -1-(3-phenylpropyl)-2-pyrrolidinone $R_f$ value: 0.47 (silica gel; ethyl acetate)

Example 15

(3S,5S)-5-[(4'-Cyano-4-biphenylyl)oxymethyl]-3-[(methoxycarbonyl)methyl] -1-(2-pyridyl)-2-pyrrolidinone To 6 g of (3R,5S)-3-allyl-5-[(4'-cyano-4-biphenylyl)oxymethyl]-1-(2-pyridyl)-2-pyrrolidinone in 60 ml of methylene chloride are added 50 ml of acetonitrile, 300 mg of ruthenium(III)chloride-hydrate, 19.7 g of sodium metaperiodate and 110 ml of water and the mixture is stirred very vigorously. After one hours' reaction 110 ml of water and 60 ml of methylene chloride are added and the reaction mixture is suction filtered over kieselguhr. The organic phase is washed with sodium sulphite solution and water, then dried and evaporated down. The residue is mixed with 80 ml of methanol and a few milliliters of methanolic hydrochloric acid and left to stand for 30 minutes at ambient temperature. The mixture is evaporated down and distributed between ethyl acetate and 1M sodium carbonate solution. The organic phase is washed with water, dried and evaporated down. The residue is purified by chromatography over a silica gel column with cyclohexane/ethyl acetate (75:25).

Yield: 2.8 g (44% of theory),

Melting point: 125°–127° C.

$R_f$ value: 0.38 (silica gel; cyclohexane/ethyl acetate=7:3)

Calculated: C 70.73; H 5.25; N 9.52; Found: 70.46; 5.35; 9.61.

The following compound is obtained analogously:

(1) (3S,5S)-5-[(4'-cyano-4-biphenylyl)oxymethyl]-3-[(methoxycarbonyl)methyl] -1-(3-pyridyl)-2-pyrrolidinone $R_f$ value: 0.39 (silica gel; cyclohexane/ethyl acetate=1:9).

Example 16

(3S,5S)-5-[[(7-Cyano-1H-2,3,4,5-tetrahydro-3-benzazepin-3-yl)carbonylamino]methyl]-3-[(methoxycarbonyl)methyl]-1-(3-phenylpropyl)-2-pyrrolidinone×0.25 H$_2$O At 0° C. within 5 minutes a filtered mixture of 1.0 g of (3S,5S)-5-aminomethyl-3-[(methoxycarbonyl)methyl]-1-(3-phenylpropyl)- 2-pyrrolidinone-hydrochloride, 0.4 ml of triethylamine and 20 ml of dry tetrahydrofuran is added dropwise to 0.5 g of carbonyldiimidazole and 0.35 g of imidazole in 15 ml of dry tetrahydrofuran. After 12 minutes stirring at 0° C., 0.57 g of 7-cyano-1H-2,3,4,5-tetrahydro-3-benzazepine in 15 ml of tetrahydrofuran are added. The mixture is stirred for a further half hour at 0° C. and for 4 hours at ambient temperature, then evaporated down and the residue is distributed between ethyl acetate and dilute aqueous hydrochloric acid. The organic phase is separated off, dried and evaporated down. After chromatography over a silica gel column with ethyl acetate/methanol (20:1) 0.84 g (56% of theory) are obtained.

$R_f$ value: 0.56 (silica gel; ethyl acetate/methanol=20:1)

Calculated: C 68.69; H 6.86; N 11.05; Found: 68.60; 6.97; 10.89.

The following compounds are obtained analogously:

(1) (3S,5S)-5-[2-[(7-cyano-1H-2,3,4,5-tetrahydro-3-benzazepin- 3-yl)carbonylamino]ethyl]-3-[(methoxycarbonyl)methyl]-1-(3-phenylpropyl)-2-pyrrolidinone×0.2 H$_2$O $R_f$ value: 0.25 (silica gel; ethyl acetate/methanol=19:1)

Calculated: C 69.26; H 7.00; N 10.77; Found: 69.39; 7.26; 10.42.

(2) (3S,5S)-5-[2-[(7-cyano-1,2,3,4-tetrahydro-2-isoquinolinyl)carbonylamino]ethyl]-3-[(methoxycarbonyl)methyl]-1-(3-phenylpropyl)-2-pyrrolidinone×0.7 H$_2$O $R_f$ value: 0.49 (silica gel; ethyl acetate/methanol=19:1)

Calculated: C 67.61; H 6.93; N 10.87; Found: 67.78; 7.13; 10.60.

(3) (3S,5S)-5-[[(7-cyano-1,2,3,4-tetrahydro-2-isoquinolinyl)carbonylamino]methyl] -3-[(methoxycarbonyl)methyl]-1-(3-phenylpropyl)-2-pyrrolidinone×0.25 H$_2$O $R_f$ value: 0.25 (silica gel; ethyl acetate)

Calculated: C 68.20; H 6.64; N 11.36; Found: 68.27; 6.80; 10.97.

Example 17

(3S,5S)-5-[[(3-tert.Butyloxycarbonyl-1H-2,3,4,5-tetrahydro- 3-benzazepin-7-yl)carbonylamino]methyl]-3-carboxymethyl- 1-(3-phenylpropyl)-2-pyrrolidinone To 6.6 g of (3R,5S)-3-allyl-5-[[(3-tert.butyloxycarbonyl-1H-2,3,4,5-tetrahydro-3-benzazepin-7-yl)carbonylamino] methyl] -1-(3-phenylpropyl)-2-pyrrolidinone in 30 ml of acetonitrile and 30 ml of carbon tetrachloride, 17.1 g of sodium metaperiodate in 125 ml of water and 80 mg of ruthenium(III)-chloridehydrate are added with vigorous stirring and the mixture is stirred vigorously for a further 5 hours at ambient temperature. The reaction mixture is filtered over kieselguhr, extracted with methylene chloride, the combined organic phases are washed twice with 100 ml of 4% sodium hydrogen sulphite solution and with water and saturated saline solution, dried, filtered over activated charcoal and evaporated down. The residue is purified by chromatography over a silica gel column with methylene chloride/cyclohexane/methanol/conc. aqueous ammonia (68:15:15:2).

Yield: 4 g (52% of theory), $R_f$ value: 0.22 (silica gel; methylene chloride/cyclohexane/methanol/conc. aqueous ammonia=68:15:15:2)

The following compounds are obtained analogously:

(1) (3S,5S)-5-[[[4-(1-tert.butyloxycarbonyl-4-piperidinyl)phenyl]carbonylamino]methyl]-3-carboxymethyl- 1-(3-phenylpropyl)-2-pyrrolidinone $R_f$ value: 0.25 (silica gel; methylene chloride/cyclohexane/methanol/conc. aqueous ammonia=68:15:15:2)

(2) (3S,5S)-5-[(3-tert.butyloxycarbonyl-1H-2,3,4,5-tetrahydro- 3-benzazepin-7-yl)oxymethyl]-3-carboxymethyl-1-(3-phenyl-propyl)-2-pyrrolidinone $R_f$ value: 0.36 (silica gel; methylene chloride/cyclohexane/methanol/conc. aqueous ammonia=68:15:15:2)

(3) (3S,5S)-5-[[4-(1-tert.butyloxycarbonyl-4-piperidinyl)phenyl]oxymethyl] -3-carboxymethyl-1-(3-phenylpropyl)-2-pyrrolidinone $R_f$ value: 0.38 (silica gel; methylene chloride/cyclohexane/methanol/conc. aqueous ammonia=68:15:15:2)

(4) (3S,5S)-3-carboxymethyl-5-[[6-(4-cyanophenyl)-3-pyridazinyl]oxymethyl] -1-(3-phenylpropyl)-2-pyrrolidinone $R_f$ value: 0.31 (silica gel; methylene chloride/cyclohexane/methanol/conc. aqueous ammonia=68:15:15:2)

(5) (3S,5S)-3-carboxymethyl-5-[[6-(4-cyanophenyl)-3-pyridazinyl]aminomethyl]-1-(3-phenylpropyl)-2-pyrrolidinone $R_f$ value: 0.22 (silica gel; methylene chloride/cyclohexane/methanol/conc. aqueous ammonia=68:15:15:2)

Example 18

(3S,5S)-5-[2-[(3-Amidino-1H-2,3,4,5-tetrahydro-3-benzazepin- 7-yl)carbonylamino]ethyl]-3-carboxymethyl-1-(3-phenylpropyl)-2-pyrrolidinone 1.2 g of (3S,5S)-3-carboxymethyl-1-(3-phenylpropyl)-5-[2- [(1H-2,3,4,5-tetrahydro-3-benzazepin-7-yl)carbonylamino]ethyl]-2-pyrrolidinone×0.5 H$_2$O, 25 ml of water, 25 ml of tetrahydrofuran, 0.8 ml of triethylamine and 1.8 g of 1-amidino-3,5-dimethylpyrazole are refluxed for 4 hours over a steam bath. A further 0.3 g of 1-amidino-3,4-dimethylpyrazole and 20 ml of water are added and the mixture is heated for 3 hours. After cooling, it is evaporated down and the residue is triturated with diethylether. It is decanted off from the ether and the residue is chromatographed over a silica gel column with methylene chloride/methanol/conc. aqueous ammonia (10:15:1). For further purification it is chromatographed over a silica gel column with tetrahydrofuran/water (5:1).

Yield: 0.4 g (31% of theory), $R_f$ value: 0.35 (silica gel; methylene chloride/methanol/conc. aqueous ammonia=10:20:1)

Calculated: C 67.03; H 7.18; N 13.48; Found: 67.15; 7.29; 13.88.

Example 19

(3S,5S)-5-[2-[(3-tert.Butyloxycarbonyl-1H-2,3,4,5-tetrahydro- 3-benzazepin-7-yl)carbonylamino]ethyl]-3-carboxymethyl- 1-(3-phenylpropyl)-2-pyrrolidinone 3.8 g of (3S,5S)-5-aminoethyl-3-carboxymethyl-1-(3-phenylpropyl)- 2-pyrrolidinone, 50 ml of dry methylene chloride, 50 ml of dry acetonitrile and 1.8 ml of chlorotrimethylsilane are stirred for 30 minutes at ambient temperature and 2.5 hours at 45° C., then cooled and evaporated down. The residue is taken up in 75 ml of dry tetrahydrofuran and cooled to 0° C. (reaction solution a)).

4 g of 3-tert.butyloxycarbonyl-1H-2,3,4,5-tetrahydro-3-benzazepine- 7-carboxylic acid, 50 ml of dry tetrahydrofuran and 1.5 ml of N-methyl-morpholine are combined at −30° C. with 1.8 ml of isobutyl-chloroformate, which is added dropwise thereto, and stirred for 30 minutes at this temperature. Then reaction solution a) and 1.5 ml of N-methyl-morpholine are added at −30° C. The mixture is stirred for 3 hours at −30° C. and heated to ambient temperature overnight with stirring. The mixture is acidified with aqueous citric acid solution, extracted with diethylether and the combined organic phases are washed with 10% citric acid solution and water, dried and evaporated down. After purification over a silica gel column with diethylether/ tetrahydrofuran/water (40:20:1), 4.1 g (57% of theory) are obtained.

$R_f$ value: 0.25 (silica gel; diethylether/tetrahydrofuran/water= 30:20:1)

The following compound is obtained analogously:

(1) (3S,5S)-5-[2-[[4-[4-(N-tert.butyloxycarbonyl)piperidinyl]phenyl] carbonylamino]ethyl]-3-carboxymethyl-1-(3-phenylpropyl)-2-pyrrolidinone $R_f$ value: 0.32 (silica gel; diethylether/tetrahydrofuran/water= 30:20:1)

Example 20

(3S,5S)-5-[[[4-(1-Amidino-4-piperidinyl)phenyl]carbonylamino] -methyl]-3-carboxymethyl-1-(3-phenylpropyl)-2-pyrrolidinone×1 H$_2$O 0.5 g of (3S,5S)-3-carboxymethyl-1-(3-phenylpropyl)-5-[[[4-(4-piperidinyl)phenyl]carbonylamino]methyl]-2-pyrrolidinone×1 H$_2$O, 6 ml of ethanol, 0.06 ml of glacial acetic acid and 85 mg of cyanamide are refluxed for 2 days, then cooled and evaporated down. The residue is triturated with water, the water is decanted off and the residue is triturated with acetone. The solid substance is suction filtered, dried and purified by chromatography over a silica gel column with methanol/conc. aqueous ammonia (95:5).

Yield: 0.2 g (37% of theory),

Calculated: C 64.78; H 7.31; N 13.03; Found: 64.71; 7.18; 13.10.

The following compound was obtained analogously:

(1) (3S,5S)-3-carboxymethyl-5-[(3'-guanidino-4-biphenylyl)-oxymethyl] -1-nicotinoyl-pyrrolidine

Example 21

(3S,5S)-5-[[6-(4-Cyanophenyl)-3-pyridazinyl]oxymethyl]- 3-[(methoxycarbonyl)methyl]-1-(3-phenylpropyl)-2-pyrrolidinone 2.7 g of (3S,5S)-3-carboxymethyl-5-[[6-(4-cyanophenyl)-

3-pyridazinyl]oxymethyl]-1-(3-phenylpropyl)-2-pyrrolidinone are stirred with 50 ml of methanol and 5 ml of methanolic hydrochloric acid for 45 minutes at about 50° C. and then evaporated down. After purification over a silica gel column using methylene chloride/methanol (40:1) 1.9 g are left (68% of theory).

$R_f$ value: 0.58 (silica gel; methylene chloride/methanol= 15:1)

The following compounds are obtained analogously:
(1) (3S,5S)-5-[[6-(4-Cyanophenyl)-3-pyridazinyl]aminomethyl] -3-[(methoxycarbonyl)methyl]-1-(3-phenylpropyl)-2-pyrrolidinone $R_f$ value: 0.86 (silica gel; methylene chloride/methanol/ cyclohexane/conc. aqueous ammonia=68:15:15:2)
(2) (3S,5S)-5-[[4-(5-amidino-2-pyrimidyl)phenyl]oxymethyl] -3-[(isopropoxycarbonyl)methyl]-2-pyrrolidinone-hydrochloride Carried out with isopropanolic hydrochloric acid.
(3) (3S,5S)-3-[(methoxycarbonyl)methyl]-5-[[4-(1,2,3,4-tetrahydro- 6-isoquinolinyl)phenyl]oxymethyl]-2-pyrrolidinone-hydrochloride
(4) (3S,5S)-5-[[4-(5-amidino-2-pyridyl)phenyl]oxymethyl] -3-[(cyclopentyloxycarbonyl)methyl]-2-pyrrolidinone-hydrochloride
(5) (3S,5S)-5-[[4-(5-amidino-2-pyridyl)phenyl]oxymethyl] -3-[(cyclohexyloxycarbonyl)methyl]-2-pyrrolidinone-hydrochloride
(6) (3S,5S)-5-[[4-(5-amidino-2-pyrimidyl)phenyl]oxymethyl] -3-[(cycloheptyloxycarbonyl)methyl]-2-pyrrolidinone-hydrochloride
(7) (3S,5S)-5-[[4-(5-amidino-2-pyrimidyl)phenyl]oxymethyl] -3-[(cyclohexylmethyloxycarbonyl)methyl]-2-pyrrolidinone-hydrochloride
(8) (3S,5S)-5-[[4-(5-amidino-2-pyridyl)phenyl]oxymethyl] -3-[(ethyloxycarbonyl)methyl]-2-pyrrolidinone-hydrochloride
(9) (3S,5S)-5-[[4-(5-amidino-2-pyridyl)phenyl]oxymethyl] -3-[[(2-norbornyl)oxycarbonyl]methyl]-2-pyrrolidinone-hydrochloride
(10) (3S,5S)-5-[[4-(5-amidino-2-pyridyl)phenyl]oxymethyl] -3-[[(2-indanyl)oxycarbonyl]methyl]-2-pyrrolidinone-hydrochloride
(11) (3S,5S)-5-[[4-(5-amidino-2-pyrimidyl)phenyl]oxymethyl] -3-[(cyclohexyloxycarbonyl)methyl]-2-pyrrolidinone-hydrochloride Example 22

(3S,5S)-5-[[6-(4-Cyanophenyl)-3-pyridazinyl]aminomethyl] -3-[(methoxycarbonyl)methyl]-2-pyrrolidinone 1.2 g of (3S,5S)-5-aminomethyl-3-[(methoxycarbonyl)methyl]-2-pyrrolidinone, 1.3 g of 3-chloro-6-(4-cyanophenyl)-pyridazine, 0.64 g of sodium carbonate and 10 ml of dimethylsulphoxide are stirred for 5 hours at 120° C., then cooled and stirred into a saturated aqueous saline solution and extracted with ethyl acetate containing some tetrahydrofuran. The organic phase is washed with water, dried, filtered and evaporated down. The crude product is dissolved in about 150 ml of a mixture of methylene chloride and methanol, about 8 g of silica gel are added and the mixture is then evaporated down again. This residue is placed on a silica gel column and the product is eluted with methylene chloride/methanol (15:1).

Yield: 0.95 g (43% of theory), $R_f$ value: 0.38 (silica gel; methylene chloride/methanol= 15:1)

Example 23

(3S,5S)-5-[[[6-(4-Cyanophenyl)-3(2H)-pyridazinon-4-yl] carbonyl]aminomethyl]-3-[(methoxycarbonyl)methyl]-2-pyrrolidinone 1.2 g of 6-(4-cyanophenyl)-3(2H)-pyridazinone-4-carboxylic acid and 0.8 ml of N-methyl-morpholine are heated in 100 ml of dimethylformamide and the resulting suspension is cooled to −20° C. At this temperature, 0.7 ml of isobutyl chloroformate are added and the mixture is stirred for about 1.5 hours at −20° C. 0.95 g of (3S,5S)-5-aminomethyl-3-[(methoxycarbonyl)-methyl]-2-pyrrolidinone in 20 ml of dimethylformamide are added dropwise thereto and the mixture is then stirred for 3 hours at −20° C. It is then heated slowly to ambient temperature, the reaction mixture is stirred into saturated saline solution and extracted with ethyl acetate/tetrahydrofuran. The organic phase is washed with water, dried, filtered and evaporated down. After purification over a silica gel column using methylene chloride/ methanol (15:1) 0.7 g are left (34% of theory).

$R_f$ value: 0.31 (silica gel; methylene chloride/methanol= 15:1)

The following compounds are obtained analogously:
(1) (3S,5S)-5-[[[6-(4-cyanophenyl)-2-methyl-3(2H)-pyridazinon- 4-yl]carbonyl]aminomethyl]-3-[(methoxycarbonyl)methyl]-2-pyrrolidinone Carried out in tetrahydrofuran $R_f$ value: 0.49 (silica gel; methylene chloride/methanol= 15:1)
(2) (3S,5S)-5-[[[6-(4-cyanophenyl)-3(2H)-pyridazinon-4-yl]carbonyl]aminomethyl]-3-[(methoxycarbonyl)methyl]-1-(3-phenylpropyl)-2-pyrrolidinone Carried out in dimethylsulphoxide/tetrahydrofuran $R_f$ value: 0.34 (silica gel; methylene chloride/methanol= 15:1)

Example 24

(3S,5S)-5-[[3-[(4-Cyanophenyl)aminocarbonyl]-2(1H)-pyridon- 1-yl]methyl]-3-[(methoxycarbonyl)methyl]-2-pyrrolidinone 29.9 g of 3-[(4-cyanophenyl)aminocarbonyl]-2(1H)-pyridone and 17.3 g of potassium carbonate in 250 ml of dimethylsulphoxide are stirred at 80° C. for one hour. Then a solution of 33.3 g of (3S,5S)-5-[(methanesulphonyloxy)methyl]-3-[(methoxycarbonyl)methyl]-2-pyrrolidinone in dimethylsulphoxide is added and the mixture is stirred for 27 hours at 80° C. After cooling, the reaction mixture is poured onto 4 liters of ice, the suspension is stirred for 1.5 hours, then suction filtered and the filter residue is washed twice with 100 ml of water. The filter residue is dissolved at 85° C. in 500 ml of dimethylformamide, the solution is evaporated to a total volume of about 75 ml with heating and is then cooled. After standing overnight the crystals are suction filtered, washed with 25 ml of cold dimethylformamide and twice with 75 ml of ethyl acetate, 50 ml of acetone and diethylether and dried.

Yield: 14.7 g (29% of theory), $R_f$ value: 0.57 (silica gel; methylene chloride/methanol/ glacial acetic acid=30:1:0.1; developed twice)

The following compounds are obtained analogously:
(1) (3S,5S)-5-[[3-[(4-cyanophenyl)aminocarbonyl]-2(1H)-pyridon- 1-yl]methyl]-3-[(methoxycarbonyl)methyl]-1-(3-phenylpropyl)- 2-pyrrolidinone Purified over a silica gel column using methylene chloride/methanol (40:1)

$R_f$ value: 0.54 (silica gel; methylene chloride/methanol= 30:1; developed twice )

(2) (3S,5S)-5-[[5-[(4-cyanophenyl)aminocarbonyl]-2(1H)-pyridon- 1-yl]methyl]-3-[(methoxycarbonyl)methyl]-1-(3-phenylpropyl)-2-pyrrolidinone Purified over a silica gel column with ethyl acetate/cyclohexane=4:1 and 9:1

$R_f$ value: 0.18 (silica gel; ethyl acetate/cyclohexane=4:1)

(3) (3S,5S)-5-[[5-[(4-cyanophenyl)aminocarbonyl]-2,4(1H,3H)-pyrimidindion-3-yl]methyl]-3-[(methoxycarbonyl)methyl]-1-(3-phenylpropyl)-2-pyrrolidinone Carried out with sodium hydrogen carbonate. Purification over a silica gel column with methylene chloride/methanol (100:1), methylene chloride/methanol/conc. aqueous ammonia (50:1:0.1) and ethyl acetate/cyclohexane (5:1)

$R_f$ value: 0.32 (silica gel; methylene chloride/methanol/conc. aqueous ammonia=19:1:0.1)

Example 25

(3S,5S)-5-[[4-[(2-Benzylamino-4-pyridyl)aminocarbonyl]phenyl] -oxymethyl]-3-carboxymethyl-1-(3-phenylpropyl)-2-pyrrolidinone 0.3 g of (3S,5S)-5-[[4-[(2-benzylamino-4-pyridyl)aminocarbonyl]phenyl]oxymethyl] -3-[(methoxycarbonyl)methyl]-1-(3-phenylpropyl)-2-pyrrolidinone, 8 ml of methanol and 1.5 ml of 1N sodium hydroxide solution are heated for 30 minutes over a steam bath. The mixture is then cooled, diluted with water, acidified with 1N hydrochloric acid and evaporated down. The residue is purified by chromatography over a silica gel column using methylene chloride/methanol/conc. aqueous ammonia (85:15:1) and (80:20:2).

Yield: 0.15 g (52% of theory), $R_f$ value: 0.40 (silica gel; methylene chloride/methanol/conc. aqueous ammonia=80:20:2)

The following compound is obtained analogously:

(1) (3S,5S)-5-[[4-[(2-benzylamino-6-chloro-4-pyridyl)aminocarbonyl] phenyl]oxymethyl]-3-carboxymethyl-1-(3-phenylpropyl)-2-pyrrolidinone Example 26

(3S,5S)-5-[[4-(5-Aminomethyl-2-pyridyl)phenyl]oxymethyl] -3-carboxymethyl-2-pyrrolidinone Prepared from (3S,5S)-5-[[4-(5-cyano-2-pyridyl)phenyl]oxymethyl] -3-[(methoxycarbonyl)methyl]-2-pyrrolidinone by saponification analogously to Example 13 and subsequent hydrogenation with Raney nickel in methanol/conc. aqueous ammonia.

Example 27

(3S,5S)-5-[[4-(5-amidino-2-pyridyl)phenyl]oxymethyl]-3-[(benzyloxycarbonyl)methyl] -2-pyrrolidinone-p-toluenesulphonic acid Prepared from (3S,5S)-5-[[4-(5-amidino-2-pyridyl)phenyl] oxymethyl]-3-carboxymethyl-2-pyrrolidinone by reacting with benzylalcohol in the presence of p-toluenesulphonic acid.

Example 28

(3S,5S)-5-[[4-(5-Acetoxymethyloxycarbonylamidino-2-pyridyl)-phenyl]oxymethyl] -3-[(methoxycarbonyl)methyl]-2-pyrrolidinone Prepared from (3S,5S)-5-[[4-(5-amidino-2-pyridyl)phenyl]oxymethyl] -3-[(methoxycarbonyl)methyl]-2-pyrrolidinone-hydrochloride by reacting with acetoxymethyl-(4-nitrophenyl)carbonate in methylene chloride and in the presence of N-ethyldiisopropylamine.

The following compound is obtained analogously:

(1) (3S,5S)-5-[[4-[5-[(1-acetoxyethyl)oxycarbonylamidino]- 2-pyridyl]phenyl]oxymethyl]-3-[(methoxycarbonyl)methyl]-2-pyrrolidinone Example 29

(3S,5S)-5-[[4-(5-Benzyloxycarbonylamidino-2-pyridyl)phenyl]oxymethyl] -3-[(pivaloyloxymethyloxycarbonyl)methyl]-2-pyrrolidinone Prepared from (3S,5S)-5-[[4-(5-benzyloxycarbonylamidino-2-pyridyl)phenyl] oxymethyl]-3-carboxymethyl-2-pyrrolidinone by reacting with chloromethylpivalate in dimethylsulphoxide in the presence of potassium carbonate and sodium iodide.

The following compounds are obtained analogously:

(1) (3S,5S)-5-[[4-(5-benzyloxycarbonylamidino-2-pyridyl)-phenyl]oxymethyl] -3-[[[1-(ethyloxycarbonyloxy)ethyl]oxycarbonyl] -methyl]-2-pyrrolidinone (2) (3S,5S)-5-[[4-(5-benzyloxycarbonylamidino-2-pyridyl)phenyl]oxymethyl] -3-[[[1-(cyclohexyloxycarbonyloxy)ethyl]oxycarbonyl]methyl]- 2-pyrrolidinone Example 30

(3S,5S)-5-[[4-(5-amidino-2-pyridyl)phenyl]oxymethyl]-3-[(pivaloyloxymethyloxycarbonyl)methyl]-2-pyrrolidinone-hydrochloride Prepared from (3S,5S)-5-[[4-(5-benzyloxycarbonylamidino-2-pyridyl)phenyl]oxymethyl]-3-[(pivaloyloxymethyloxycarbonyl)-methyl]-2-pyrrolidinone by hydrogenation with palladium on charcoal in dimethylformamide in the presence of hydrochloric acid.

The following compounds are obtained analogously:

(1) (3S,5S)-5-[[4-(5-amidino-2-pyridyl)phenyl]oxymethyl]-3-[[[1-(ethyloxycarbonyloxy)ethyl]oxycarbonyl]methyl]-2-pyrrolidinone-hydrochloride (2) (3S,5S)-5-[[4-(5-amidino-2-pyridyl)phenyl]oxymethyl]-3-[[[1-(cyclohexyloxycarbonyloxy)ethyl]oxycarbonyl]methyl] -2-pyrrolidinone-hydrochloride Example 31

(3S,5S)-5-[[[5-[(O,O'-Diethylphosphono)amidino]-2-pyridyl]-phenyl]oxymethyl] -3-[(methoxycarbonyl)methyl]-2-pyrrolidinone Prepared from (3S,5S)-5-[[4-(5-amidino-2-pyridyl)phenyl]-oxymethyl] -3-[(methoxycarbonyl)methyl]-2-pyrrolidinone-hydrochloride by reacting with diethylphosphate chloride in tetrahydrofuran in the presence of sodium hydroxide solution.

Example 32

(3S,5S)-3-Carboxymethyl-5-[[4-(1,2,3,4-tetrahydro-6isoquinolinyl)phenyl]oxymethyl] -2-pyrrolidinone-hydrochloride 2,3 g of (3S,5S)-3-Carboxymethyl-5-[[4-(6-isoquinolinyl)-phenyl] oxymethyl]-2-pyrrolidinone in a mixture of 200 ml of glacial acetic acid and 20 ml of 2N hydrochloric acid are hydrogenated in the presence of 0,5 g of platinum-(IV)-oxide under a hydrogen pressure of 3 bar at ambient temperature. The catalyst is removed by filtration and the filtrate is evaporated to dryness. After adding toluene and evaporating to dryness several times, the residue is triturated with 50 ml acetone, then suction filtered and washed with acetone several times.

Yield: 1.8 g (70% of theory)

$R_f$ value: 0,60 (reversed phase silica gel; methanol/10% aqueous saline solution=6:4)
Mass spectrum (M+H)$^+$=381

Example 33

Dry ampoule containing 2.5 mg of active substance per 1 ml

| Composition: | |
|---|---|
| Active substance | 2.5 mg |
| Mannitol | 50.0 mg |
| Water for injections ad | 1.0 ml |

Preparation:

The active substance and mannitol are dissolved in water. After transferring the solution to the ampoule, it is freeze-dried.

At the point of use, the solution is made up with water for injections.

Example 34

Dry ampoule containing 35 mg of active substance per 2 ml

| Composition: | |
|---|---|
| Active substance | 35.0 mg |
| Mannitol | 100.0 mg |
| Water for injections ad | 2.0 ml |

Preparation:

The active substance and mannitol are dissolved in water. After transferring the solution to the ampoule, it is freeze-dried.

At the point of use, the solution is made up with water for injections.

Example 35

Tablet containing 50 mg of active substance

| Composition: | |
|---|---|
| (1) Active substance | 50.0 mg |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granules. From this mixture, compressed tablets are produced, biplanar, facetted on both sides and notched on one side. Diameter of tablets: 9 mm.

Example 36

Tablet containing 350 mg of active substance

| Composition: | |
|---|---|
| (1) Active substance | 350.0 mg |
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granules. From this mixture, compressed tablets are produced, biplanar, facetted on both sides and notched on one side. Diameter of tablets: 12 mm.

Example 37

Capsules containing 50 mg of active substance

| Composition: | |
|---|---|
| (1) Active substance | 50.0 mg |
| (2) Dried corn starch | 58.0 mg |
| (3) Powdered lactose | 50.0 mg |
| (4) Magnesium stearate | 2.0 mg |
| | 160.0 mg |

Preparation:

(1) is triturated with (3). This triturate is added to the mixture of (2) and (4), with thorough mixing.

This powdered mixture is packed into size 3 hard gelatin oblong capsules in a capsule filling machine.

Example 38

Capsules containing 350 mg of active substance

| Composition: | |
|---|---|
| (1) Active substance | 300.0 mg |
| (2) Dried corn starch | 46.0 mg |
| (3) Powdered lactose | 30.0 mg |
| (4) Magnesium stearate | 4.0 mg |
| | 430.0 mg |

Preparation:

(1) is triturated with (3). This triturate is added to the mixture of (2) and (4), with thorough mixing.

This powdered mixture is packed into size 0 hard gelatin oblong capsules in a capsule filling machine.

We claim:

1. A 2-pyrrolidinone of the formula

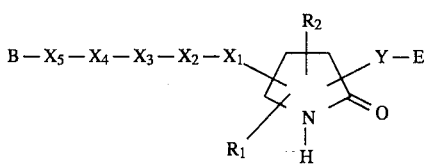

wherein with the proviso that one of the substituents $R_1$, $R_2$, $B—X_5—X_4—X_3—X_2—X_1$ or $E—Y$ may also replace the hydrogen atom attached to the ring nitrogen atom, $R_1$ denotes a hydrogen atom, a pyridinyl group, a $C_{1-4}$-alkyl group which may be substituted by a phenyl, trifluoromethylphenyl, methylsulphenylphenyl, methylsulphinylphenyl, methylsulphonylphenyl, fluorophenyl, chlorophenyl, methylphenyl, methoxyphenyl, dichlorophenyl or dimethoxyphenyl group, a methyl group substituted by a carboxy, methoxycarbonyl or dimethylaminocarbonyl group, a 2-methoxy-ethyl or a phenyl group, a carbonyl group which is substituted by a phenyl, methyl, methoxymethyl, amino, methylamino, ethylamino or dimethylamino group, or a sulphonyl group substituted by a methyl, phenyl, methoxyphenyl, amino, methylamino or dimethylamino group, and $R_2$ denotes a hydrogen atom or a methyl group, with the provisos that
a carbonyl group of the group $R_1$ is not linked to the nitrogen atom of the 2-pyrrolidinone ring, and
a sulphonyl group of the group $R_1$ is not linked to the nitrogen atom of the 2-pyrrolidinone ring and is also not attached to a carbon atom adjacent to the nitrogen atom of the 2-pyrrolidinone ring, $X_1$ denotes a bond or a methylene or ethylene group, $X_2$ denotes a bond, an oxygen atom, a —CONH— group or an imino group optionally substituted by a methyl, acetyl or methanesulphonyl group, $X_3$ represents a pyrazinylene or pyridazinylene group each optionally substituted by a methyl or hydroxy group or by a chlorine atom, and $X_5$ represents a phenylene group optionally substituted by a fluorine, chlorine or bromine atom, or by a methyl, trifluoromethyl, methoxy, nitro, amino, acetylamino, methanesulphonylamino, methylsulphenyl, methylsulphinyl or methylsulphonyl group or by two methyl groups, or $X_3$ represents a phenylene group optionally substituted by a fluorine, chlorine or bromine atom, or by a methyl, trifluoromethyl, methoxy, nitro, amino, acetylamino, methanesulphonylamino, methylsulphenyl, methylsulphinyl or methylsulphonyl group or by two methyl groups, and $X_5$ represents a pyrazinylene or pyridazinylene group each optionally substituted by a methyl or hydroxy group or by a chlorine atom, $X_4$ represents a bond or an —NHCO— group, B denotes an aminomethyl, cyano, amidino, guanidino or amino group, whilst if B denotes an amino, aminomethyl, amidino or guanidino group, a hydrogen atom at one of the nitrogen atoms may be replaced by a methyl, benzyl, ($C_{1-4}$-alkoxy)carbonyl, benzyloxycarbonyl or $R_4$—CO—O—($R_5$CH)—O—CO— group, wherein
$R_4$ is a $C_{1-4}$-alkyl group and
$R_5$ is a hydrogen atom or a methyl group, or, if B denotes an amidino group, a hydrogen atom may also be replaced by an O,O'-dimethyl-phosphono or O,O'-diethylphosphono group, Y represents a methylene or ethylene group and E denotes a carboxy group, an alkoxycarbonyl group having a total of 2 to 7 carbon atoms, a phenylalkoxycarbonyl group having 1 to 3 carbon atoms in the alkoxy moiety, an O-methylphosphono, O,O'-dimethylphosphono, phosphono, $R_8O$—CO— or $R_6$—CO—O—($R_7$CH)—O—CO— group, wherein $R_6$ denotes a $C_{1-4}$-alkyl group, a cyclohexyl or phenyl group, a $C_{1-4}$-alkoxy group or a $C_{5-7}$-cycloalkoxy group, $R_7$ denotes a hydrogen atom or a methyl group and $R_8$ denotes a cycloalkyl, cycloalkylmethyl or cycloalkylethyl group each having 5 to 8 carbon atoms in the cycloalkyl moiety, whilst the above-mentioned cycloalkyl moieties may additionally be substituted by a $C_{1-4}$-alkyl group or by a $C_{1-4}$-alkyl group and 1 to 3 methyl groups, by a methoxy, ethoxy, dimethylamino, diethylamino or trifluoromethyl group and, furthermore, in the above-mentioned cycloalkyl moieties a methylene group may be replaced by an oxygen atom or by a methylimino or ethylimino group, with the proviso that there are at least 2 carbon atoms between the cyclic heteroatom and the next heteroatom, or $R_8$ represents a cyclohexenyl or cyclohexenylmethyl group, whilst the above-mentioned cyclohexenyl moieties may additionally be substituted by a methyl group, with the proviso that the above-mentioned cyclohexenyl moieties are not linked to the oxygen atom of the adjacent —O—CO— group via a carbon atom from which a double bond starts, or $R_8$ represents a bicycloalkyl or bicycloalkylalkyl group each having 6 to 8 carbon atoms in the bicycloalkyl moiety and 1 or 2 carbon atoms in the alkyl moiety, whilst the above-mentioned bicycloalkyl moieties may additionally be substituted by 1 to 3 methyl groups, or $R_8$ represents a bicycloalkenyl or bicycloalkenylalkyl group each having 6 to 8 carbon atoms in the bicycloalkenyl moiety and 1 or 2 carbon atoms in the alkyl moiety, whilst the above-mentioned bicycloalkenyl moieties may additionally be substituted by 1 to 3 methyl groups, with the proviso that the above-mentioned bicycloalkenyl moieties are not linked to the oxygen atom of the adjacent —O—CO— group via a carbon atom from which a double bond starts, or $R_8$ represents a benzocycloalkenyl group having a total of 9 or 10 carbon atoms, or $R_8$ represents an alkenyl or alkynyl group each having 3 to 5 carbon atoms with the proviso that the above-mentioned alkenyl or alkynyl groups are not linked to the oxygen atom of the adjacent —O—CO— group via a carbon atom from which a double or triple bond starts, or $R_8$ represents a cinnamyl group, with the proviso that the shortest distance between the groups B and E is at least 10 bonds, or a tautomer or a pharmaceutically acceptable salt thereof.

2. A compound according to claim 1, wherein B, E, $X_1$ to $X_5$ and Y are as hereinbefore defined in claim 1, $R_1$ denotes a hydrogen atom or with the proviso that $R_1$ is in 1-position, $R_1$ may denote a hydrogen atom, a pyridinyl group, a $C_{1-4}$-alkyl group which may be substituted by a phenyl, trifluoromethylphenyl, methylsulphenylphenyl, methylsulphinylphenyl, methylsulphonylphenyl, fluorophenyl, chlorophenyl, methylphenyl, methoxyphenyl, dichlorophenyl or dimethoxyphenyl group, a methyl group substituted by a carboxy, methoxycarbonyl or dimethylaminocarbonyl group, a 2-methoxy-ethyl or a phenyl group, and $R_2$ denotes a hydrogen atom or a methyl group, or a tautomer or a pharmaceutically acceptable salt thereof.

3. A compound according to claim 2, wherein

E—Y is in 3-position, and

B—$X_5$—$X_4$—$X_3$—$X_2$—$X_1$ $R_1$ is in 1-, 4- or 5-position, or a tautomer or a pharmaceutically acceptable salt thereof.

4. A compound according to claim 1, wherein $R_1$ is in 1-position,

E—Y is in 3-position, and

B—$X_5$—$X_4$—$X_3$—$X_2$—$X_1$ is in 5-position, whereby $R_1$ represents a hydrogen atom or a 3-phenylpropyl group, $R_2$ represents a hydrogen atom, $X_1$ denotes a methylene or ethylene group, $X_2$ denotes a bond, an oxygen atom or a —CONH— or imino group, $X_3$ represents an optionally methyl-substituted pyridazin-3,6-ylene or a 3-hydroxy-pyridazin-4,6-ylene group, and $X_5$ an optionally chlorine-substituted 1,4-phenylene group, or $X_3$ an optionally methyl-substituted 1,4-phenylene group, and $X_5$ represents a pyrazin-2,5-ylene group, $X_4$ denotes a bond, B denotes a cyano group, an amidino group in which, at one of the nitrogen atoms, a hydrogen atom may be replaced by an alkoxycarbonyl group having a total of 2 to 5 carbon atoms, Y denotes a methylene group and E denotes a carboxy group or an alkoxycarbonyl group having a total of 2 to 5 carbon atoms, with the proviso that the shortest distance between groups B and E is at least 10 bonds, or a tautomer or pharmaceutically acceptable salt thereof.

5. A compound according to claim 4, wherein $R_1$ represents a hydrogen atom or a 3-phenylpropyl group, $X_2$—$X_1$ denotes an —O—$CH_2$—, —NH—$CH_2$— or —CONH—$CH_2$— group, $X_3$ represents a pyridazin-3,6-ylene or 3-hydroxy-pyridazin-4,6-ylene group, and $X_5$ represents a 1,4-phenylene group, or $X_3$ represents a 1,4 phenylene group, and $X_5$ represents a pyrazin-2,5-ylene group, $X_4$ denotes a bond, B denotes an amidino group wherein, at one of the nitrogen atoms, a hydrogen atom may be replaced by an alkoxycarbonyl group with a total of 2 to 5 carbon atoms, Y denotes a methylene group and E denotes a carboxy group or an alkoxycarbonyl group having a total of 2 to 5 carbon atoms, or a tautomer or pharmaceutically acceptable salt thereof.

6. (3S,5S)-5-[[6-(4-amidinophenyl)-3-pyridazinyl]oxymethyl-3-carboxymethyl-1-(3-phenylpropyl)-2-pyrrolidinone or a pharmaceutically acceptable salt thereof.

7. (3S,5S)-5-[[6-(4-amidinophenyl)-3-pyridazinyl]aminomethyl]-3-carboxymethyl-2-pyrrolidinone or a pharmaceutically acceptable salt thereof.

8. (3S,5S)-5-[[4-(5-amidino-2-pyrazinyl)phenyl]oxymethyl]-3-carboxymethyl-2-pyrrolidinone or a pharmaceutically acceptable salt thereof.

9. (3S,5S)-5-[[[6-(4-amidinophenyl)-3(2H)-pyridazinon-4-yl]carbonyl]aminomethyl]-3-carboxymethyl-1-(3-phenylpropyl)-2-pyrrolidinone, a tautomer and pharmaceutically acceptable salts thereof.

* * * * *